US012728259B2

(12) United States Patent
Yazdan-Shahmorad et al.

(10) Patent No.: US 12,728,259 B2
(45) Date of Patent: Sep. 8, 2026

(54) CORTICAL NETWORK STRUCTURE MEDIATES RESPONSE TO BRAIN STIMULATION

(71) Applicant: University of Washington, Seattle, WA (US)

(72) Inventors: Azadeh Yazdan-Shahmorad, Seattle, WA (US); Julien Bloch, Seattle, WA (US); Alexander Greaves-Tunnell, Seattle, WA (US); Eric Shea-Brown, Seattle, WA (US); Ali Shojaie, Seattle, WA (US); Zaid Harchaoui, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 614 days.

(21) Appl. No.: 17/901,496

(22) Filed: Sep. 1, 2022

(65) Prior Publication Data

US 2023/0080414 A1 Mar. 16, 2023

Related U.S. Application Data

(60) Provisional application No. 63/240,767, filed on Sep. 3, 2021.

(51) Int. Cl.
*A61N 1/05* (2006.01)
*A61N 1/36* (2006.01)
(Continued)

(52) U.S. Cl.
CPC ....... *A61N 1/0529* (2013.01); *A61N 1/36082* (2013.01); *A61N 1/36139* (2013.01); *A61N 5/0601* (2013.01); *A61N 5/067* (2021.08)

(58) Field of Classification Search
None
See application file for complete search history.

(56) References Cited

U.S. PATENT DOCUMENTS 11,266,839 B1 3/2022 John
2007/0067003 A1 * 3/2007 Sanchez ............ A61N 1/36082 607/45

(Continued)

FOREIGN PATENT DOCUMENTS

CN 107361741 A 11/2017
CN 108606792 A 10/2018

(Continued)

OTHER PUBLICATIONS

Haris, A., Shojaie, A. & Simon, N. (2019). Nonparametric Regression with Adaptive Truncation via a Convex Hierarchical Penalty. Biometrika, 106, 87-107.

(Continued)

*Primary Examiner* — Amanda L Steinberg
*Assistant Examiner* — Sefra D. Manos
(74) *Attorney, Agent, or Firm* — Christensen O'Connor Johnson Kindness PLLC

(57) ABSTRACT

Cortical network structure that mediates response to brain stimulation, and associated systems and methods are disclosed herein. In one embodiment, a method for brain stimulation includes: delivering an input stimulus to an area of the brain, via a cortical implant; in response to delivering the input stimulus, generating neural signals in the brain; and generating a predicted outcome of the input stimulus. The predicted outcome is based on a set of data derived from a model that combines: protocol features that are brain agnostic, and network features that are based on interactions between neural nodes of the brain.

20 Claims, 39 Drawing Sheets

(51) Int. Cl.
*A61N 5/06* (2006.01)
*A61N 5/067* (2006.01)

(56) References Cited

U.S. PATENT DOCUMENTS

2009/0088680 A1* 4/2009 Aravanis ............ A61K 48/0058 604/21
2011/0295143 A1* 12/2011 Leuthardt ............ A61B 5/4064 600/544
2014/0243714 A1* 8/2014 Ward .................. A61M 5/1723 601/2
2015/0157862 A1* 6/2015 Greenberg ........... H05K 3/4061 607/116
2017/0311882 A1* 11/2017 Saab .................... A61B 5/4848
2018/0178014 A1* 6/2018 Tass ....................... A61N 1/361
2018/0236230 A1* 8/2018 Pilly ........................ A61B 5/24
2019/0054295 A1 2/2019 Pannu
2020/0023189 A1* 1/2020 Gribetz .............. A61N 1/36196
2020/0230413 A1* 7/2020 Madhavan ............. A61B 5/055
2021/0346699 A1 11/2021 Miocinovic
2021/0375480 A1* 12/2021 Mahon ................. A61B 5/4064
2023/0045240 A1* 2/2023 Park ......................... A61N 1/36

FOREIGN PATENT DOCUMENTS

CN 112741613 A 5/2021
CN 2022049105 A1 3/2022

OTHER PUBLICATIONS

Yazdan-Shahmorad, A. et al. (2018), "Targeted Cortical Reorganization Using Optogenetics in Non-Human Primates", ELife, 7, 1-21.
Bloch, J. et al., "Cortical network structure mediates response to stimulation: an optogenetic study in non-human primates" bioRxiv, May 5, 2021.
Yazdan-Shahmorad, A. et al. "Brain stimulation can rewire and heal damaged neural connections, but it isn't clear how—research suggests personalization may be key to more effective therapies", The Conversation, Jul. 6, 2022.
Welch, P. The use of fast Fourier transform for the estimation of power spectra: a method based on time averaging over short, modified periodograms. IEEE Transactions on audio and electroacoustics 15, 70-73 (1967).
Bliss, T.V.P. and Collingridge, G., A synaptic model of memory; LTP in the hippocampus. Nature 361, 31-39 (1993).
Markram, H. Lubke, J., Frotscher, M. & Sakmann, B, Regulation of synaptic efficacy by coincidence of postsynaptic APs and SPSPs. Sciene 275, 2013-215. ISSNL 00368075 (1997).
Bi, G.-q. & Poo, M.-m, Synaptic Modifications in Cultured Hippocampul Neurons: Dependence on Spike Timing, Syanptic Strength, and Postsynaptic Cell Type. J. Neurosci 18, 1-9. ISSN: 0270-6474 (1998).
Zhang, L. I., Tao, H. W., Holt, C. E., Harris, W. A. & Poo, M. M. A Critical window for cooperation and competition among developing retinotectal synapses. Nature. ISSN: 00280836 (1998).
Song, S., Miller, K. D. & Abbott, L. F. Competitive Hebbian learning through spike-timing-dependent synaptic plasticity. Nature Neuroscience. ISSN: 10976256 (2000).
Friedman, J., Hastie, T. & Tibshirani, R. The Elements of Statistical Learning 10 (Springer Series in Statistics New York, 2001).
Milo, R. et al. Network motifs: Simple building blocks of complex networks. Sciece. ISSN: 00368075 (2002).
Barrat, A., Barthelemy, M., Pastor-Satorras, R. & Vespignani, A. The arthitecture of complex weighted networks. Proceedings of the National Academy of Sciences of the United States of America 101, 3747-3752 (2004).
Boyd, S. & Vandenberghe, L. Convez Optimization (Cambridge University Press, 2004).
Milo, R. et al. Superfamilies of Evolved and Designed Networks. Science. ISSN: 00368075 (2004).
Onnela, J. P., Saramaki, J., Lertesz, J. & Kaki, K. Intensity and coherence of motifs in weighted complex networks. Physical Review E—Statistical, Nonlinear, and Soft Matter Physics 71 (2005).
Waites, A. B., Stanislavsky, A., Abbott, D. F. & Jackson, G. D. Effect of prior cognitive state on resting state networks measured with functional connectivity. Human Brain Mapping 24, 59-68. ISSN: 10659471 (2005).
Jackson, A. Mavoori, J. & Fetz, E. E. Long-term motor cortex plasticity induced by an electronic neural implant. Nature 444, 56-60. ISSN: 14764687 (2006).
Garrity, A. G. et al. Aberrant "default mode" functional connectivity in schizophrenia. America Journal of Phychiatry. ISSN: 002953X (2007).
Stam, C. J., Jones, B. F., Nolte, G., Breakspear, M. & Scheltens, P. Small-world networks and functional connectivity in Alzheimer's disease. Cerebral Cortex 17, 92-99. ISSN: 10473211 (2007).
Meinshausen, N. & Buhlmann, P. Stability selection. Journal of the Royal Statistical Society: Series B (Statistical Methodology) 72, 417-473 (2010).
Rebesco, J. M., Stevenson, I. H., Kording, K. P., Solla, S. A. & Miller, L. E. Rewiring neural interactions by micro-stimulation. Frontiers in Systems Neuroscience 4, 1-15. ISSN: 16625137 (2010).
Keller, C. J. et al. Intrinsic functional architecture predicts electrically evoked responses in the human brain. Proceedings of the National Academy of Sciences of the United States of America 108, 17234. ISSN: 10916490 (2011).
Pernice, V., Staude, B. Cardanobile, S. & Rotter, S. How structure determines correlations in neuronal networks. PLoS Computational Biology 7. ISSN: 1553734X (2011).
Rebesco, J. M. & Miller, L. E. Enhanced detection threshold for in vivo cortical stimulation produced by Hebbian conditioning. Journal of Neural Engineering 8. ISSN: 17412560 (2011).
Zhao, L., Beverlin, B., Netoff, T. & Nykamp, D. Q. Synchrinization from second order network connectivity statistics. Frontiers in Computational Neurosciene 5, 1-16. ISSN: 16625188 (2011).
Edwardson, M. A., Lucas, T. H., Carey, J. R. & Fetz, E. E. New modalities of brain stimulation for stroke rehabilitation. Experimental Brain Research 224, 335-358 (2013).
Lozano, A. M. & Lipsman, N. Probing and Regulating Dysfunctional Circuits Using Deep Brain Stimulation. Neuron 77, 406-424. ISSN: 08966273 (2013).
Wang, Z. et al. The Relationship of Anatomical and Functional Connectivity to Resting-State Connectivity in Primate Somatosensory Cortex. Neuron 78, 1116-1126. ISSN: 08966273 (2013).
Hu, Y., Trousdale, J., Josic, K. & Shea-Brown, E. Local paths to global coherence: Cutting networks down to size. Physical Review E—Statistcal, Nonlinear, and Soft Matter Physics. ISSN: 15502376 (2014).
Kaiser, R. H., Andrews-Hanna, J. R., Wagner, T. D. & Pizzagalli, D. A. Large-scale network dysfunction in major depressive disorder: A meta-analysis of resting-state functional connectivity. JAMA Psychiatry 72, 603-611. ISSN: 2168622X (2015).
Ledochowitsch, P. et al. Strategies for optical control and simultaneous electrical readout of extended cortical circuits. Journal of Neurscience Methods 256, 220-230 (2015).
Levy, R. M. et al. Epidural Electrical Stimulation for Stroke Rehabilitation. Neurorehabilitation and Neural Repair 30, 107-119. ISSN: 15526844 (2016).
Yazdan-Shahmorad, A. et al. A Large-Scale Interface for Optogenetic Stimulation and Recording in Nonhuman Primates. Neuron 89, 927-939. ISSN: 10974199 (2016).
Hariz, M. My 25 stimulating years with DBS in Parkinson's disease. Journal of Parkinson's Disease 7, S33-S41. ISSN: 1877718X (2017).
Ocker, G. K. et al. From the statistics of connectivity to the statistics of spike times in neural networks. Current Opinion in Neurobiology. ISSN: 18736882 (2017).
Seeman, S. C., Mogen, B. J., Fetz, E. E. & Perlmutter, S. I. Paired Stimulation for Spike-Timing-Dependent Plasticity in Primate Sensormotor Cortez. The Journal of Neuroscience 37, 1935-1949. ISSN: 0270-6474 (2017).

(56) References Cited

OTHER PUBLICATIONS

Keller, C. J. et al. Induction and quantification of excitability changes in human cortical networks. Journal of Neurosciene 38, 5384-5398. ISSN: 15292401 (2018).
Bloch, J. A. et al. Cortical Stimulation Induces Network-Wilde Coherence Change in Non-Human Primate Somatosensory Cortex. Proceedings of the Annual International Conference of the IEEE Engineering in Medicine and Biology Society, EMBS, 6446-6449. ISSN: 1557170X (2019).
Huang, Y. et al. Intracortical Dynamics Underlying Repetitive Stimulation Predicts Changes in Network Connectivity. The Journal of neuroscience 39, 6122-6135, ISSN: 15292401 (2019).
Khateeb, K., Griggs, D., Sabes, P.N. & Yazdan-Shahmorad, A Convection Enhanced Delivery of Optogenetic Adeno-associated Viral Vector to the Cortex of Rhesus Macaque Under Guidance of Online MRI Images. Journal of visualized experiments: JoVE 147 (2019).
Zarzycki, M.Z. & Domitrz, I. Stimulation-induced side effects after deep brain stimulation—A systematic review Acta Neuropsychiatrica 32, 57-64. ISSN: 16015215 (2020).
Yang, Y. et al. Modelling and prediction of the dynamic responses of large-scale brain networks during direct electrical stimulation. Nature Biomedical Engineering (2021).
Arrais, M. et al., "Design of optimal multi-site brain stiumlation protocols via neuro-inspired epilepsy models for abatement of interictal discharges," Journal of Neural Engineering, 18 (2021) 016024.
Bliss, T.V.P & G.L Collingridge, "A synaptic model of memory: long-term potentiation in the hippocampus," Nature, vol. 361, Jan. 7, 1993, pp. 31-39.
Boes, A. et al., "Effects of Transcranial Magnetic Stimulation on the Human Brain Revealed by Intracraial Electrocorticography," Abstracts / Brain Stimulation 12 (2019) 385-592; from ClinicalKey.com by Elsevier, Mar. 6, 2023.
Chen, C.H. et al., "An Integrated Circuit for Simultaneous Extracellular Electrophysiology Recording and Optogenetic Neural Maniuplation," IEEE Transactions on Biomedical Engineering, vol. 64, No. 3, Mar. 2017, pp. 557-568.
El-Shamayleh, Y. and G.D. Horowitz, "Primate optogenetics: Progress and prognosis," PNAS, Dec. 26, 2019, vol. 116:No. 52, 26195-26203.
Frovlov, N.S. et al., "Dynamics of functional connectivity in multilayer cortical brain network during sensory information processing," The European Pyscial Journal Special Topics, 228, 2381-2389 (2019).
Jafari, Z. et al., "Neural oscillations and brain stimulation in Alzheimer's disease," Progress in Neurobiology, Elsevier, 194 (2020) 101878.
Johnson, L.A. et al., "Direct electrical stimulation of the somatosensory cortex in humans using electrocorticography electrodes: a qualitative and quantitative reoprt," Journal of Neural Engineering, 20 (2013) 036021 (7pp).
Khambhati, A. N. et al., "Long-term brain network reorganization predicts responsive neurostimulation outcomes for focal epilepsy," Science Translational Medicine Research Article, 13 eabf6588, Aug. 25, 2021.
Kown, K.Y. et al., "Opto-uECoG Array: A Hybrid Neural Interface With Transparent uECoG Electrode Array and Integrated LEDs for Optogenetics," IEEE Transactions on Biomedical Circuits and Systems, vol. 7, No. 5, Oct. 2013, pp. 593-600.
Nauleau, Alexandre, "Optogenetic perturbations to unveil brain-scale functional organization in zebrafish larva," Laboratoire Jean Perrin: Master Physics of Complex Systems; Universit'e Pierre et Marie Curie, 43 pages.
Park, D.-W. et al., "Fabrication and utility of a transparent graphene neural electrode array for electrophysiology, in vivo imaging, and optogenetics," Nature Protocols, vol. 11:No. 11, 2016, 2201-2222.
Paz, J.T., "Optogenetic Stimulation of the Thalamus to Bi-Directionally Control Epipleptic Seizures," Abstracts / Brain Stimulation 10 (2017) 346-540; from ClinicalKey.com by Elsevier on Mar. 6, 2023.
Pronold, J. et al., "Multi-area spiking network models of macague and human visual cotrices," JuSER; NEST Conference 2015, As, Norway, Jun. 25, 2018-Jun. 26, 2018.
Romanelli, P. et al., "A novel neural prosthesis providing long-term electrocorticography recording and cortical stimulation for epilepsy and brain-computer interface," J Neurogurg vol. 130, Apr. 2019, pp. 1166-1179.
Van Bloogis, D. et al., "Closed-Loop Cortical Network Stimulation as a Treatment for Epilepsy Arising From the Primary Motor Cortex," Abstracts / Brain Stimulation 14 (2021) 1589-1707; from ClinicalKey.com by Elsevier on Mar. 6, 2023.

* cited by examiner

Protocol features

Block #: 1 2 3 4 5

Predicted electrode pair: ●
Other electrodes: ○
Stim site: ◍

Network features

Predicted electrode pair: ●
Other electrodes: ○
Stim site: ◍

CORTICAL NETWORK STRUCTURE MEDIATES RESPONSE TO BRAIN STIMULATION

CROSS-REFERENCE TO RELATED APPLICATION

This application claims the benefit of U.S. Provisional Application No. 63/240,767, filed Sep. 3, 2021, the disclosure of which is expressly incorporated herein by reference in its entirety.

STATEMENT OF GOVERNMENT LICENSE RIGHTS

This invention was made with government support under Grant Nos. K12 HD073945, P51 OD010425, R01 GM133848 and T32 LM012419, awarded by the National Institutes of Health (NIH), and Grant Nos. DMS-1722246, DMS-1915855, DMS-2023239 and ERC 1028725, awarded by the National Science Foundation (NSF). The government has certain rights in the invention.

BACKGROUND

From schizophrenia to epilepsy, aberrant network-level functional connectivity underlies a variety of neural disorders. As such, the ability to modify network-level functional connectivity may provide therapies for neural disorders. Brain stimulation has demonstrated promise as a means for modifying large-scale functional connectivity, but the mapping from stimulation to the resulting modification remains unclear.

The prevalent approach for inducing targeted connectivity change is neural stimulation informed by Spike-Timing Dependent Plasticity (STDP). STDP is a phenomenon in which synaptic strengths are modified as a function of the delay between the firing times of the pre- and post-synaptic neurons. While STDP was initially observed in monosynaptic connectivity strength between isolated neuron pairs in vitro, its application was eventually translated to larger-scale, less isolated connections in vivo. In response to the more challenging in vivo setting, this translation coincided with stimulation of a larger set of neurons instead of monosynaptic connections of isolated neuron pairs and the measurement of functional connectivity changes (FCC) instead of direct synaptic strength changes. In line with the original in vitro studies, these experiments are based on an expectation that pairwise stimulation would drive FCC only between the stimulation targets. Some studies reported successful induction of targeted FCC, while others reported inconsistent results across stimulation targets. Notably, these studies also reported that stimulation-induced FCC were found to extend beyond the stimulation sites to other recorded regions. Follow up studies investigated the extent of this phenomenon in primates and found that paired stimulation reliably results in FCC extending over a large-scale surrounding network. These results highlight the need for an updated framework which accurately predicts network-wide stimulation-induced FCC in vivo.

Recent research indicates that network-level functional connectivity is not only affected by stimulation, but also is involved in shaping the response to stimulation. For example, underlying functional connectivity has been shown to shape stimulation-induced neural activity propagation as well as influence the therapeutic outcome of neural stimulation interventions for Parkinson's disease and depression. Early results have also indicated that network-level FCC induced by stimulation are correlated to baseline functional connectivity. Despite the demonstrated relevance of the underlying network for shaping the response to stimulation, the question of how to effectively parse and analyze a brain network to inform stimulation remains unanswered. Accordingly, systems and methods are needed for an updated framework for network-level stimulation induced FCC that can be used for treatments of neural disorders.

SUMMARY

This summary is provided to introduce a selection of concepts in a simplified form that are further described below in the Detailed Description. This summary is not intended to identify key features of the claimed subject matter.

Briefly, the inventive technology is directed to neural interfaces and computational modeling resulting in a model which jointly considers characteristics of the stimulation protocol (also referred to as "protocol features") and the underlying network-level functional connectivity for prediction of network-wide stimulation-induced FCC. The inventive technology employs optogenetics, a stimulation technology in which neurons are rendered light-sensitive by viral-mediated expression of opsins and thus able to be activated by incident light to activate target neural regions while simultaneously recording without electrical artifact. FCC is measured at the network level by recording neural activity via a micro-electrocorticography (ECoG) array covering ~1 $cm^2$ of the primary sensorimotor cortex. In different embodiments, the neural activity may be recorded by surface electrodes or in-depth electrodes that are coupled at a depth of the brain of the subject. We then parse underlying network-level functional connectivity with summarizing metrics borrowed from and inspired by graph theory. Finally, we employ a nonparametric hierarchical additive model to predict network-level FCC while allowing maximal interpretability of identified feature mappings. We develop and test the model in the sensorimotor cortex of two non-human primates (NHPs) to ensure maximal clinical translation. We calculated the change from a resting-state block to the following stimulation block which we refer to as SS-FCC, and calculated the change from a resting-state block to the following resting-state block which we refer to as RS-FCC.

The inventive technology was tested over multiple contexts to identify the relationship between stimulation and FCC. Characteristics of the stimulation protocol (protocol features) alone poorly predicted stimulation induced FCC, whereas the characteristics of the underlying network-level functional connectivity contained information which yielded accurate prediction of the FCC. This trend was true both when protocol features and network features were analyzed as groups and when features were analyzed individually. Protocol features may be understood as brain agnostic, because they are applied as an input irrespective of a particular networking that characterizes a given brain. The mappings from input features to FCC were similar between the stimulated-state and resting-state changes. Continuous stimulation modified the mapping from input features to resulting FCC. Our methods represent a promising new framework for parsing network-level FCC to predict the effects of stimulation, while the inventive technology can be deployed towards novel therapies of neural disorders.

The inventors observed that the network structure has a much stronger effect than the stimulation protocol (stimulation features) on the resulting FCC. The inventors also observe that the mappings from these input features to the FCC diverge over frequency bands and successive stimulations. Our approach represents a paradigm shift for targeted neural stimulation and can be used to interrogate, improve, and develop stimulation-based interventions for neural disorders.

DESCRIPTION OF THE DRAWINGS

The foregoing aspects and many of the attendant advantages of the inventive technology will become more readily appreciated as the same are understood with reference to the following detailed description, when taken in conjunction with the accompanying drawings, where.

DETAILED DESCRIPTION

In order to better understand the technical solutions of the present disclosure, the embodiments of the present disclosure are described in detail below with reference to the accompanying drawings. It should be clear that the described embodiments are only a part of the embodiments of the present disclosure, but not all of the embodiments. Based on the embodiments in the present disclosure, all other embodiments obtained by those of ordinary skill in the art fall within the protection scope of the present disclosure.

The terms used in the embodiments of the present disclosure are only for the purpose of describing specific embodiments, and are not intended to limit the present disclosure. As used in the embodiments of this application and the appended claims, the singular forms "a," "the," and "the" are intended to include the plural forms as well, unless the context clearly dictates otherwise.

It should be understood that the term "and/or" used in this document is only an association relationship to describe the associated objects, indicating that there can be three relationships, for example, A and/or B, which can indicate that A alone, A and B, and B alone. The character "/" in the present description generally indicates that the related objects are an "or" relationship.

It should be understood that although the terms 'first', 'second', and 'third' can be used in the present disclosure to describe thin film transistors, these thin film transistors should not be limited to these terms. These terms are used only to distinguish the thin film transistors from each other.

In the context of this disclosure, the terms "about," "approximately," "generally" and similar mean +/−5% of the stated value.

Figure 1:
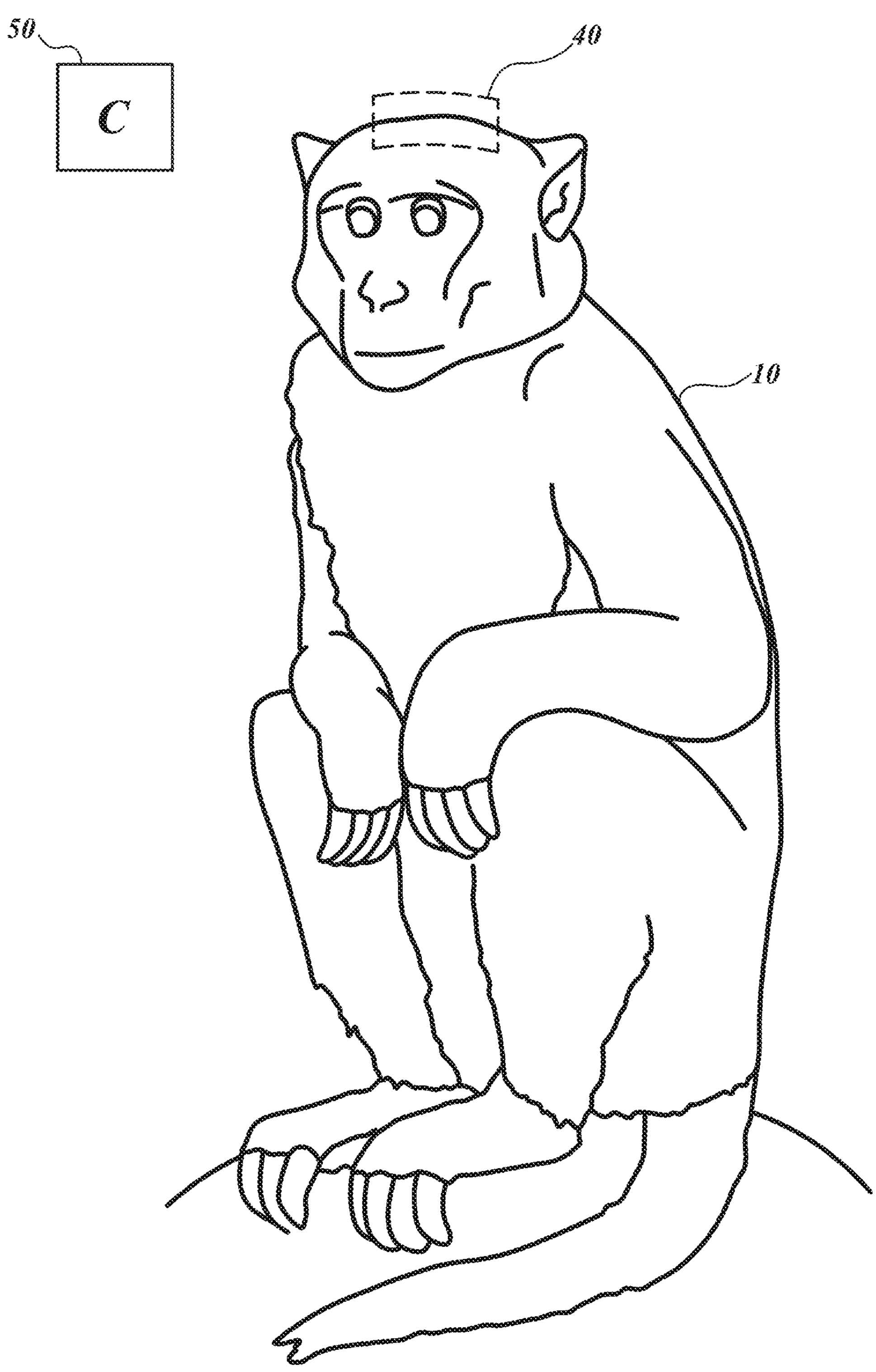
FIG. 1 is an illustration of a test animal with a cortical implant in accordance with an embodiment of the present technology.

FIG. 1 is an illustration of a test animal 10 with a cortical implant 40 in accordance with an embodiment of the present technology. The inventors performed a series of experimental sessions consisting of stimulating and recording rhesus macaque 10 cortex. In some embodiments, a controller (e.g., a computer) 50 is used to control experiment and/or to process the data.

Figure 2:
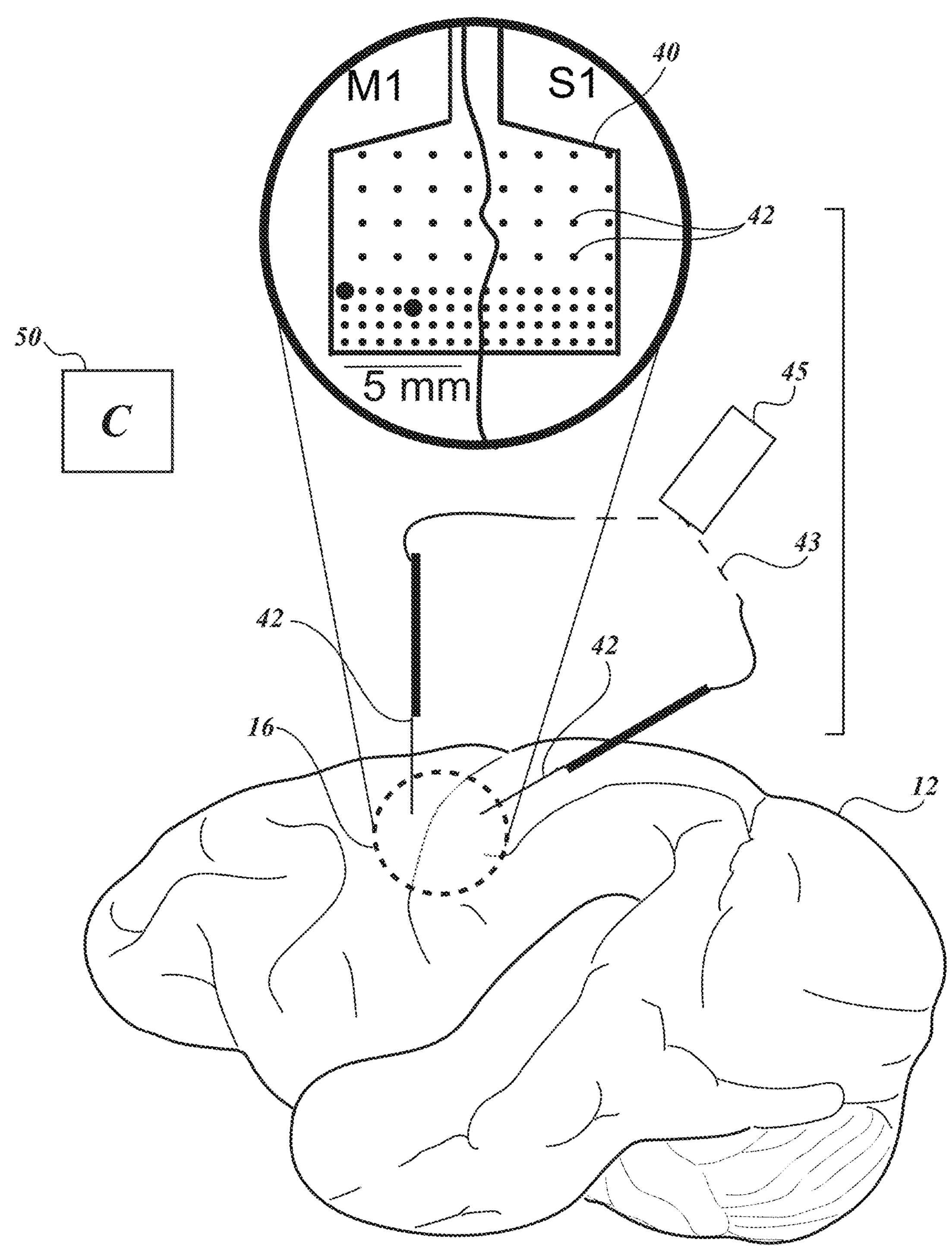
FIG. 2 is a diagram of the cortical implant in accordance with an embodiment of the present technology.

FIG. 2 is a diagram of the cortical implant 40 in accordance with an embodiment of the present technology. In some embodiments, the cortical implant 40 may be a transparent micro-electrocorticography array (μECoG) array. Optogenetic stimulation was used to stimulate neurons without causing a recording artifact. In some embodiments, a source of light 45 (e.g., a laser, a light emitting diode (LED), etc.) provides excitation signals through optical fibers 43 and further through transparent electrodes 42. In different embodiments, the electrodes 42 may made of metal and configured to deliver electrical stimulus to the target area of brain. In some embodiments, device 45 can represents a sensor capable of sensing activity of particular neurons as local-field potentials (LFP) through the electrodes 42.

FIG. 2 shows the transparent 96-electrode ECoG array 40 configured to record from macaque primary sensorimotor cortex. Also shown is the approximate location of the array on the cortex. Optogenetic stimulation was applied via laser light. We recorded traces of neural LFP during the resting-state and stimulation blocks making up our experimental sessions. During the stimulation blocks, stimulation was applied in a paired pulse protocol whereby the stimulation at the second site followed the first by a session-specific delay. Network coherences were constructed for each individual recording block by calculating pairwise LFP coherences over the network. Network coherence from resting-state recordings were parameterized to generate a set of network features. Details of the protocol was parameterized to generate a set of protocol features. The sets of network and protocol features were fed to a nonparametric model to predict network-wide FCC. Whereas the network features are linked to a particular brain, the protocol features may be brain agnostic, i.e., the protocol features may apply to a brain of any subject.

In some embodiments, the inventive technology operates to express the C1V1 opsin as it is a red-shifted excitatory opsin and thus allows for greater light penetration and subsequent neural activation C1V1. To record over a large-scale (~1 $cm^2$) area of the cortex 16 while allowing light to pass through the recording hardware, the inventors used a transparent ECoG array 40 which recorded local-field potentials (LFP) from the surface of the primary sensorimotor cortex.

For each experimental session two locations are randomly chosen corresponding to two electrodes 42 of the ECoG array to be stimulated. The stimulation consisted of alternating 5 ms laser pulses delivered by the laser 45 to the stimulation sites, temporally offset by a session-specific delay and repeated, for example, every 200 ms for 10 minutes. The session-specific delays were randomly chosen at the beginning of each experimental session to be 10 ms, 30 ms, or 100 ms. These values were chosen because session-specific delays of 10 ms and 30 ms have been shown to be in the effective range for connectivity change while 100 ms is outside the effective range. Locations of stimulation, the delay between the stimulation of the first and second sites, and the location and orientation of the ECoG array placement varied between experimental sessions, but were consistent over individual sessions.

The set of experimental sessions spanned multiple days and two rhesus macaques. The inventors recorded neural activity during 10-minute stimulation periods, which we refer to as "stimulation blocks," as well as during 5-minute periods before and after each stimulation period, which we refer to as "resting-state blocks." Each experimental session consisted of alternating resting-state (RS) blocks and stimulation state (SS) blocks, with 6 total resting-state blocks and 5 total stimulation blocks.

From the neural data recordings the inventors calculated the FCC for each pairwise connection between recorded electrodes of an experimental session. The inventors quantified FCC with the coherence metric for the Theta (4-7 Hz), Beta (12-30 Hz), Gamma (30-70 Hz), and High-gamma (70-200 Hz) bands.

As the effects of stimulation in both the stimulated-state and in the resting-state are relevant for neural disorders therapies, we estimate and model the FCC in both states. We calculated the change from a resting-state block to the following stimulation block which we refer to as SS-FCC, and calculated the change from a resting-state block to the following resting-state block which we refer to as RS-FCC.

Experimental Model and Subject Details

Two adult male rhesus macaques (monkey G: 8 years old, 17.5 Kg; monkey J: 7 years old, 16.5 Kg) were used in this study.

Method Details

Large-Scale Neural Interface

Stimulation and recording of the cortex were achieved using a large-scale optogenetic interface 40 (also referred to as a cortical implant 40) consisting of a semi-transparent micro-electrode array, semi-transparent artificial dura, titanium implant, widespread optogenetic expression, and laser-delivered optical stimulation. Neurons in the primary sensorimotor cortex were optogenetically photosensitized via viral-mediated expression of the C1V1 opsin. We injected a viral cocktail of AAV5-CamKIIa-C1V1(E122T/E162T)-TS-eYFP-WPRE-hGH ($2.5\times10^{12}$ virus molecules/ml; Penn Vector Core, University of Pennsylvania, PA, USA, Addgene number: 35499) in the primary sensory (S1) and primary motor (M1) cortices of the left hemisphere of the two rhesus macaques using the convection-enhanced delivery technique. We infused 200 L of the cocktail over four sites in monkey G and 250 L over five sites in monkey J.

The chronic neural interface was implanted by performing a 25 mm craniotomy over the primary sensorimotor cortices of the left hemisphere of two rhesus macaques, replacing the dura mater beneath the craniotomy with a chronic transparent artificial dura, and attaching a titanium cap over the craniotomy. During experiments we removed the artificial dura and placed a custom 92 $mm^2$ micro-electrocorticography array of 96 electrodes on the cortical surface for recording neural activity. The ECoG arrays consisted of platinum-gold-platinum electrodes and traces encapsulated in Parylene-C.

Neural data was recorded by sampling local-field potentials at 24 kHz from the ECoG array using a Tucker-Davis Technologies system (FL, USA). We stimulated the cortex by delivering light via a fiber optic (core/cladding diameter: 62.5/125 m, Fiber Systems, TX, USA) connected to a 488 nm laser (PhoxX 488-60, Omicron-Laserage, Germany) positioned above the array such that the tip of the fiber-optic cable touched the array. A 488 nm laser 45 was used it is close to the optimal wavelength of C1V1 activation.

Verification of Optogenetic Expression and Activation

We verified expression of the C1V1 opsin by fluorescent imaging of the eYFP marker, and by recording optogenetically-evoked neural responses. We observed widespread fluorescence in the primary sensorimotor cortices. We also observed neural activity elicited by illumination site, propagating within the stimulated anatomical region and across the central sulcus. We also verified that the evoked neural responses were due to optogenetic activation and not another light-induced factor such heating by illuminating outside the sites expressing fluorescence and recording neural activity. We found that such illumination did not evoke neural activity, confirming that the observed neural activation from our experimental sessions was due to optogenetic activation.

Structure of Experimental Sessions

Throughout each experimental session, subjects were watching cartoons while seated in a primate chair and headfixed. At the beginning of an experiment the chamber was opened, the artificial dura was removed, and the ECoG array was placed on the cortical surface. Throughout the experiment, the exposed cortex was irrigated with saline to ensure that it remained moist. At the end of each experiment, the ECoG array was removed from the cortical surface, the artificial dura was replaced on the brain, and the chamber was closed.

A total of 36 experimental sessions were performed over multiple days and two subjects. The experimental sessions consisted of recording while no stimulation took place, which we termed a "resting-state block" (RS block), and recording during stimulation, which we termed a "stimulation block" (SS block). Each resting-state block was 5 minutes long and each stimulation block was 10 minutes long. Each experimental session consisted of alternating resting-state blocks and stimulation blocks, with 6 total resting-state blocks and 5 total stimulation blocks, as a resting-state block was completed before the first and after the final stimulation block. The ECoG array was replaced on the cortex for each experimental session. Additionally, each recording block of an experimental session had the same stimulation protocol (i.e., stimulation protocol is treated as brain agnostic).

We stimulated two locations per experimental session which varied between experimental sessions but remained fixed throughout an experimental session. The locations were randomly chosen across the array. Optogenetic activation at the chosen stimulation site was verified before beginning the experimental session by stimulating and observing activation in the LFP traces. We ensured that these traces were due to neural activation and not photoelectric artifact by the method described in the "Signal preprocessing" section. We imaged the stimulation locations on the array and subsequently identified the closest recording electrode to each stimulation location. The distance from stimulation site to the nearest electrode was no more than 500 m.

We applied stimulation using a paired-pulse protocol of 5 ms pulses separated by a session-specific delay (FIG. 2). A pulse width of 5 ms was chosen because it elicited reliable responses in M1 and S1, and has a close duration to previously used targeted plasticity protocols. The session-specific delays were randomly chosen at the beginning of each experimental session to be 10 ms, 30 ms, or 100 ms; once chosen they remained fixed for an experimental session. It is believed that 10 ms and 30 ms delays induced reliable connectivity changes while 100 ms delays did not induce changes. The paired-pulses were repeated every 200 ms for the entirety of each stimulation block; this period was chosen to allow for enough time for the chosen delays while maximizing the number of paired-pulse stimulations within a conditioning block.

A total of four additional control sessions were performed over three days and two subjects. The structure of the sessions remained identical to the experimental sessions described in this section, except that no stimulation took place.

Signal Preprocessing

Before beginning an experimental session, we tested for photoelectric artifact. This was done by stimulating at frequencies faster than C1V1 off-kinetics (eg. 500 Hz) and examining the LFP traces. If this high frequency stimulation elicited response in the LFP traces then this was deemed to be photoelectric artifact, and the illumination site was moved to another location.

Before recording, electrode impedances were measured and those with high impedance were excluded from further analysis. We also examined the broadband recorded surface potentials and excluded those with low signal-to-noise ratio. The total amount of data removed constitutes no more than 15% of the raw time series. We then downsampled the data to 1 kHz after applying a low-pass Chebychev filter for anti-aliasing.

Signal Processing to Obtain a Time-Varying Coherence Network

Within each stimulation block and each resting-state block, the recorded LFP were partitioned into non-overlapping 20-second windows. All quantities computed from the raw LFP time series were computed on a per-window basis, then summarized across all windows in the block.

We computed an estimate of the coherence between all non-faulty electrodes for each 20-second window in every resting-state block and stimulation block. We denote by E the number of non-faulty electrodes and denote the multivariate LFP time series for a given window by the two-dimensional array $x_{1:T} \in \mathbb{R}^{E \times T}$, which consists of the time-ordered concatenation of the LFP recordings $x_t=(x_{1t}, x_{Et})^T$ for each electrode at time t. We estimated the multivariate spectral density function $S(\lambda) \in \mathbb{C}^{E \times E}$ for the time series $x_{1:T}$. The coherence between electrodes i and j at frequency $\lambda$ is denoted as $C_{ij}(\lambda)$ and computed from the estimated spectral density via $C_{ij}(\lambda)=|S_{ij}(\lambda)|^2/S_{ii}(\lambda)S_{jj}(\lambda)$. We computed the coherence at 403 linearly spaced frequencies in the interval (0,200) Hz.

Summaries over four frequency bands, 4-7 Hz (Theta), 12-30 Hz (Beta), 30-70 Hz (Gamma), and 70-199 Hz (High Gamma), were computed by averaging the coherence estimates within each band. Thus, for each session, the raw LFP time series was transformed into a sequence of matrix-valued quantities representing the average band-limited coherence in each 20-second interval. Since the coherence is symmetric and the diagonal conveys no information on pairwise behavior of the LFP electrode signals, we retained only values in the upper triangle above the diagonal for modeling and prediction.

We defined SS-FCC as the difference between the mean coherence of an electrode pair calculated during a stimulation block and the preceding resting-state block. We defined RS-FCC as the difference between the mean coherence of an electrode pair calculated during a resting-state block and the preceding resting-state block. We use FCC as a general term to refer to either SS-FCC or RS-FCC.

Let $$C_{ij}^{(w)}(\lambda_k)$$

be the coherence between electrodes i and j at frequency $\lambda_k$ in the 20-second window w, as estimated by the procedure described above. The band-limited coherence was obtained by averaging over the indices $k \in K_b$ corresponding to frequency band b:

$$C_{bij}^{(w)} = |K_b|^{-1} \sum_{k \in K_b} C_{bij}^{(w)}(\lambda_k).$$

Within an experimental session, we denote by $W_{R_\ell}, \ell \in \{1, 2,3,4,5,6\}$ and $W_{S_\ell}, \ell \in \{1,2,3,4,5\}$, the collections of 20-second windows belonging to resting-state block $\ell$ or stimulation block $\ell$, respectively. Note that the additional resting-state block corresponds to a final recording block after the 5th stimulation block. The electrode coherences were summarized for each of these blocks by their mean values:

$$\tilde{C}_{bij}^{(R_\ell)} = \frac{1}{|W_{R_\ell}|} \sum_{w \in W_{R_\ell}} C_{bij}^{(w)} \tag{1}$$

$$\tilde{C}_{bij}^{(S_\ell)} = \frac{1}{|W_{S_\ell}|} \sum_{w \in W_{S_\ell}} C_{bij}^{(w)} \tag{2}$$

The SS-FCC was then computed as $$y_{bij\ell} = \tilde{C}_{bij}^{(S_\ell)} - \tilde{C}_{bij}^{(R_\ell)} \tag{3}$$

and the RS-FCC was computed as $$y'_{bij\ell} = \tilde{C}_{bij}^{(R_{\ell+1})} - \tilde{C}_{bij}^{(R_\ell)}. \tag{4}$$

Nonlinear Modeling of Stimulation-Induced Coherence Change

We used a nonlinear additive model to explain the observed FCC in terms of features derived from both the experimental protocol and the information on functional connectivity available in the resting-state block prior to stimulation. In this framework, a single observation was denoted by the pair $(y_n, x_n)$, n=1, N, with $y_n \in \mathbb{R}$ an FCC measurement and $x_n \in \mathbb{R}^p$ the corresponding features. In switching to the single index n we indicate that the data was aggregated over all unique electrode pairs and all experimental blocks. The dependence on the band b was subsequently omitted for notational simplicity; the same analysis was repeated for the data in each frequency band. The FCC was modeled as $$y_n = \beta_0 + \sum_{j=1}^{p} f_j(x_{nj}) + \varepsilon_n. \tag{5}$$

The model consists of an intercept $\beta_0$, nonlinear functions $f_j$ controlling the impact of each feature j=1, . . . , p on the response, and an error term $\varepsilon_n$.

The utility of the model derives from the nonlinearity of the feature mappings and the additive procedure through which they are combined to yield a prediction for the FCC. The additive structure of the model allows for the visualization and interpretation of individual feature-response relationships. For each feature j=1, . . . , p, this is represented by the feature mapping $f_j$. Moreover, the predictive impact of feature j can be measured by the decrease in prediction error on a test set relative to a model in which the feature is omitted (or equivalently, a full model is estimated while enforcing $f_j$=0). The same analysis can be applied to groups of features. While additivity is essential for model investigation, the nonlinearity of the feature mappings enables the identification of more complex relationships than can be expressed in a linear model. Linearity is a strong modeling assumption that is both difficult to justify scientifically and, as demonstrated in the results, harmful in terms of predictive accuracy.

Feature Representation of Processed Data

A single observation of the FC corresponds to a unique pair of electrodes and a specific recording block. The corresponding features were constructed to satisfy two objectives: first, that the subsequent analysis separates the influence of the protocol parameters from that of the network structure of the functional connectivity; second, that all information in the features was available prior to stimulation.

To satisfy the first objective, the features were partitioned into two groups: "protocol features," which summarize aspects of the experimental setting and protocol; and "network features," which summarize information in the electrode coherences during baseline recording. The protocol features describe the parameters of the experimental framework. The designation "network features" derives from consideration of the estimated band-limited coherence as the adjacency matrix of an undirected, edge-weighted graph. The network features were intended to serve as simple but informative summaries of the connectivity information available in recordings of baseline activity prior to stimulation. They correspond to summary statistics computed over spatial or temporal ranges, basic quantities pertaining to the estimated spectrum brockwell, or network features that have found previous application in graph analysis. Finally, a subject-level indicator was included to adjust for potential global differences in FCC between the two macaque subjects. The adjustment is included in all models, as the subject is neither an aspect of the stimulation protocol nor a property of the baseline connectivity network.

Protocol Features

The protocol features were comprised of the categorical measurements Anatomical region, Delay, and Block number, as well as the real-valued features Distance, Stim1 distance to closer, Stim1 distance to further, Stim2 distance to closer, and Stim2 distance to further. Anatomical region indicates whether the two electrodes corresponding to a given measurement are both in region M1, both in region S1, or if one is in each region. Delay encodes three levels of time-delay in the pulse of the paired laser stimulation: 10, 30, or 100 ms. While the delay parameter in the stimulation protocol is real-valued, in the context of our data it is only measured at three distinct settings. We therefore chose to estimate an effect for each setting individually rather than to estimate a nonlinear function of the delay given observations at only three points. Block number indicates the time-order position of the experimental block in which the observation was recorded. In the "block analysis" regression design, we removed this feature and instead allowed all feature mappings to vary with the block number, thus investigating the predictive impact of allowing the entire model to evolve dynamically over the discrete time-stages of an experimental session. Distance measures the distance between the two electrodes, Stim1 distance to closer, Stim1 distance to further, Stim2 distance to closer, and Stim2 distance to further, encode distances between the stimulation sites and the closer and further electrodes of the electrode pair being predicted.

Network Features

The network features were computed from the LFP time series recorded during the resting-state block preceding the stimulation for which FCC are being predicted. Except for the Phase feature, all of these features were derived from the tensor obtained by time-concatenation of the coherence matrices across all windows in the resting-state block.

We introduce some tensor notation prior to defining these features. The coherence tensor for a given resting-state period is a three-dimensional array, denoted as $C \in \mathbb{R}^{E \times E \times T}$. Two-dimensional slices through the array at time t or electrode i are indicated as $C_{t\cdot\cdot}$ and $C_{\cdot i \cdot}$, respectively. One-dimensional vectors obtained by fixing an electrode i and a time point t are denoted $\vec{c}_{ti\cdot}$; vectors obtained by fixing both electrodes i and j are denoted $\vec{c}_{\cdot ij}$. The scalar coherence value at time t for electrodes i and j is denoted $c_{tij}$.

The Initial coherence indicates the mean coherence between electrodes i and j at baseline:

$$\frac{1}{T}\sum_{t=0}^{T} c_{tij} = \text{mean}\left(\vec{c}_{\cdot ij}\right) \tag{6}$$

The Coherence with network summarizes the average coherence between electrodes i and j and the remaining electrodes in the array. This corresponds to the normalized sum of vertex strengths of nodes i and j:

$$\frac{1}{T}\sum_{t=0}^{T} \frac{1}{E}\sum_{k=0}^{E} (c_{tik} + c_{tjk}) = \text{mean}\ (C_i + C_j) \tag{7}$$

The Coherence difference measures the mean absolute difference in coherence between electrodes i and j to other electrodes in the network:

$$\frac{1}{T}\sum_{t=0}^{T} \frac{1}{E}\sum_{k=0}^{E} |c_{tik} - c_{tjk}| \tag{8}$$

The Length-2 path strength represents the average strength of length-2 paths connecting electrodes i and j. This feature is similar to standard graph clustering coefficient metrics quantifying the total edge-weight of triangle motifs that include a given node. However, it excludes the direct edge between electrodes i and j, which reduces correlation with the initial coherence. Alternatively, the L=2 path strength can be considered the unnormalized cosine similarity between the network-coherence vectors of electrodes i and j:

$$\frac{1}{T}\sum_{t=0}^{T} \frac{1}{E}\sum_{k=0}^{E} c_{tik} c_{tjk} = \frac{1}{T}\sum_{t=0}^{T} \frac{1}{E}\left(\vec{c}_{ti\cdot}\right) \cdot \left(\vec{c}_{tj\cdot}\right) \tag{9}$$

The Coherence with stim sites is the average coherence between electrodes i and j to the two optogenetic stimulation sites. Below, the indices a and b refer to the electrode sites corresponding to the laser locations for a given experiment:

$$\frac{1}{4T}\sum_{t=0}^{T} (c_{tia} + c_{tib} + c_{tja} + c_{tjb}) \tag{10}$$

The Electrode covariance and Time covariance capture the variability of the coherence measurements over the electrode array and over the total number of 20-second time windows in a resting-state block, respectively.

The Electrode covariance represents a time-average of the covariance between the vectors representing the connectivity of electrodes i and j to the rest of the network:

$$\frac{1}{T}\sum_{t=0}^{T} \text{Cov}\left(\vec{c}_{ti\cdot}, \vec{c}_{tj\cdot}\right). \tag{11}$$

The Time covariance is the average across all other electrodes k of the covariance between the time series of coherence values to electrodes i and j:

$$\frac{1}{E}\sum_{k=0}^{E} \text{Cov}\left(\vec{c}_{\cdot ik}\vec{c}_{\cdot jk}\right). \tag{12}$$

Finally, the Phase was the only network feature not derived from the coherence tensor, since the coherence only contains magnitude information from the estimated spectral density. Writing the $(i,j)^{th}$ cross-spectral component computed within window w as:

$$S_{ij}^{(w)}(\lambda_k) = \left|S_{ij}^{(w)}(\lambda_k)\right| e^{i\theta_{ijk}^{(w)}}, \tag{13}$$

and denoting by $K_b$ the set of indices k such that $\lambda_k$ is in frequency band b, the phase feature $\theta_{ij}$ in block $\ell$ is given by:

$$\hat{\theta}_{ij}^{(B_\ell)} = \frac{1}{\left|W_{B_\ell}\right|}\sum_{w \in W_{B_\ell}} \frac{1}{|K_b|}\sum_{k \in K_b} \theta_{ijk}^{(w)} \tag{14}$$

Outlier Removal

Nonlinear regression methods are sensitive to extreme outliers, which can exert highly disproportionate influence on the model estimate. The goal was to achieve robustness against such outliers while minimizing perturbation of the data and subsequent analysis. Therefore we adopted a highly permissive definition, by which an observation was considered an outlier if its absolute deviation from the mean exceeded 20 times the interquartile range along any dimension (i.e. feature). Across all frequency bands and models, the maximum amount of data excluded by this procedure was less than 0.1% of the total number of observations.

Regression Designs

We investigated two different configurations of the regression design matrix within our nonlinear modeling framework. For each design, the data were aggregated across all of the experimental sessions for each subject. While significant session heterogeneity suggested that even stronger prediction results were possible for models fit to individual sessions, our objective was to estimate a model that generalized well in the sense of accurate prediction on data from many sessions.

Full Data

First we investigated the performance of the nonlinear model on the full data, which included all experimental blocks from all sessions of both subjects. This yielded N=481,505 observations of p=16 features, which expanded to dimension 21 after dummy-coding of the categorical variables Delay, Region, and Block number, and to dimension 22 after inclusion of the categorical animal subject indicator.

Block Interactions

Under the full data design, the time evolution of the response was limited to global shifts corresponding to the categorical feature Block number. We subsequently investigated the impact of allowing the shape of the feature mappings to vary with the block number, thus expanding the model's capacity to capture time variation in feature-response relationships over the course of repeated stimulation. This constituted an interaction design, whereby the categorical feature Block number was removed, and the remaining features were each augmented with interaction terms for binary indicators that denoted whether the measurement was made in each of blocks 2, 3, 4, and 5. The number of observations remained N=481,505, while the number of features expanded to p=94.

Estimation of the Nonlinear Additive Model

We used a train-test paradigm to assess the predictive performance of the nonlinear model on unseen data. For each frequency band and regression design, the data were split uniformly at random such that 70% of the observations were assigned to the training set and the remaining 30% were assigned to the test set. All model parameters and hyperparameters were selected using data from the training set only. Prior to estimation of the model parameters, the real-valued features were standardized such that they have mean zero and unit standard deviation. Whenever the data were split between train and test sets, the parameters of the linear transformation corresponding to standardization were computed from the training data and applied to the test data.

The nonlinear feature mappings $f_j$, j=1, . . . , p, in Eq. (5) were represented in the basis of polynomial functions:

$$f_j(x) = \beta_{j1}x + \beta_{j2}x^2 + \cdots + \beta_{jK}x^K. \tag{15}$$

The complete set of parameters to be estimated was thus $\beta=(\beta_0, \beta_1, \ldots, \beta_p)$, where $\beta_j=(\beta_{j1}, \ldots, \beta_{jK})^T \in \mathbb{R}^K$. The order of the polynomial representation for $f_j$ is defined as the maximum integer value $k \in 1, \ldots, K$ for which $\beta_{jk}$ is nonzero. The smoothness of $f_j$ is determined by the order k of its polynomial representation and the magnitude of the coefficients $\beta_{j1}, \ldots, \beta_{jk}$. Numerical implementation requires the specification of an upper bound K, corresponding to truncation of the infinite basis at some maximum order. We used K=10 in all experiments; this decision was justified by the fact that the parameter estimates decay either to negligible values or to exactly zero before reaching order K≤10, as a result of the hierarchical penalization of the model coefficients.

All categorical features were dummy-coded such that the C categories for each feature are represented by C−1 indicator variables. Polynomial expansion of these variables generates identical columns and thus rank-deficiency in the design matrix, which leads to instability in the optimization routine. This problem was avoided by truncating the polynomial expansion of all categorical variables to order 1 rather than order K. There is no resulting loss of generality from this truncation. Rather, this expanded the framework to allow for simultaneous estimation of smooth nonlinear functions of continuous features and discrete functions (that can be visualized for example, as a step function) of categorical features.

Automatic Order Selection Via Hierarchically Penalized Estimation

Given an observation of the features x, the model prediction of the SS-FCC or RS-FCC is given by:

$$\hat{f}(x) = \beta_0 + \sum_{j=1}^{p} f_j(x_j). \tag{16}$$

We used the standard square loss on the training set $D^{train}$ $$\mathcal{L}(\beta) = \frac{1}{|D^{train}|}\sum_{(x,y)\in D^{train}} \left(y - \hat{f}(x)\right)^2 \tag{17}$$

as the model goodness-of-fit criterion. Direct optimization of model fit on a training set over a sufficiently complex model class is well-known to yield estimates that perform poorly on unseen data, an issue commonly known as overfitting. We avoided this problem by adoption of a penalized estimation framework specifically designed to control the magnitude of the parameter estimates and automatically select the order of each feature mapping in the model. This approach augments the standard square loss with a penalty term $\Omega_j(\beta_j; \alpha, \lambda)$ for each feature j, defined as:

$$\Omega_j(\beta_j; \alpha, \lambda) = \alpha\lambda\sum_{k=1}^{K} w_k\left(\sum_{i=1}^{N}\left(\beta_{jk}x_{ij}^k\right)^2 + \ldots + \left(\beta_{jK}x_{ij}^K\right)^2\right)^{\frac{1}{2}} + (1-\alpha)\lambda\left(\sum_{i=1}^{N}(\beta_{j1}x_{ij})^2 + \ldots + \left(\beta_{jK}x_{ij}^K\right)^2\right)^{\frac{1}{2}}, \tag{18}$$

with hyperparameters $\lambda \in \mathbb{R}_+$ and $\alpha \in [0,1]$. The weights $w_k=k^3-(k-1)^3$ were chosen to satisfy theoretical criteria that guarantee statistical convergence of the estimator over a class of smooth functions.

The model parameters were estimated by solving:

$$\hat{\beta} = argmin_{\beta}\mathcal{L}(\beta) + \Sigma_{j=1}^{p}\Omega_j(\beta_j; a, \lambda). \tag{19}$$

We used a block coordinate descent algorithm as implemented in the R package.

The first term in the penalty $\Omega_j(\beta_j; \lambda, \alpha)$ induces hierarchical sparsity in the estimate of $\beta_j=(\beta_{j1}, \ldots, \beta_{jK})^T$, while the second term shrinks the magnitudes of the estimated coefficients towards zero. Hierarchical sparsity guarantees that if an estimated coefficient $\hat{\beta}_{jk}=0$, then all higher-order coefficients for that feature $\hat{\beta}_{jk'}=0$, with k<k'≤K; this is equivalent to selecting an order k−1 representation for the feature mapping $f_j$. The selection procedure is thus automatic and data-driven in that it emerges as a direct mathematical consequence of the penalized estimation framework, which seeks the best model fit to the data under the structural constraints imposed by $\Omega_j(\beta)$.

Cross-Validation for Model Hyperparameters

The penalized loss function requires specification of two regularization hyperparameters $\lambda \in \mathbb{R}_+$ and $\alpha \in [0,1]$, which control the overall regularization strength and tradeoff between terms inducing hierarchical and feature-wise sparsity, respectively. The parameter α was selected over the range from 0 to 1, inclusive, in increments of 0.1. The parameter λ was selected over 100 log-linearly-spaced values between $\lambda_{max}$ and $\lambda_{max}\times10^{-5}$.

The value $\lambda_{max}$ was selected such that all estimated feature mappings are equal to zero for every value of investigated α; it was obtained by a backtracking line search algorithm. This algorithm requires a gross upper bound $\lambda_0$, defined as any value of λ>0 such that $\hat{\beta}=0$ for all grid values of α. It was found manually; we found that $\lambda_0=0.1$ sufficed for all designs and frequency bands.

We selected the pair (α*, λ*) by first finding the (α, λ) pair minimizing the average $R^2$ on the validation set over 5-fold cross-validation on the training data. We selected α* as the α-coordinate of this pair, and selected λ* as the largest value of λ such that the mean validation $R^2$ of (α*, λ) was within one standard error of the mean validation $R^2$ at (α*, λ*). This follows the "one standard error" strategy for one-dimensional cross-validation esl and represents a conservative approach to regularization corresponding to our preference for smoother feature mapping estimates.

Performance Measure

We quantified model performance by predictive accuracy on the test set, as measured by the coefficient of determination, $$R^2 = 1 - \frac{\sum_{i=1}^{n_{test}} (y_i - \hat{y}_i)^2}{\sum_{i=1}^{n_{test}} (y_i - \bar{y}_i)^2}, \tag{20}$$

where $\hat{y}_i$ was the model prediction after cross-validation and estimation on the training set and $\bar{y}_i$ was the mean of the regression target on the test set.

Resampling for Feature Stability

We took a resampling approach to assess the stability of the estimated feature mappings of the nonlinear model. Following the subsampling heuristic approach, we drew a subsample of size ⌊N/2⌋ from the data without replacement and ran the full estimation procedure, including hyperparameter selection, on the subsampled data. The procedure was repeated for 100 independent trials, resulting in 100 estimated functions for each feature. The feature-wise variability in the nonlinear additive feature mappings was then assessed pointwise, by computing upper and lower quantiles for the range of function values at each point in a fine grid.

A Predictive Measure of Feature Importance

Traditional tests of statistical significance are not available for the coefficients of the nonlinear additive model as the asymptotic distribution of the penalized estimator is not known. Instead, we assessed importance of a feature or group of features by evaluating the difference in predictive performance on the test set between the full model and a model fit without the parameter or parameter group of interest. Removing the feature or feature group is equivalent to estimating the full model under the constraint that their corresponding parameters are all equal to zero. The comparison can thus be viewed as between the full model and one in which a hypothesis of null response is enforced for the feature or group of interest.

Quantifying feature importance via the step-down procedure accounts for the fact that the explanatory power of the feature of interest may partially overlap with other included features. We are thus asking, "what is the marginal explanatory power of this feature, beyond what could be explained by the remaining features in the model?" In the context of our work, this is used to understand, for example, whether the network features provide any additional information over the protocol features. A step-up procedure could not answer such a question.

When estimating the reduced model, we used the regularization parameters (α*, λ*) obtained by cross-validation on the full data.

Quantifying Feature Similarity Across Frequency Bands

Let $$\hat{f}_j^a \text{ and } \hat{f}_j^b$$

be the estimated feature mappings for feature j on the data corresponding to frequency bands a and b, respectively. We computed a quantitative measure of their similarity, $$s_j^{ab} = \frac{\langle f_j^a, f_j^b \rangle}{\|f_j^a\| \|f_j^b\|}. \tag{21}$$

The quantity $$s_j^{ab}$$

is the cosine similarity of the estimated feature mappings, considered as elements of a common Hilbert space of functions. By definition, $$s_j^{ab} \in [-1, 1].$$

Similarity increases as $$s_j^{ab}$$

approaches 1 or −1 (which indicates $$f_j^a \text{ and } -f_j^b$$

are perfectly similar) and is minimized at 0.

The inner product $$\langle f_j^a, f_j^b \rangle = \int_{x_j} f_j^a(x) f_j^b(x) dx$$

and norm $\|f_j\| = \langle f_j, f_j \rangle$ are given by integrals whose domain $X_j$ depends on the feature j. For real-valued features, we took $X_j$ to be the interval [−5,5], which after standardization corresponds to the range of all observed measurements within 5 standard deviations of the mean. Due to the polynomial representation of the nonlinear feature mappings, these could be computed exactly.

Quantification and Statistical Analysis

Statistical significance of the prediction of RS-FCC between stimulation sites from the stimulation delay was calculated using one-sided F-test with 165 observations and 2 degrees of freedom. Statistical significance of the SS-FCC of stimulation (N=481,505 pairwise observed SS-FCC) versus control (N=67,510 pairwise observed SS-FCC) condition was calculated using Welch's unequal variances t-test. These tests were performed in Python 3 using the SciPy package. The resampling procedure described in the section "Resampling for feature stability" was performed in R.

Stimulation Delay as a Poor Predictor of Resting-State Functional Connectivity Change Between Stimulation Sites Studies have shown that change in anatomical connectivity between two monosynaptically connected neurons is a function of activation times, or stimulation delay, between the neurons, a phenomenon termed STDP. As STDP relates delay to structural changes in connectivity but not real-time modulation of neural activity, the inventors evaluated how well stimulation delay could predict RS-FCC between the sites of stimulation.

Figure 4A:
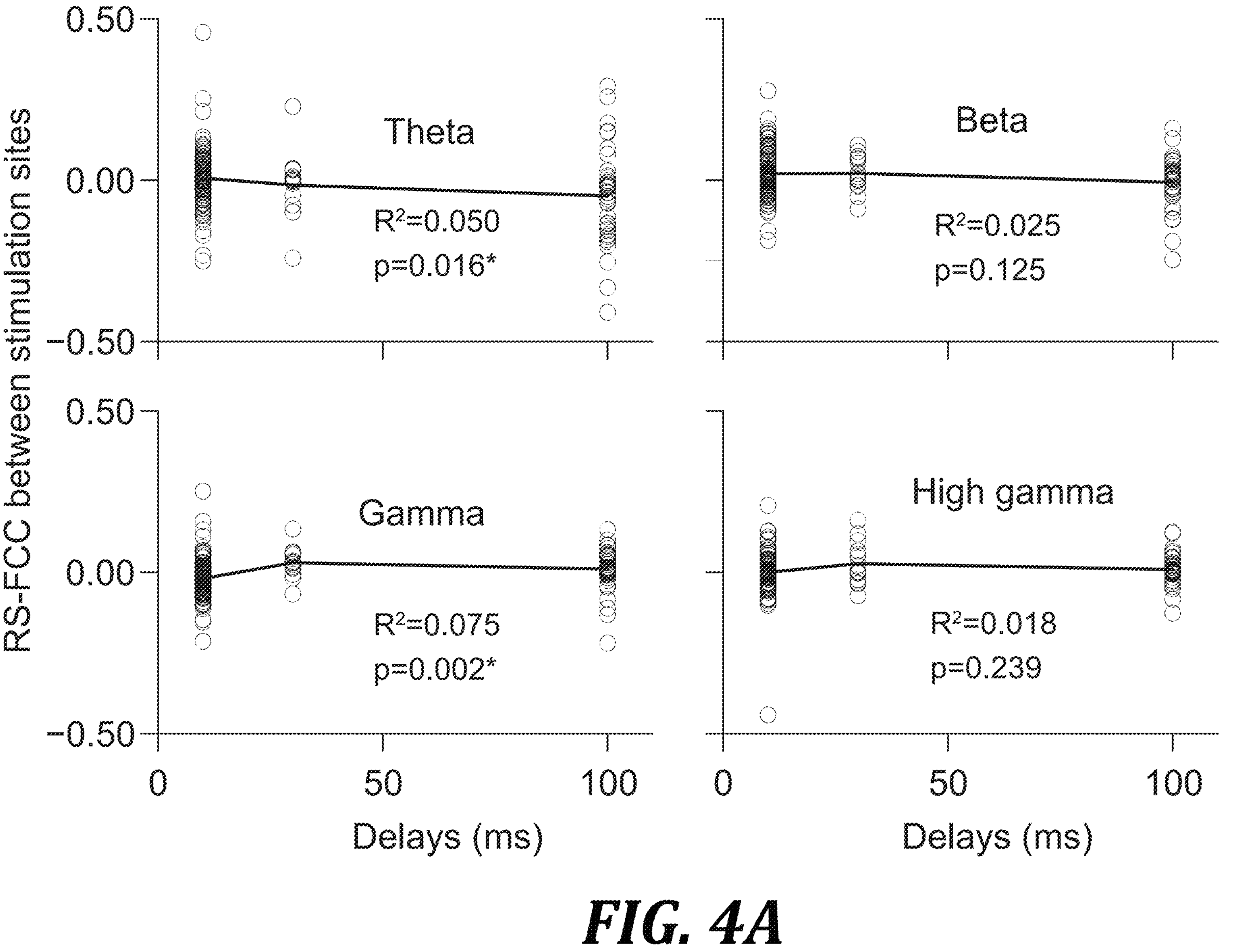
FIG. 4A is a graph of delay-based prediction of RS-FCC between stimulation sites in accordance with an embodiment of the present technology.

The standard function relating stimulation delay to corresponding connectivity change according to the STDP hypothesis is an exponential function. However, the inventive experimental setting bears little resemblance to the controlled monosynaptic studies yielding such a curve. As such, the inventors did not enforce an exponential delay function but rather tested whether varying the delay had an effect on RS-FCC by fitting a linear model with delay as categorical input and RS-FCC as continuous output (FIG. 4A). Since STDP is a process governing pairwise connectivity change, the inventors modeled only RS-FCC calculated between stimulation sites, and did not model RS-FCC nor connectivity between unstimulated sites. We observed that delay was a significant predictor of RS-FCC in Theta and Gamma bands, but not for Beta or High-gamma (p: Theta 0.016, Beta 0.125, Gamma 0.002, High-gamma 0.239; one-sided F-test with 165 observations, 2 degrees of freedom). For all frequencies the inventors observed that delay had low explanatory power ($R^2$: Theta 0.050, Beta 0.025, Gamma 0.075, High-gamma 0.018). These results indicate that, although a naive extrapolation of the STDP curve to our large-scale setting would hint otherwise, delay between paired stimulation of two neural sites minimally controls RS-FCC.

Pairwise Stimulation Drives Functional Connectivity Changes in the Stimulated-State and Resting-State Across the Entire Recorded Network In order to determine whether our stimulation induced FCC only between the stimulation sites or over a broader area of the recorded network, the inventors examined the network-wide FCC. We plot an example network of FCC over our recording array in FIG. 2*b*. In this example, the inventors found that the connectivity change between stimulation sites (bolded) is simply one change among many in the recorded network. To quantify the network-wide FCC over all experiments the inventors calculated the FCC distributions. We observed that stimulation generally increased network-level functional connectivity, as SS-FCC had positive mean over all frequency bands. We additionally compared the SS-FCC of our stimulation experiments to a set of control experiments in which no stimulation was applied, and found that stimulation resulted in significantly higher SS-FCC ($p<0.0001$ in all frequency bands; Welch's unequal variances t-test).

We then compared the SS-FCC and RS-FCC distributions. We found SS-FCC was highly correlated to RS-FCC, as the Pearson's correlation coefficient was above 0.6 in all frequency bands. The means of RS-FCC distributions were less offset from 0 than the means of SS-FCC distributions of the same frequency bands, and variances were similar between RS-FCC and SS-FCC distributions of the same frequency bands. These widespread FCC raise the question of explaining and predicting the stimulation-induced FCC across the entirety of the recorded network.

Nonlinear Modeling to Predict Stimulation-Induced Network-Wide Functional Connectivity Changes Motivated by the observation of network-wide FCC, the inventors pursued an accurate and interpretable model to predict FCC over the entire recorded network. While linear modeling is the standard method for statistically rigorous interpretable models, the assumption of linearity is scientifically unreasonable for statistical relationships among complex experimental measurements such as neural data esl. We relax this assumption through the use of a nonparametric hierarchical additive model which can identify complex nonlinear input-output relationships harisHier. As this model retains the structure of summation over individual features familiar from linear modeling, it permits feature-wise investigation of the results. In addition, careful penalization of the estimation objective ensures that the model retains relevant theoretical guarantees and is encouraged to learn simple, smooth components harisHier. In the following sections the inventors use such nonparametric hierarchical models to arrive at our results. These models outperformed linear models uniformly across frequency bands and prediction tasks.

Figure 3:
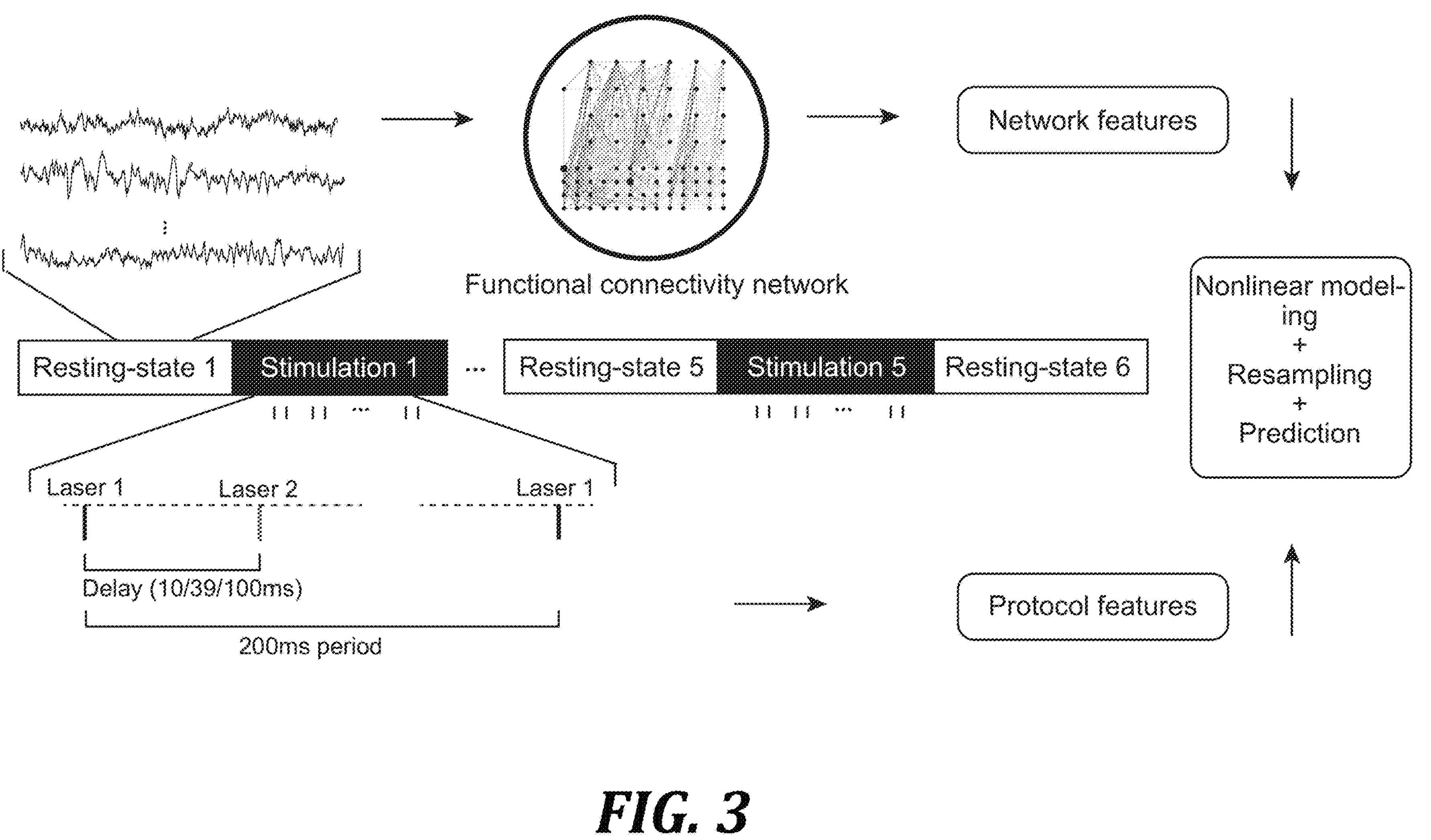
FIG. 3 is a schematic diagram of network features and protocol features in accordance with an embodiment of the present technology.

FIG. 3 is a schematic diagram of network features and protocol features in accordance with an embodiment of the present technology. We recorded traces of neural LFP during the resting-state and stimulation blocks making up our experimental sessions. During the stimulation blocks, stimulation was applied in a paired pulse protocol whereby the stimulation at the second site followed the first by a session-specific delay. Network coherences were constructed for each individual recording block by calculating pairwise LFP coherences over the network. Network coherence from resting-state recordings were parameterized to generate a set of network features. Details of the protocol were parameterized to generate a set of protocol features. The sets of network and protocol features were fed to a nonparametric model to predict network-wide FCC.

Figure 4B:
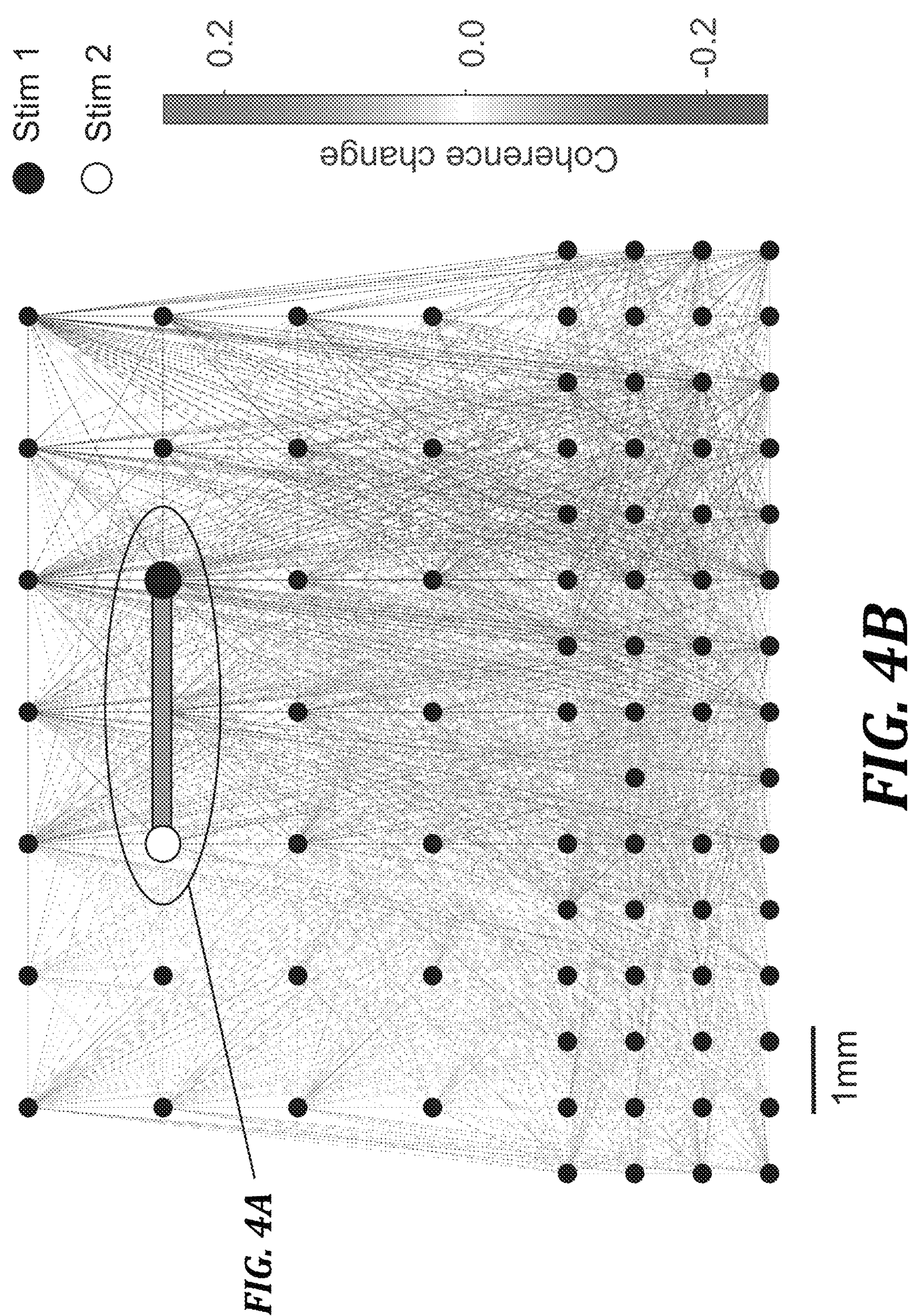
FIG. 4B is a visualization graph of RS-FCC in accordance with an embodiment of the present technology.

FIG. 4A is a graph of delay-based prediction of RS-FCC between stimulation sites in accordance with an embodiment of the present technology. FIG. 4A illustrates delay-based prediction of RS-FCC between stimulation sites has poor explanatory power, and does not achieve statistical significance in the Beta and High-gamma FIG. 4B is a visualization graph of RS-FCC in accordance with an embodiment of the present technology. Visualization of the RS-FCC of a single example session over the μECoG array. Black circles correspond to electrodes while the edges indicate the change in coherence relative to the preceding baseline period. Optogenetic stimulation sites are indicated by light blue circles. The bolded line connecting the stimulation sites indicates the coherence change between the two sites.

Figure 4C:
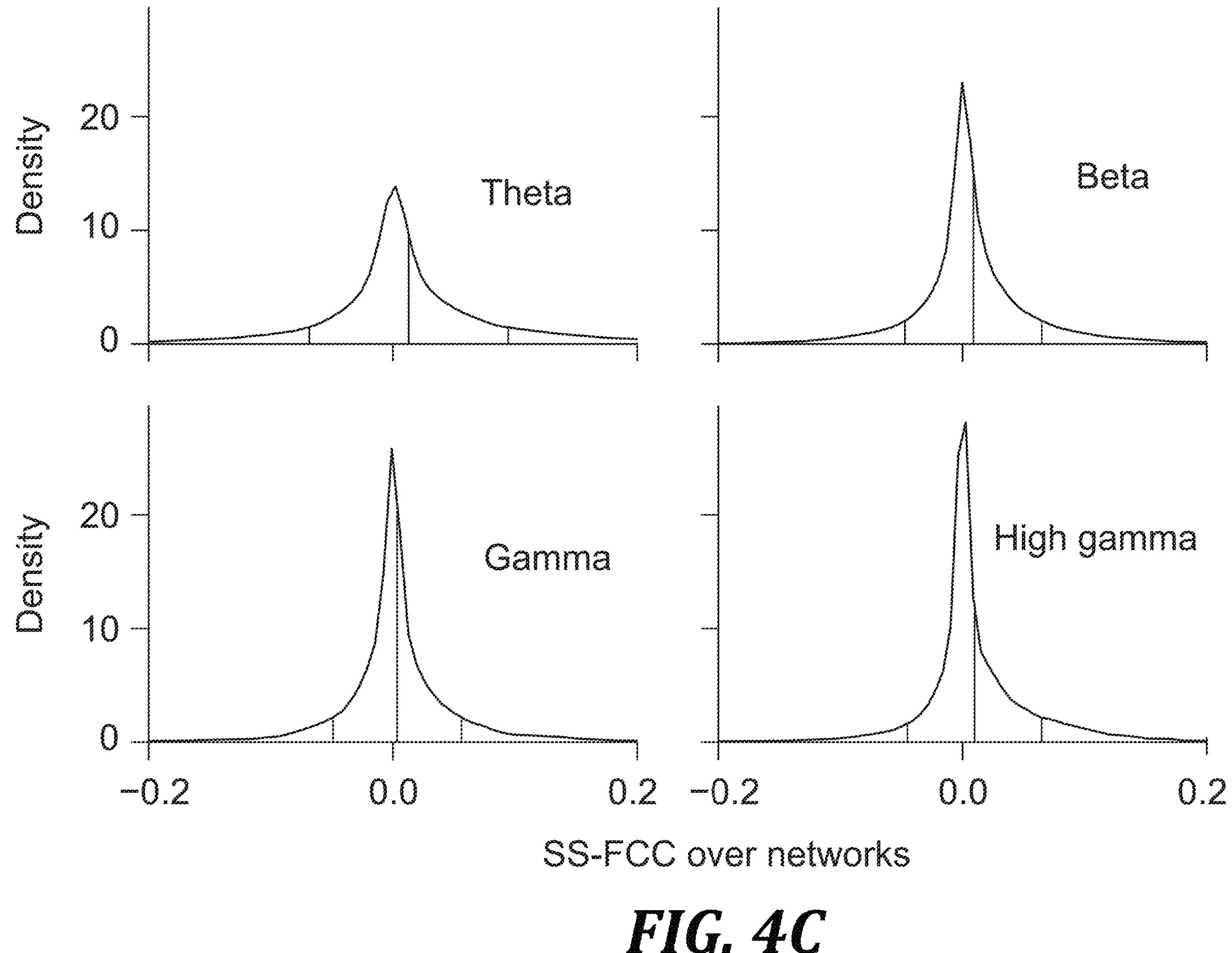
FIG. 4C is a distribution of SS-FCC in each frequency band in accordance with an embodiment of the present technology.

FIG. 4C is a distribution of SS-FCC in each frequency band in accordance with an embodiment of the present technology. Distribution of the SS-FCC in each frequency band over all sessions. Internal lines indicate the mean, and one standard deviation below and above the mean.

Figure 4D:
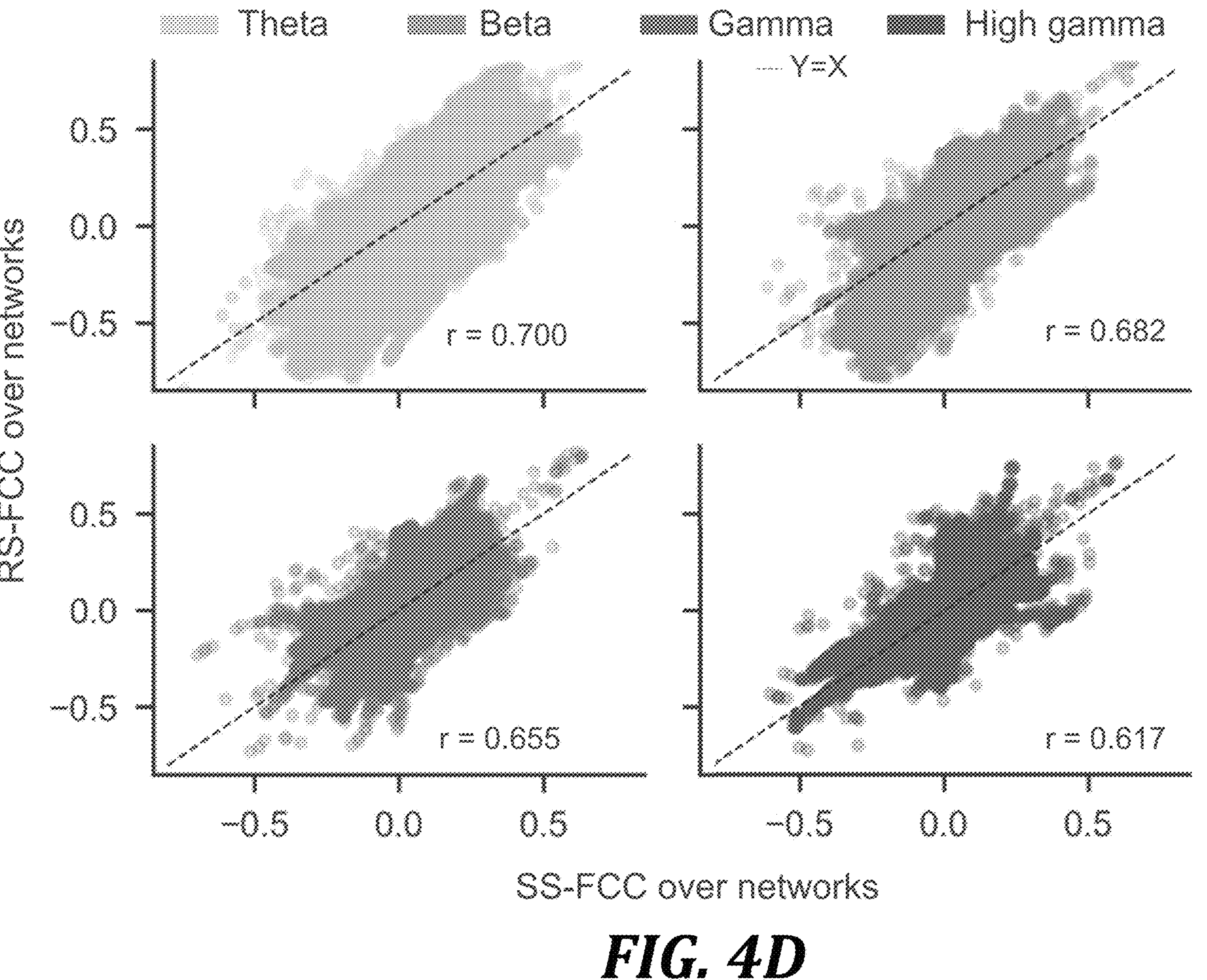
FIG. 4D is a scatter plot of SS-FCC versus RS-FCC in accordance with an embodiment of the present technology.

FIG. 4D is a scatter plot of SS-FCC versus RS-FCC in accordance with an embodiment of the present technology. Scatter plot of SS-FCC versus RS-FCC shows high correlation.

The Stimulation Protocol Alone is a Poor Predictor of Network-Wide Functional Connectivity Changes To test the degree to which the factors of the stimulation protocol controlled the network-wide FCC, the inventors constructed models to predict SS-FCC and RS-FCC from the stimulation protocol. We constructed a set of 8 features consisting of: stimulation delay, a categorical identifier of the time ordering of the stimulation block, the distance between a given electrode pair, the distances from the sites of stimulation to the closer or further electrode of an electrode pair, anatomical region of electrodes (FIG. 5A) (see Methods for more details of how they are calculated). Throughout the paper the inventors refer to this set of predictive features as "protocol features." We also include a categorical animal subject indicator in the model in order to capture differences in mean between the two subjects. With this feature set the inventors trained models with output of pairwise FCC between all recording electrodes of an experiment, over each block of all experiments. We fit individual models to predict SS-FCC or RS-FCC over individual frequency bands. We held out 30% of the data to evaluate the predictive performance of the model on unseen data.

We observed that the protocol-based model of FCC had low predictive power for both SS-FCC ($R^2$: Theta 0.045, Beta 0.026, Gamma 0.057, High-gamma 0.078) and RS-FCC ($R^2$: Theta 0.028, Beta 0.014, Gamma 0.020, High-gamma 0.014). These results indicate that while factors related to the protocol alone explain some of the variation in the observed coherence change, they are insufficient to generate practically relevant predictions.

Figure 5A:
FIG. 5A is a visualization graph of protocol features in accordance with an embodiment of the present technology.
Figure 5A:
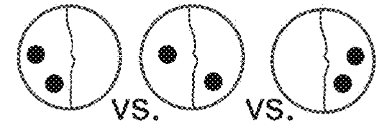
Figure 5A:
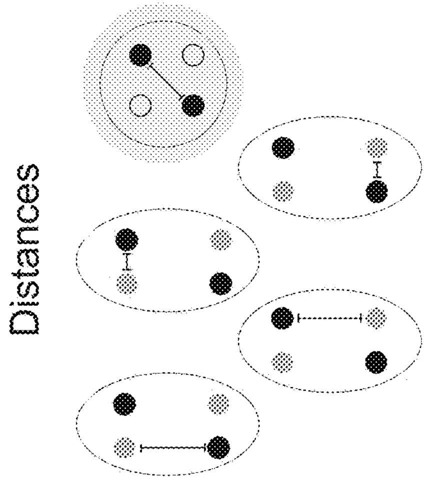

FIG. 5A is a visualization graph of protocol features in accordance with an embodiment of the present technology. Visualization corresponds to the protocol features. From top to bottom, the features are: stimulation delay, anatomical region, block number, distance, stim 1 distance to closer, stim 2 distance to closer, stim 1 distance to further, stim 2 distance to further.

Figure 5B:
FIG. 5B is a visualization graph of network characteristics in accordance with an embodiment of the present technology.
Figure 5B:
Figure 5B:
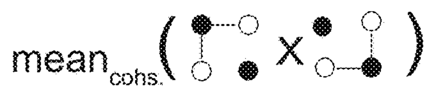
Figure 5B:
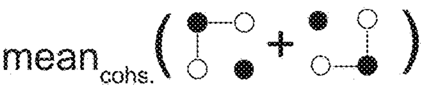
Figure 5B:
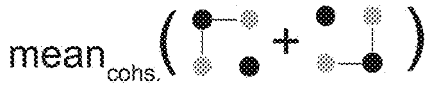
Figure 5B:
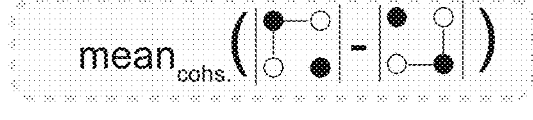
Figure 5B:
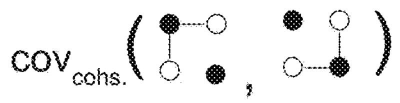
Figure 5B:
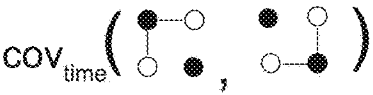

FIG. 5B is a visualization graph of network characteristics in accordance with an embodiment of the present technology. Visualization corresponds to the network characteristics which the network features quantify. From top to bottom, the visualizations correspond to: initial coherence, phase, length 2 path strength, coherence with network, coherence with stim sites, coherence difference, electrode covariance, and time covariance.

Figure 5C:
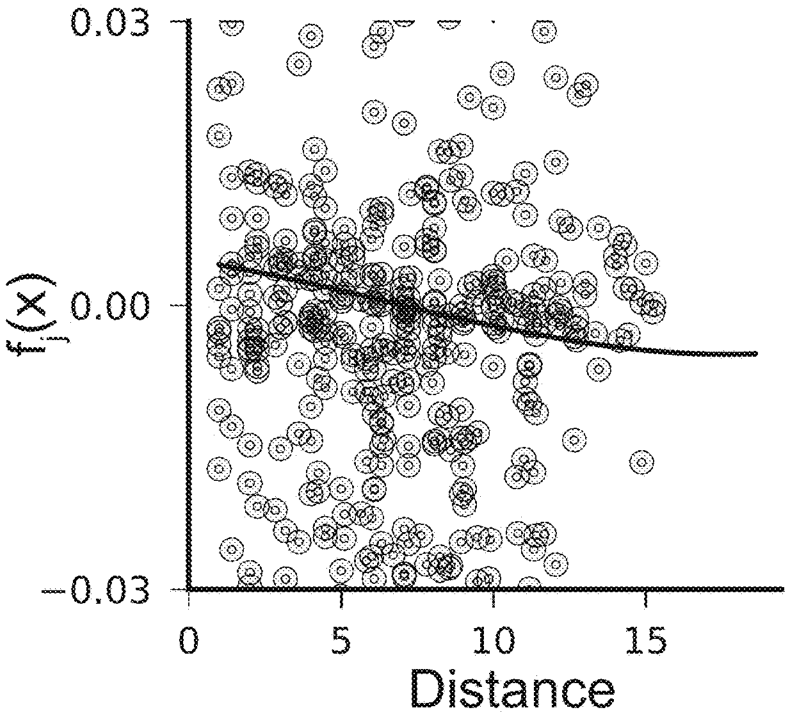
FIG. 5C is a graph of near-linear fits in accordance with an embodiment of the present technology.

FIG. 5C is a graph of near-linear fits in accordance with an embodiment of the present technology. The nonparametric model can identify feature mappings of a variety of complexities, such as near-linear fits such as that found for the distance feature.

Figure 5D:
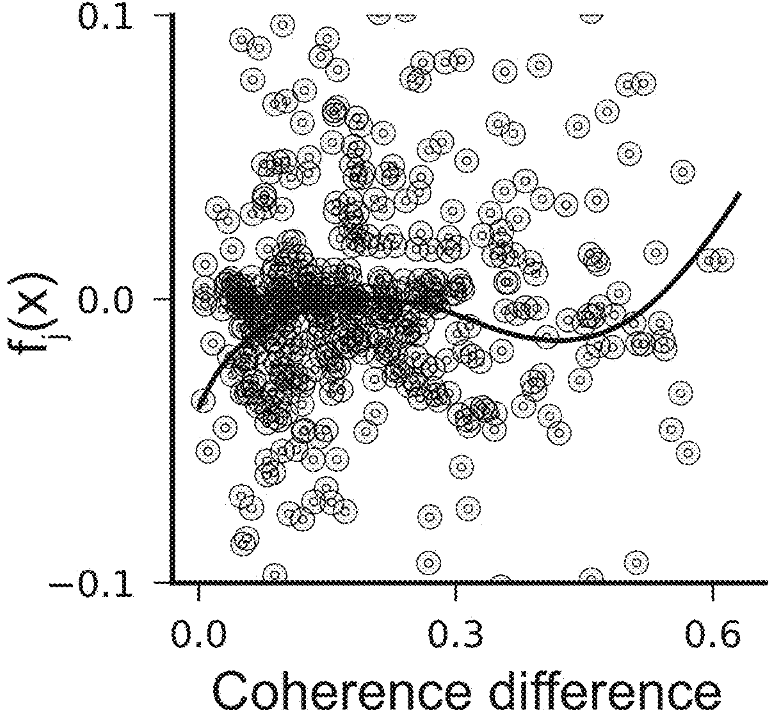
FIG. 5D is a graph of higher-order polynomials for connectivity difference feature in accordance with an embodiment of the present technology.

FIG. 5D is a graph of higher-order polynomials for connectivity difference feature in accordance with an embodiment of the present technology. The nonparametric model can identify feature mappings of a variety of complexities, such as higher-order polynomials such as that found for the connectivity difference feature. fj (x) indicates the contribution of a feature to the predicted FCC. Throughout the figure, the gray shadowing indicates the distance feature, while the light blue shadowing indicates the connectivity difference feature.

Figure 5E:
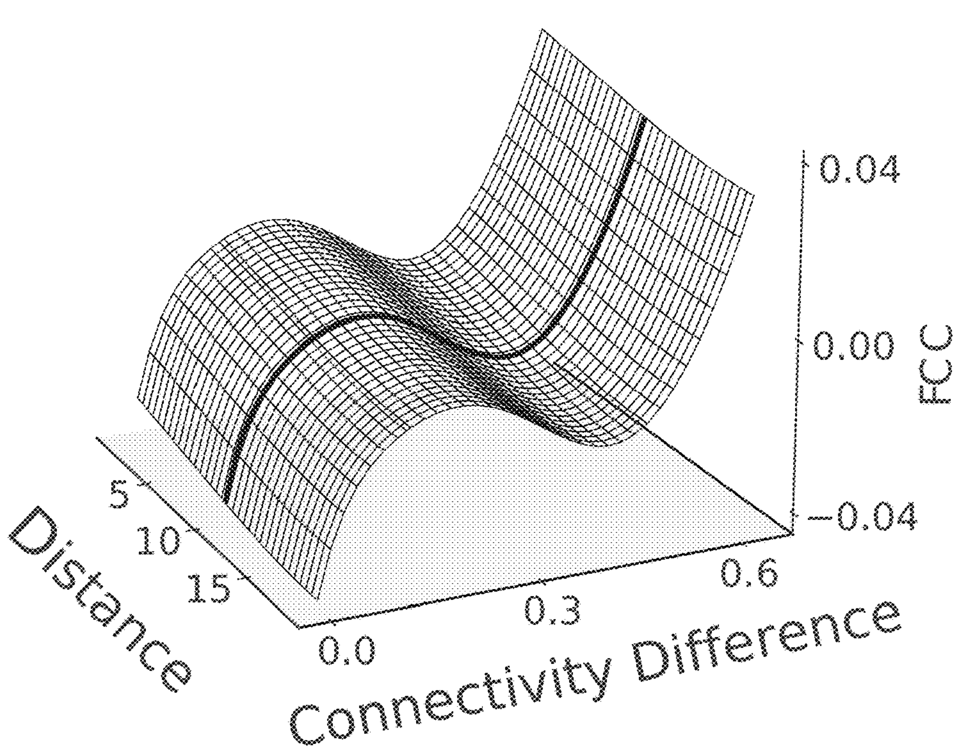
FIG. 5E is a graph of feature mappings that are additively combined in accordance with an embodiment of the present technology.

FIG. 5E is a graph of feature mappings that are additively combined in accordance with an embodiment of the present technology. An example is shown as how the feature mappings are additively combined.

Figure 5F:
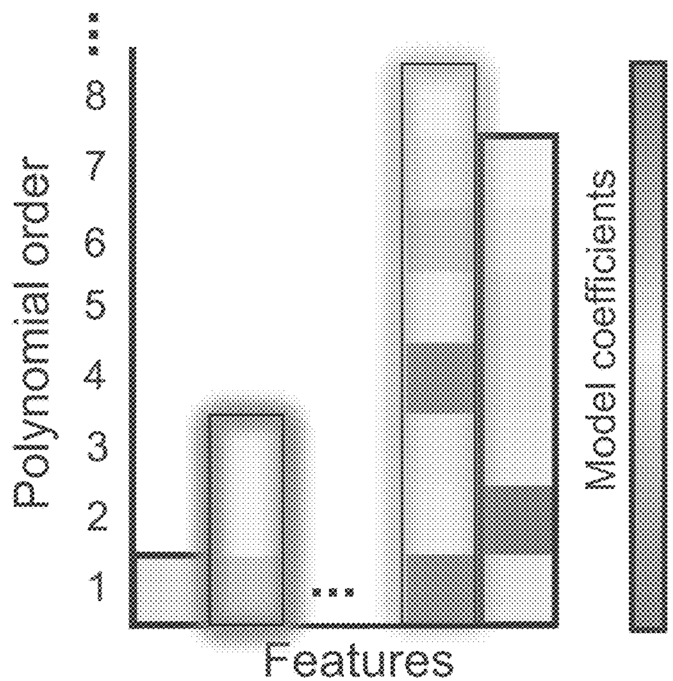
FIG. 5F is a graph of feature mappings based on complex nonlinear functions in accordance with an embodiment of the present technology.

FIG. 5F is a graph of feature mappings based on complex nonlinear functions in accordance with an embodiment of the present technology. Individual feature mappings are represented in a basis of increasingly complex nonlinear functions. The order of this representation is selected automatically by a penalized estimation procedure, with the y-axis of this figure indicating the polynomial order. The order selection for the distance feature and connectivity difference feature are shadowed in gray and light blue, respectively.

Network Structure Determines Stimulated-State and Resting-State Functional Connectivity Changes Our observations that stimulation induces a change in connectivity over an entire network, in tandem with the poor predictive power of the protocol-based model, lead us to expect that the effects of stimulation may be mediated by the existing cortical network. We tested this expectation by constructing a set of 8 features extracted from the baseline functional connectivity network. These features are: initial coherence, which is the pairwise coherence between an electrode pair; phase, which is the absolute value of difference between electrode spectral phases; length 2 path strength, which is the average strength of a connection between an electrode pair passing through another recording site; coherence with network, which is the average coherence between a given electrode pair and the rest of the network; coherence with stim sites, which is the average coherence between a given electrode pair and the stimulation sites; coherence difference, which is the average absolute difference in connection strength between each element of the electrode pair and the recorded network; electrode covariance, which is the average covariance of an electrode pair's coherence to the other electrodes in the network over time; and time covariance, which is the average covariance across time series between a given electrode pair's coherence and the others in the network (FIG. 5B) (see Methods for details of how these are calculated). These features are primarily derived from graph theoretic measures which have been used with success in past theoretical neuroscience analyses. Throughout this paper the inventors refer to this set of features as "network features."

Figure 6A:
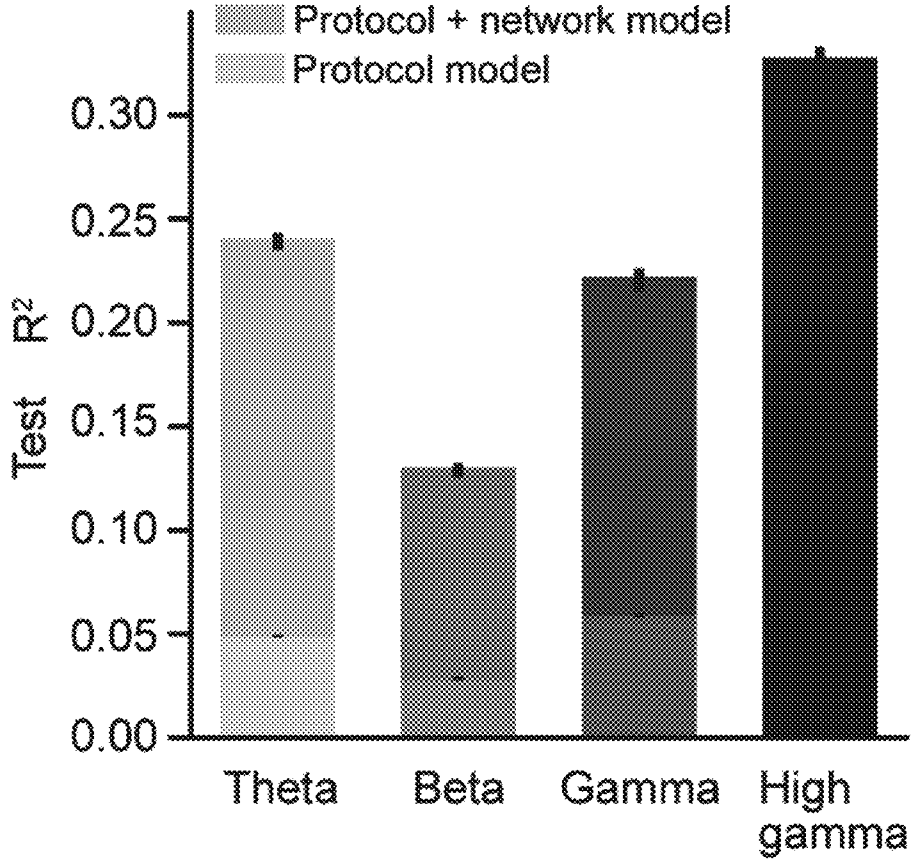
FIG. 6A is a bar graph indicating r-squared accuracy on held-out data in accordance with an embodiment of the present technology.

We observed that the model predictions on the test set was dramatically improved compared to the protocol-only model for each frequency band for both SS-FCC ($R^2$: Theta 0.240, Beta 0.130, Gamma 0.221, High-gamma 0.323) (FIGS. 6A-6F) and RS-FCC ($R^2$: Theta 0.218, Beta 0.087, Gamma 0.138, High-gamma 0.218) (FIG. 6*a*). This improvement in performance across all frequency bands and for both stimulated-state and resting-state contexts suggests that properties of the local network at baseline may be highly informative with respect to prediction of stimulation-induced changes.

FIG. 6A is a bar graph indicating r-squared accuracy on held-out data in accordance with an embodiment of the present technology. A model trained to predict stimulation-induced FCC over a cortical network based on protocol features alone is outperformed by one which incorporates information about existing network connectivity. Results in this figure correspond to prediction quality for SS-FCC; results are similar but slightly worse for RS-FCC. Bar graph indicates r-squared accuracy on held-out data. Grayscale bars (bottom) indicate accuracy of models trained on only protocol features and shaded bars (top) indicate accuracy of models trained on both protocol and network features. Error bars indicate standard deviation.

Figure 6B:
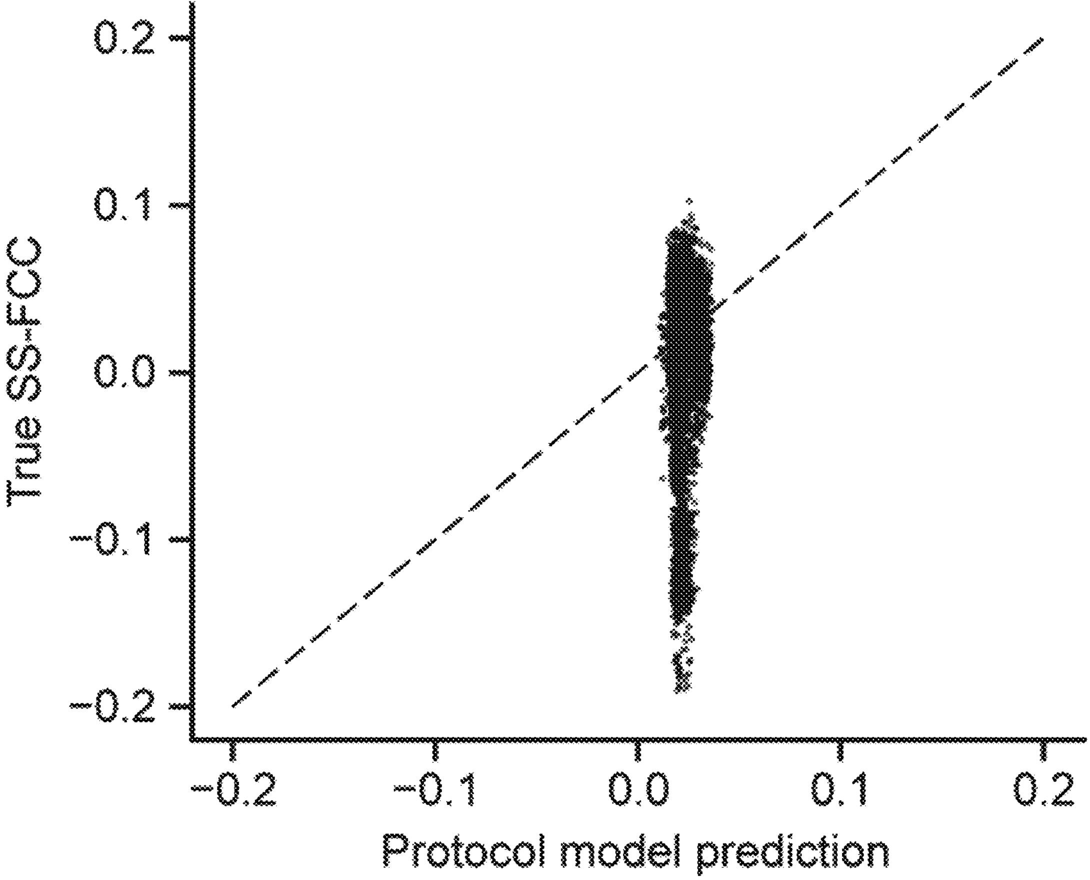
FIG. 6B is a scatter plot of the protocol model's predictions of network SS-FCC in accordance with an embodiment of the present technology.

FIG. 6B is a scatter plot of the protocol model's predictions of network SS-FCC in accordance with an embodiment of the present technology. In particular, the illustrated scatter plot corresponds to results of prediction of a representative experimental session from the protocol versus the protocol-and-network models. The scatter plot illustrates the protocol model's predictions of network SS-FCC versus the actual changes observed during that experimental session.

Figure 6C:
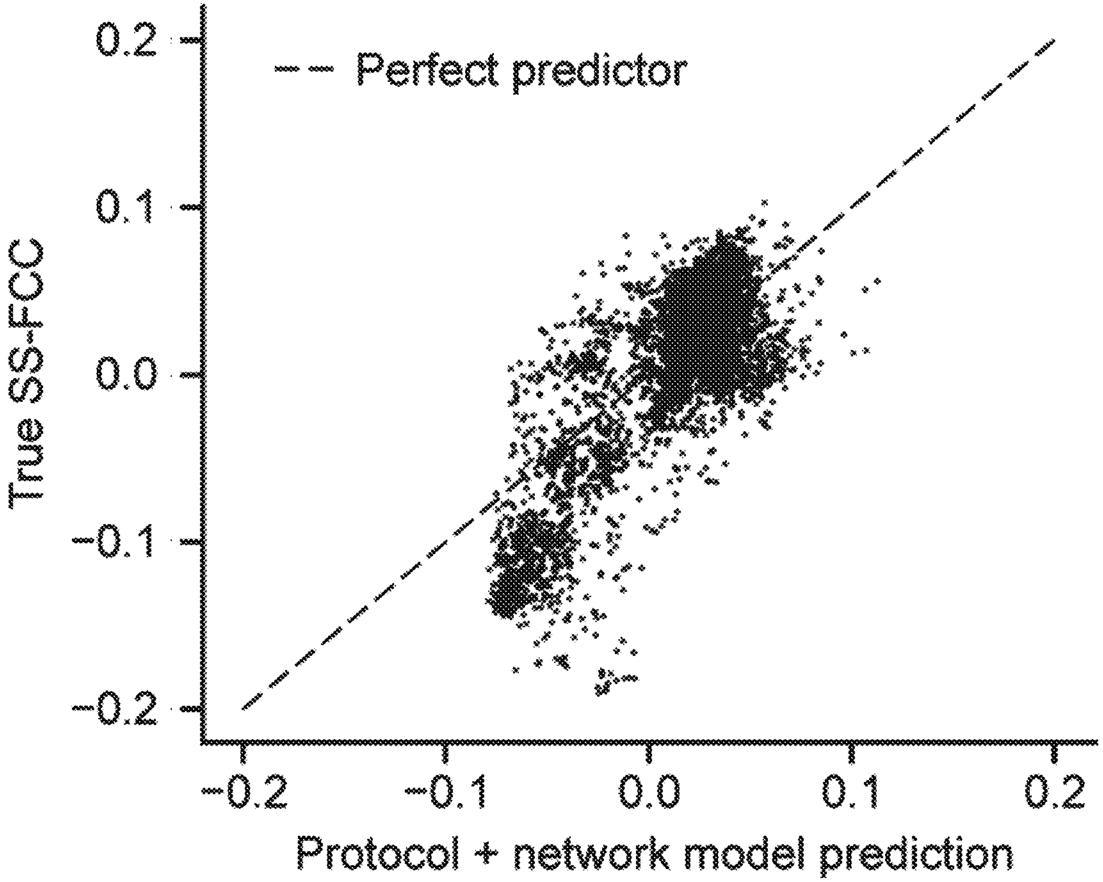
FIG. 6C is a scatter plot of the protocol-and-network model's predictions of SS-FCC in accordance with an embodiment of the present technology.

FIG. 6C is a scatter plot of the protocol-and-network model's predictions of SS-FCC in accordance with an embodiment of the present technology. In particular, the scatter plot corresponds to the protocol-and-network model's predictions of SS-FCC versus the actual changes observed during that experimental session.

Figure 6D:
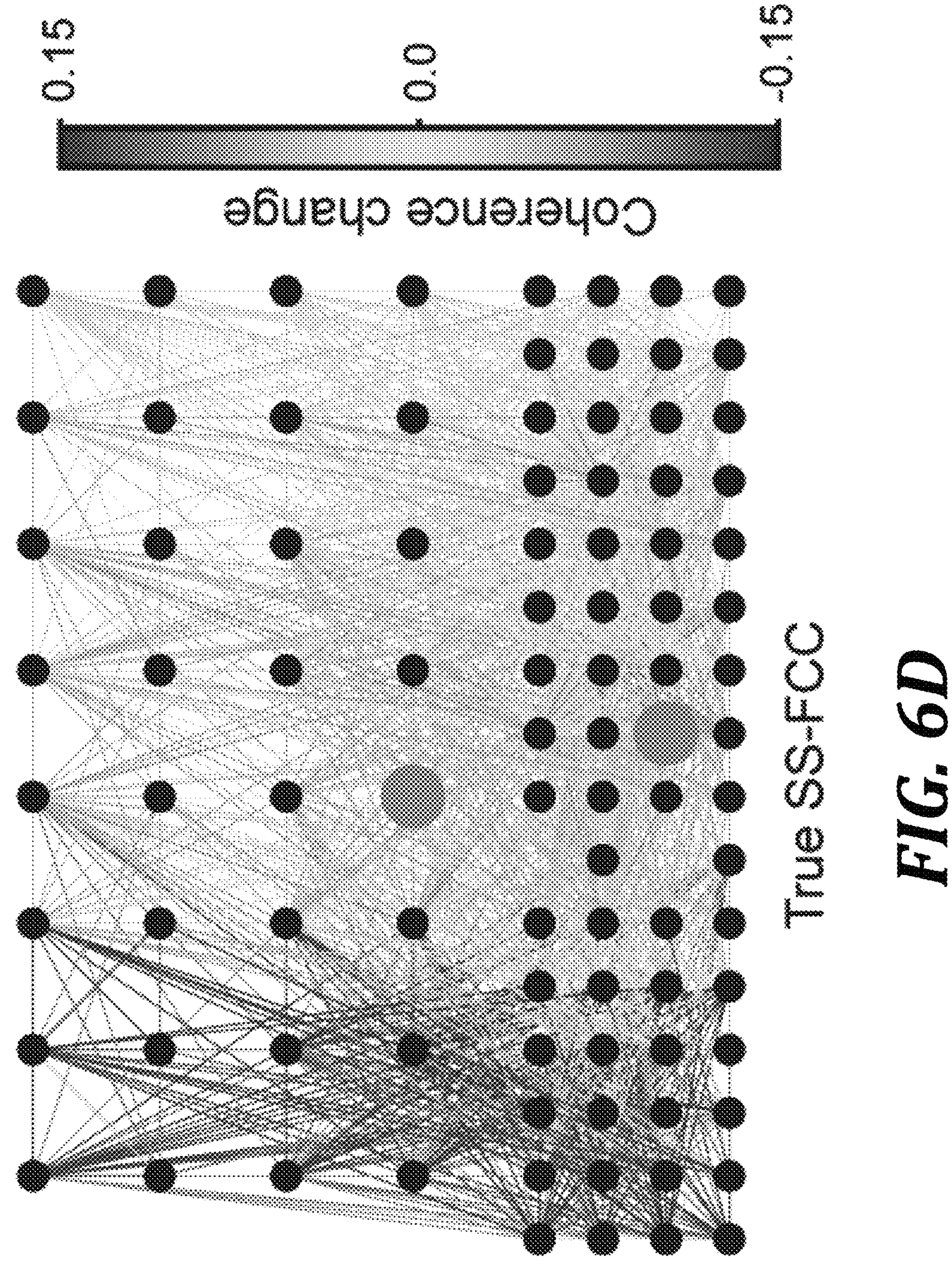
FIG. 6D is a graph of sample SS-FCC over a cortical network in accordance with an embodiment of the present technology.

FIG. 6D is a graph of sample SS-FCC over a cortical network in accordance with an embodiment of the present technology. In particular, the graph shows SS-FCC over a corticalnetwork, visualized over the μECoG array used for recording. Black circles indicate electrodes of the array, while lines indicate coherence change between electrode pairs. The observed coherence changes correspond to the y-axis of the graphs in FIGS. 6B and 6C.

Figure 6E:
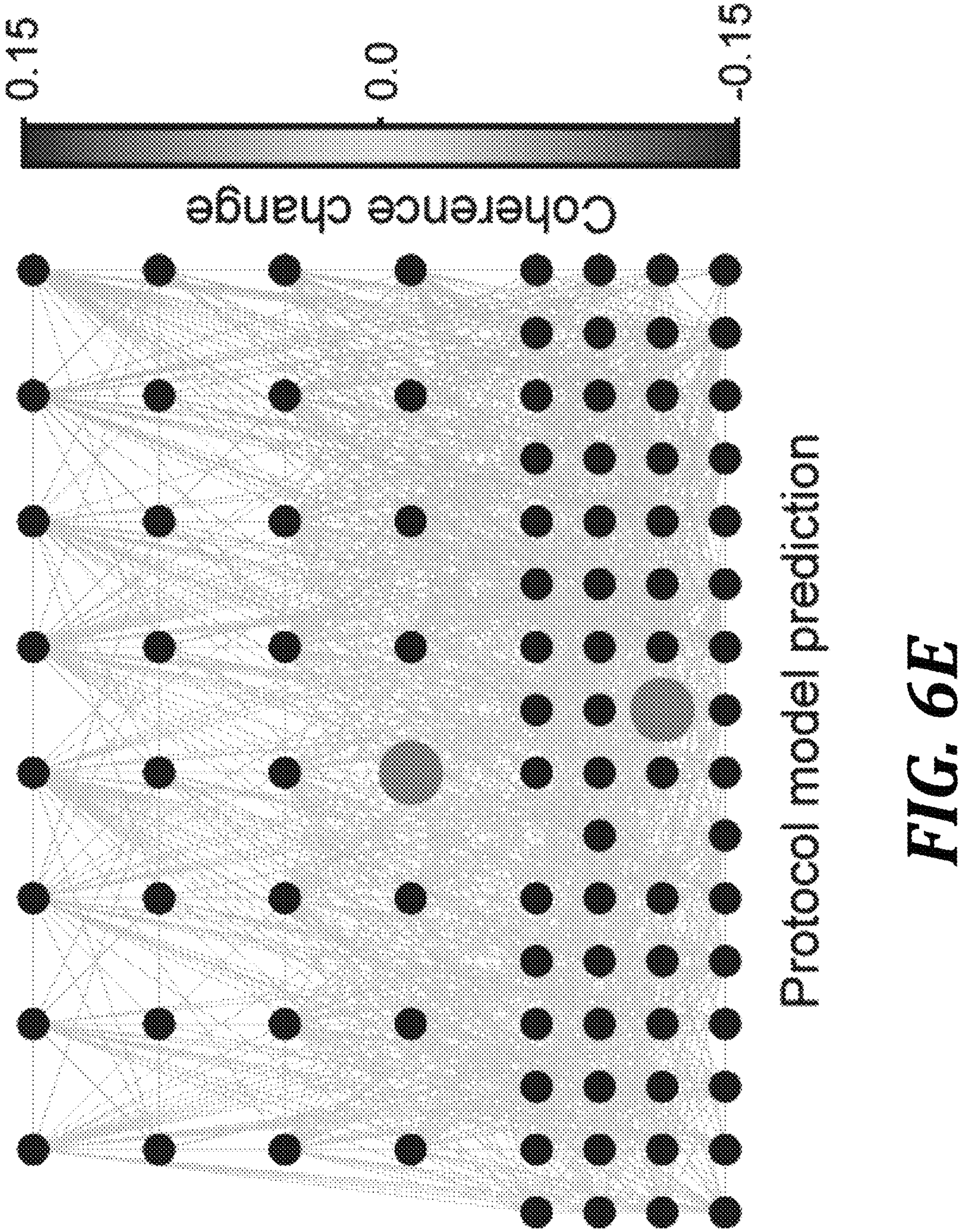
FIG. 6E is a protocol model's SS-FCC prediction in accordance with an embodiment of the present technology.

FIG. 6E is a protocol model's SS-FCC prediction in accordance with an embodiment of the present technology. In particular, the graph shows the protocol model's SS-FCC prediction, corresponding to the x-axis of FIG. 6B.

Figure 6F:
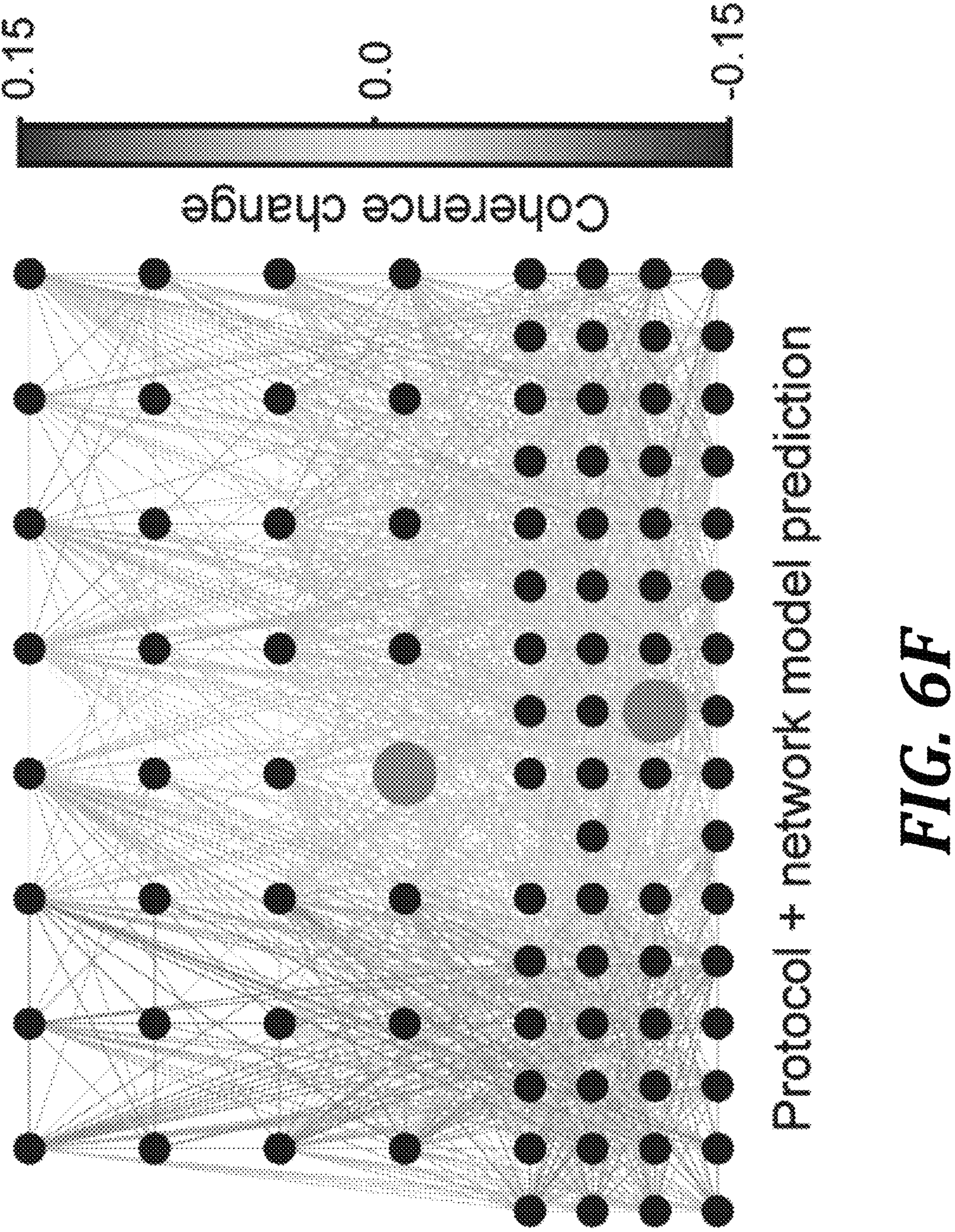
FIG. 6F is a protocol-and-network model's SS-FCC prediction in accordance with an embodiment of the present technology.

FIG. 6F is a protocol-and-network model's SS-FCC prediction in accordance with an embodiment of the present technology. In particular, the graph shows the protocol-and-network model's SS-FCC prediction, corresponding to the x-axis of FIG. 6C.

Individual Network Features Are More Important than Individual Stimulation Protocol Features for Predicting Functional Connectivity Changes We quantified the relative importance of each feature through the decrease in accuracy of prediction on the test set when that feature was excluded from the data. The statistical uncertainty associated with the importance was quantified through a resampling procedure.

Using this procedure, the importances is demonstrated of each feature per frequency band in for SS-FCC and in for RS-FCC. Four of the five most important features for SS-FCC prediction and each of the five most important features for RS-FCC prediction were network features. Features appearing in the top five of both contexts were time covariance, coherence difference, and initial coherence, which were all network features. Delay and time-ordered block number were the two most important of the protocol features for both SS-FCC and RS-FCC prediction.

Feature Mappings Display Diverging Trends Across Frequency Bands

We decomposed the nonlinear model into feature mappings representing the estimated mapping between each individual feature and the change in coherence. The statistical uncertainty associated with the estimated nonlinear mapping from the feature to the response was quantified through a resampling procedure and representative feature mappings were obtained through point-wise interpolation of the resampled feature mappings (see Methods for details).

Figure 7A:
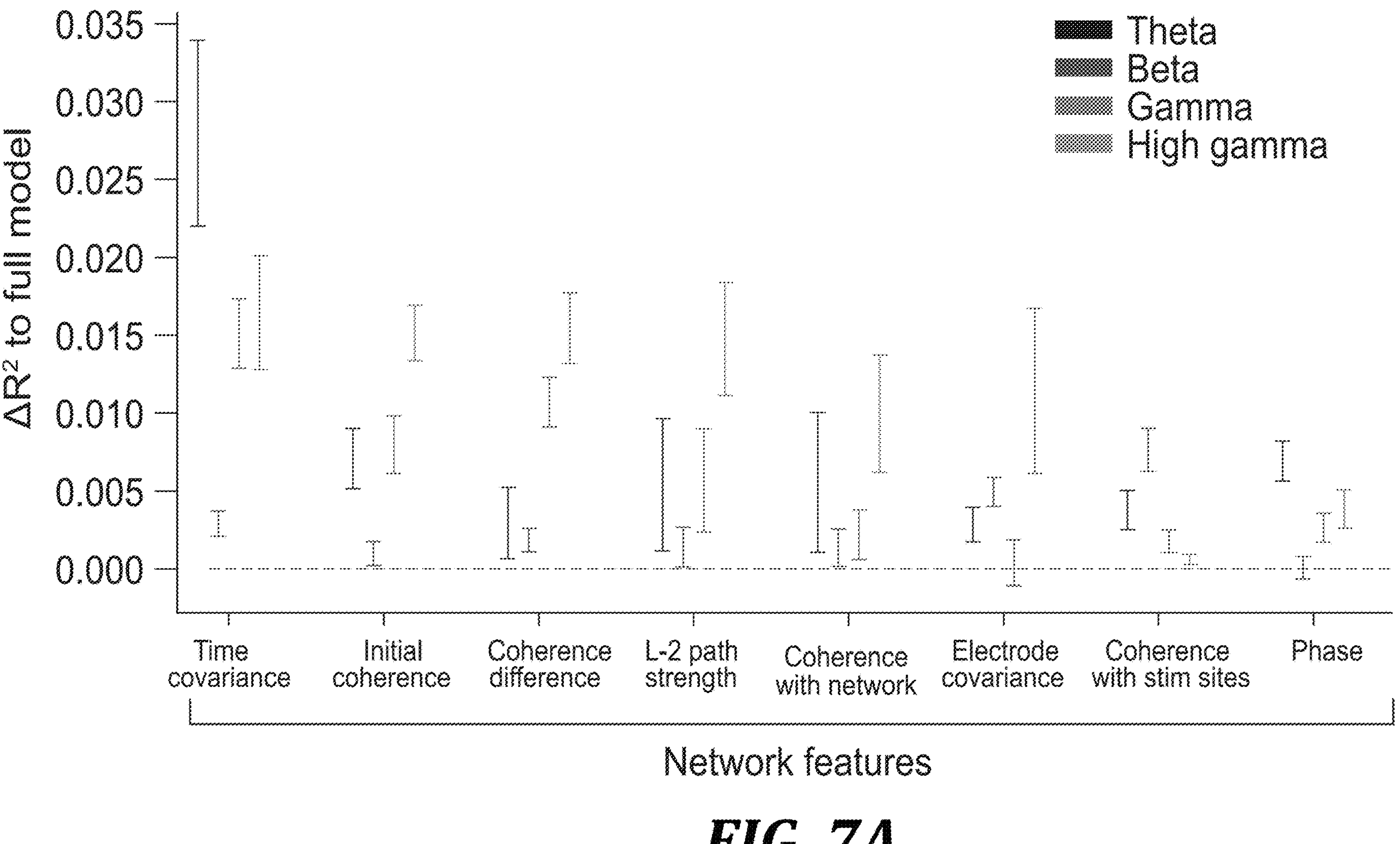
FIG. 7A is a graph of feature importances as measured by decrease in model accuracy when the feature was omitted in accordance with an embodiment of the present technology.
Figure 7A:
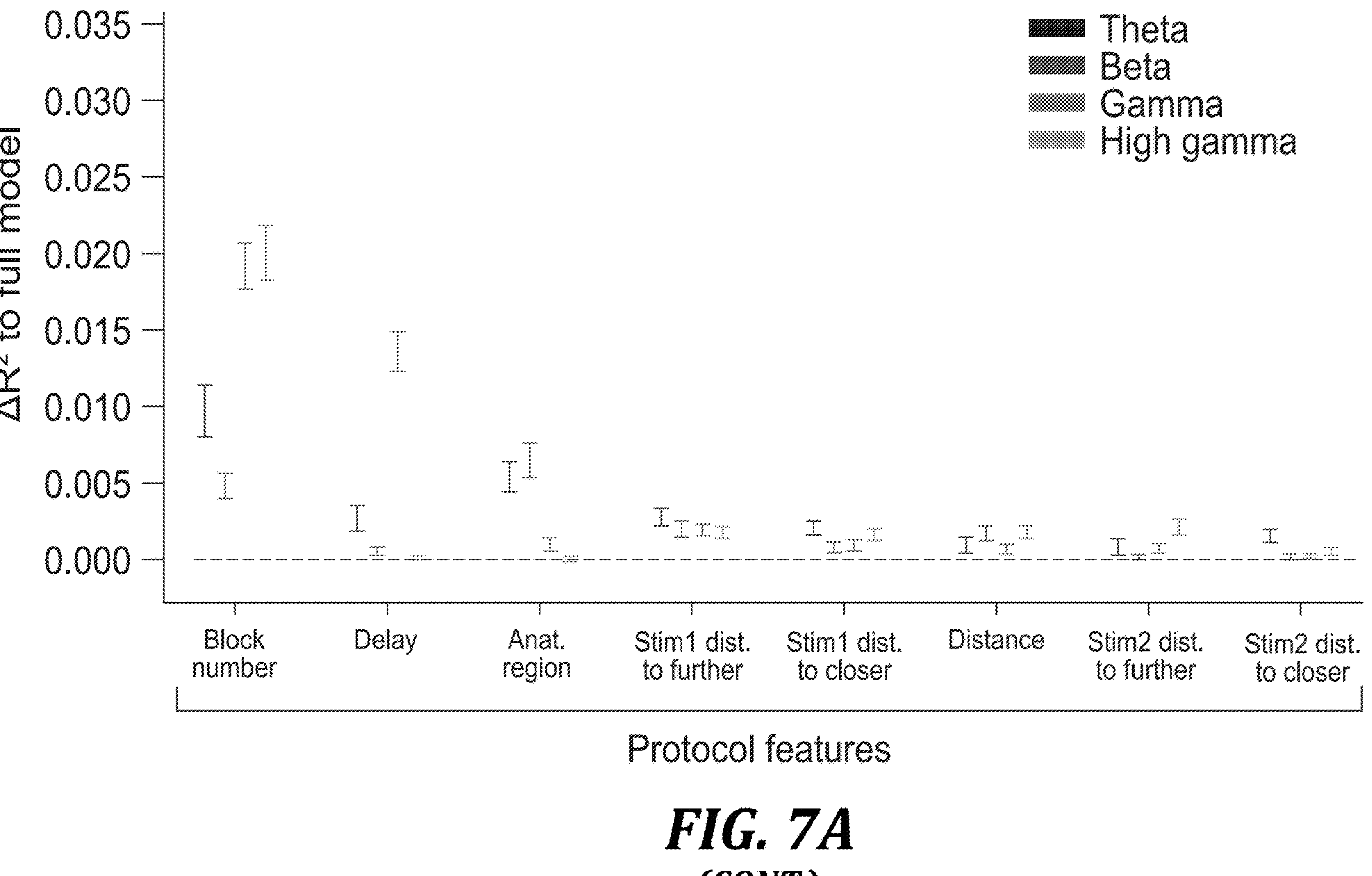

FIG. 7A is a graph of feature importances as measured by decrease in model accuracy when the feature was omitted in accordance with an embodiment of the present technology. Results in this figure correspond to the SS-FCC model; results were similar for the RS-FCC model. Feature importances as measured by the decrease in model accuracy when the feature was omitted. Features were partitioned into the protocol and network categories, then sorted by average importance over all frequency bands. Line ranges indicate 95% confidence intervals.

Figures 7B, 7C, 7D:
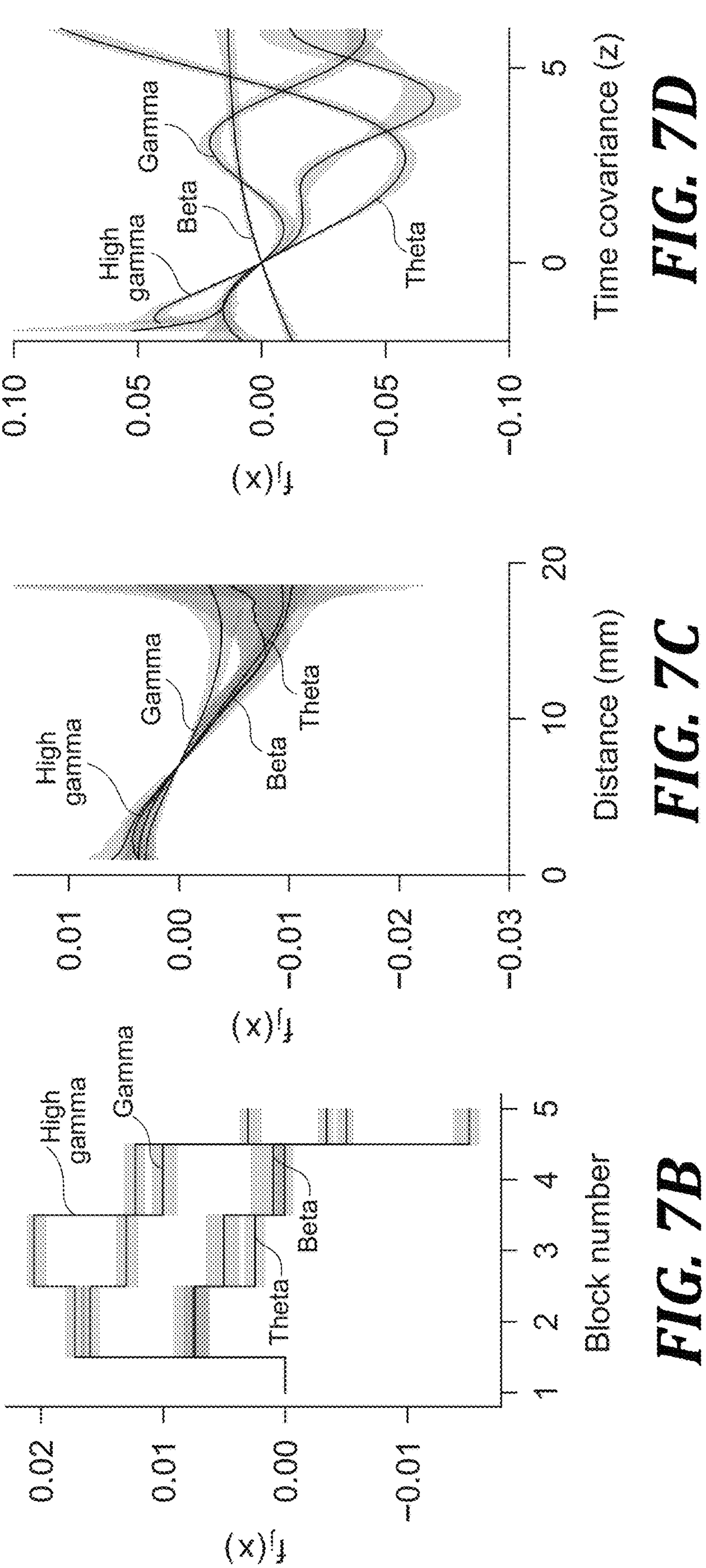
FIG. 7B is a graph of feature mapping for time-ordered block number in accordance with an embodiment of the present technology.
FIG. 7C is a graph of feature mapping for electrode pair distance in accordance with an embodiment of the present technology.
FIG. 7D is a graph of feature mapping of time covariance in accordance with an embodiment of the present technology.

FIG. 7B is a graph of feature mapping for time-ordered block number in accordance with an embodiment of the present technology. For FIGS. 7B-7F fj (x) indicates the contribution of a feature to the predicted FCC. Shading indicates 95% confidence intervals.

FIG. 7C is a graph of feature mapping for electrode pair distance in accordance with an embodiment of the present technology.

FIG. 7D is a graph of feature mapping of time covariance in accordance with an embodiment of the present technology.

Figure 7F:
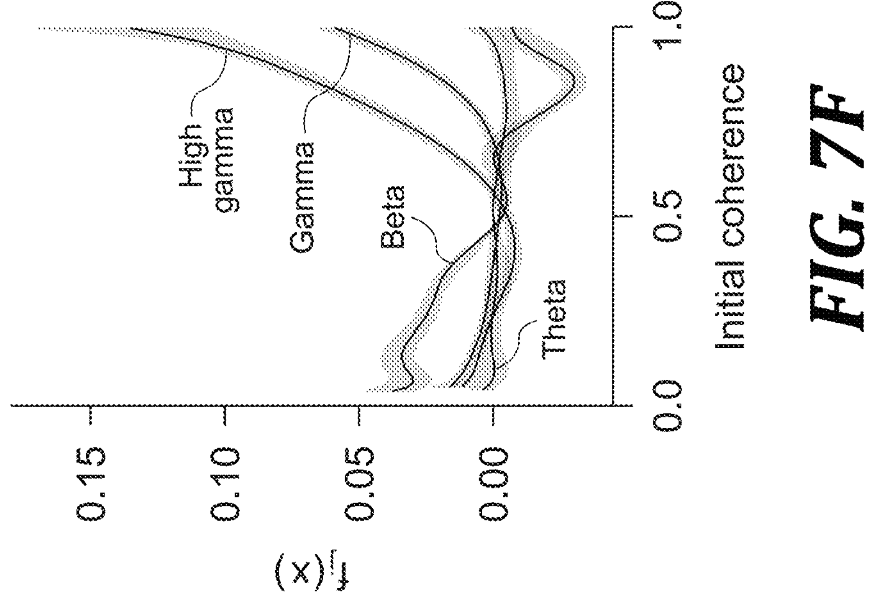
FIG. 7F is a graph of feature mapping of initial coherence features in accordance with an embodiment of the present technology.
Figure 7E:
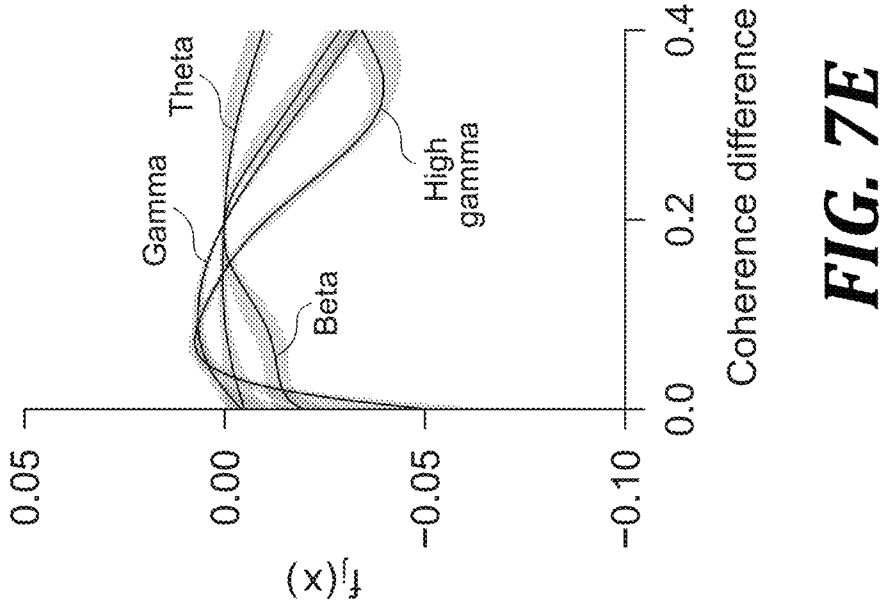
FIG. 7E is a graph of feature mapping of coherence difference in accordance with an embodiment of the present technology.

FIG. 7E is a graph of feature mapping of coherence difference in accordance with an embodiment of the present technology.

FIG. 7F is a graph of feature mapping of initial coherence features in accordance with an embodiment of the present technology.

Figure 7G:
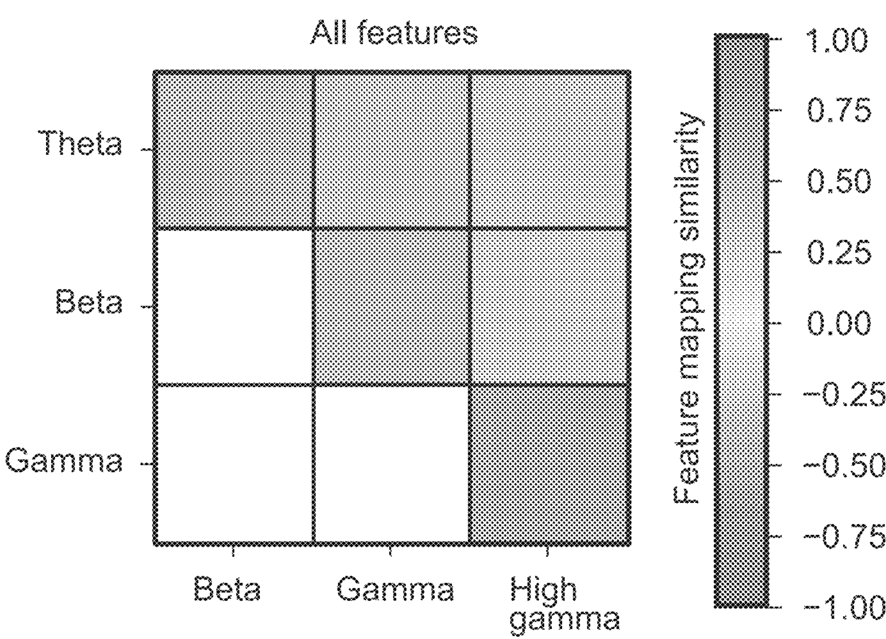
FIG. 7G is a graph of average cosine similarity of the component functions for all features in accordance with an embodiment of the present technology.

FIG. 7G is a graph of average cosine similarity of the component functions for all features in accordance with an embodiment of the present technology.

Figure 7H:
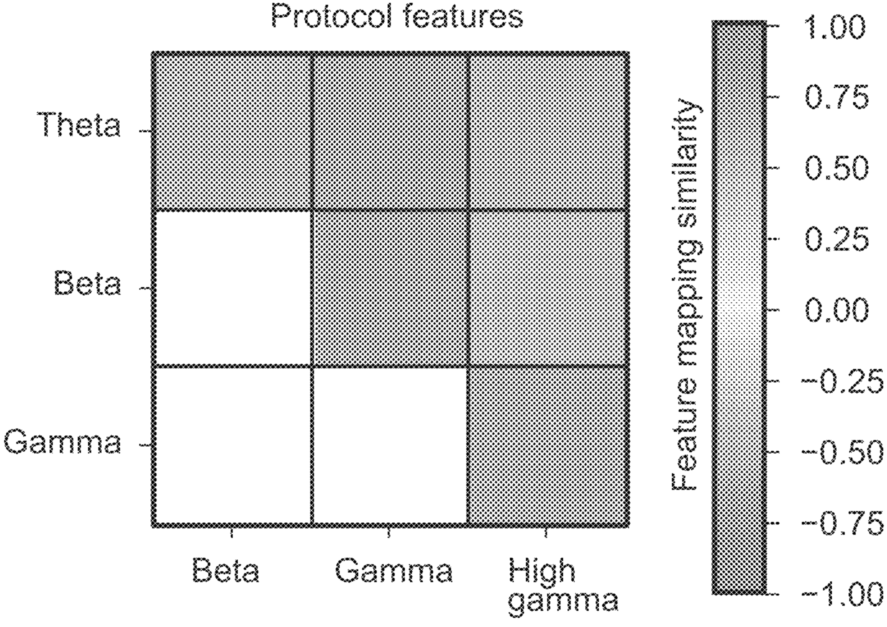
FIG. 7H is a graph of average cosine similarity of the component functions for protocol features in accordance with an embodiment of the present technology.

FIG. 7H is a graph of average cosine similarity of the component functions for protocol features in accordance with an embodiment of the present technology.

Figure 7I:
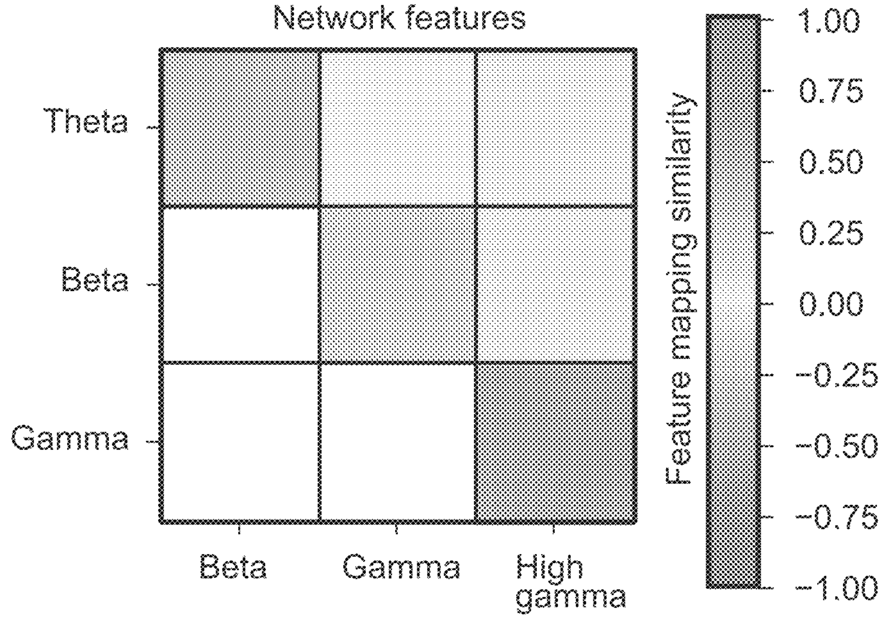
FIG. 7I is a graph of average cosine similarity of the component functions for graph features in accordance with an embodiment of the present technology.

FIG. 7I is a graph of average cosine similarity of the component functions for graph features in accordance with an embodiment of the present technology. Average cosine similarity of the component functions between each pair of frequency bands is shown over all features in FIG. 7G, over protocol features in FIG. 7H, and over graph features in FIG. 7I.

We plot the SS-FCC feature mappings of some features as well as others of interest in FIGS. 7B-7F. We observed that feature mappings were generally more complicated for network features than for protocol features. For example, the time covariance feature varies from a near-linear increase in the Beta band to a high-order polynomial in the High gamma band, while the distance feature mapping exhibits a nearly linear decrease in the high-confidence regions of all frequency band models (FIG. 7C). We also observed that in the higher frequency bands, electrodes which had a higher initial coherence tended to strongly increase their coherence when stimulated (FIG. 7F). Additionally, the inventors found a small effect of increasing SS-FCC for the first two or three temporal blocks depending on frequency band, followed by decreasing SS-FCC in later blocks (FIG. 7B). We evaluate the temporal characteristics of the FCC in more detail in a later section.

We summarized the similarity of all features, protocol features, and network features by calculating the cosine similarity of the feature mappings (FIG. 7G-7I). Generally, the inventors found that the mappings from protocol features to SS-FCC were fairly consistent across frequency bands, while the mappings from network features to SS-FCC varied sharply between frequency bands. Only the network feature mappings of Gamma and High-gamma were similar.

Feature Mappings Are Similar for Stimulated-State and Resting-State Functional Connectivity Changes We calculated the similarity of feature mappings between SS-FCC and RS-FCC.

Figure 8A:
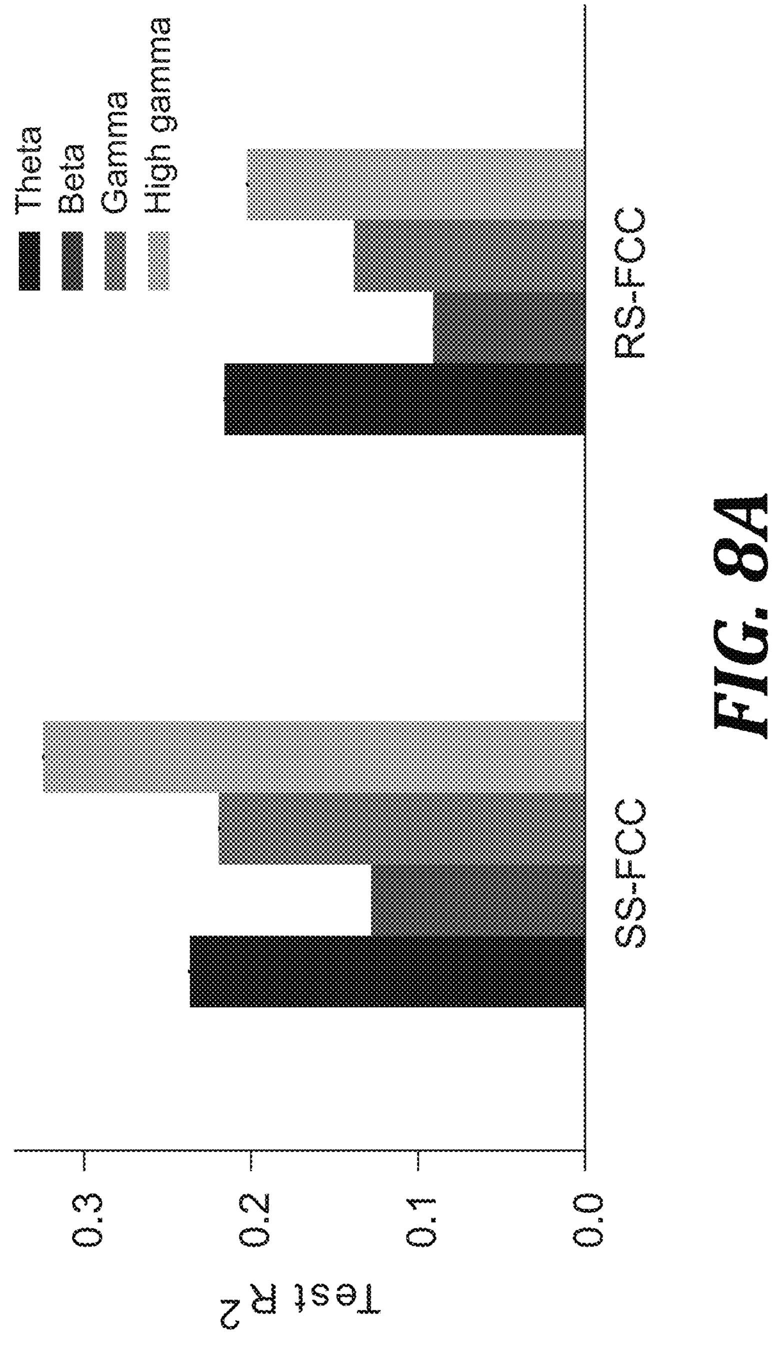
FIG. 8A is a comparison graph of the predictive accuracy for nonlinear additive models of SS-FCC prediction versus RSFCC prediction in accordance with an embodiment of the present technology.

FIG. 8A is a comparison graph of the predictive accuracy for nonlinear additive models of SS-FCC prediction versus RSFCC prediction in accordance with an embodiment of the present technology.

Figure 8B:
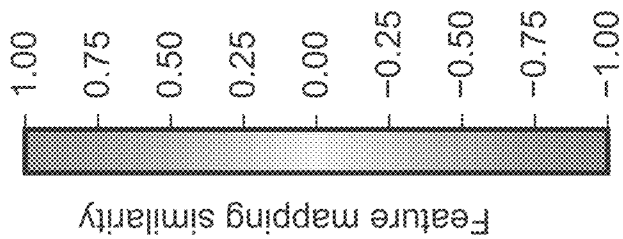
FIG. 8B is a graph of Heatmap of average cosine similarity between feature mappings of SS-FCC and RS-FCC over frequencies in accordance with an embodiment of the present technology.
Figure 8B:
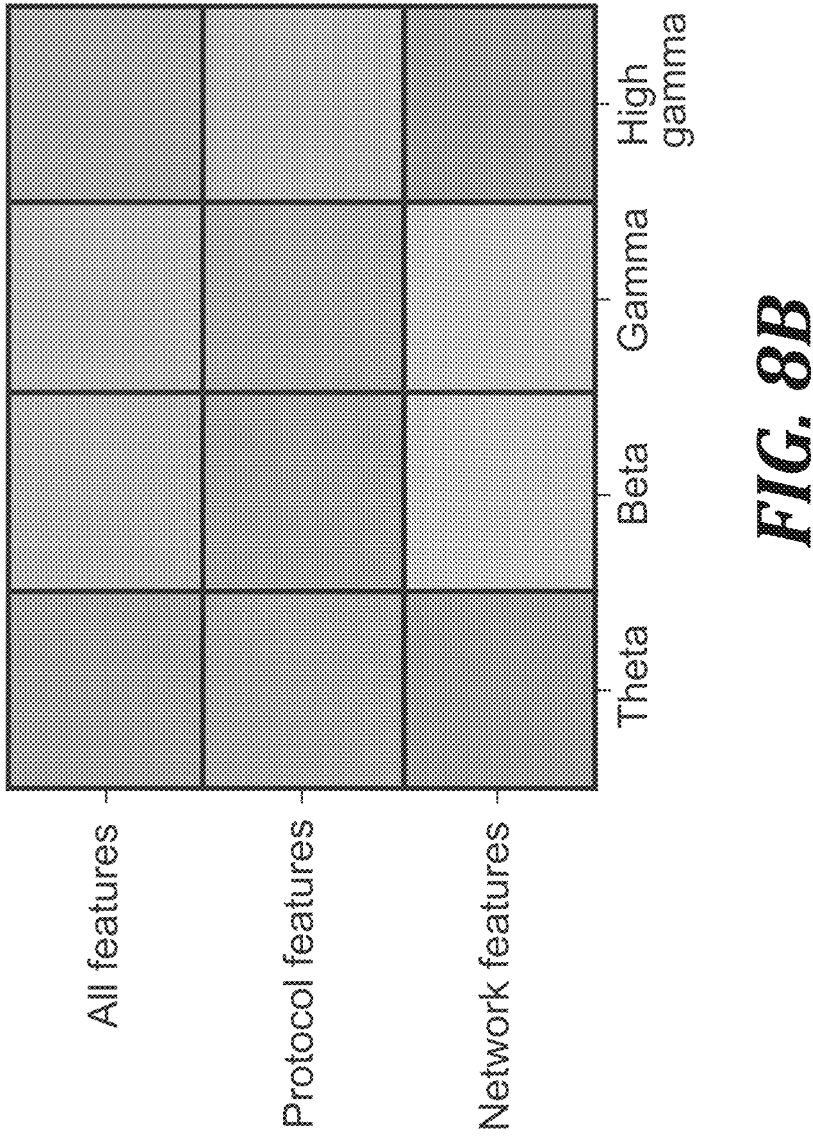
Figure 8E:
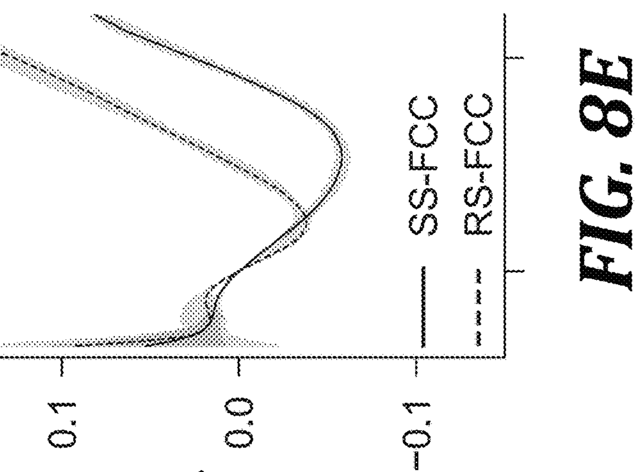
FIGS. 8C-8G are graphs of comparison of feature mappings for SS-FCC and RS-FCC models for theta band where features are respectively anatomical region of electrodes, electrode pair distance, time covariance (z-scored), initial coherence, and coherence difference.
Figure 8D:
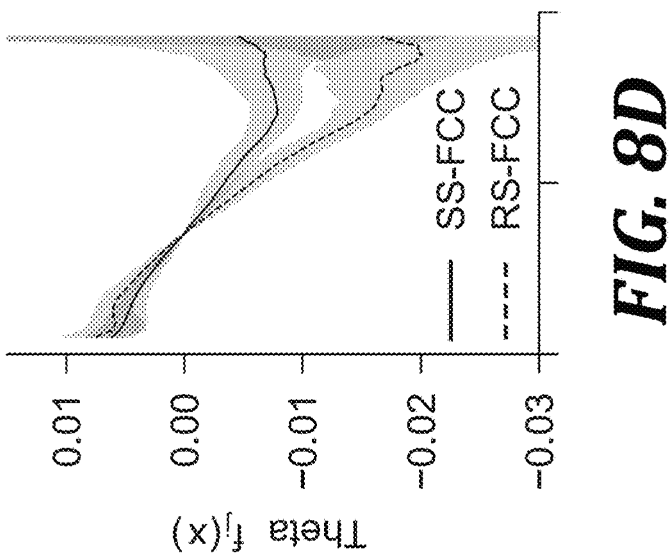
Figure 8C:
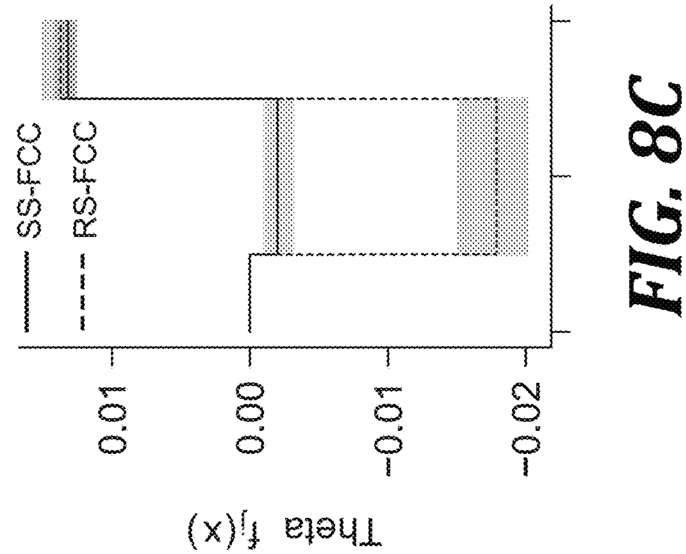
Figures 8F, 8G:
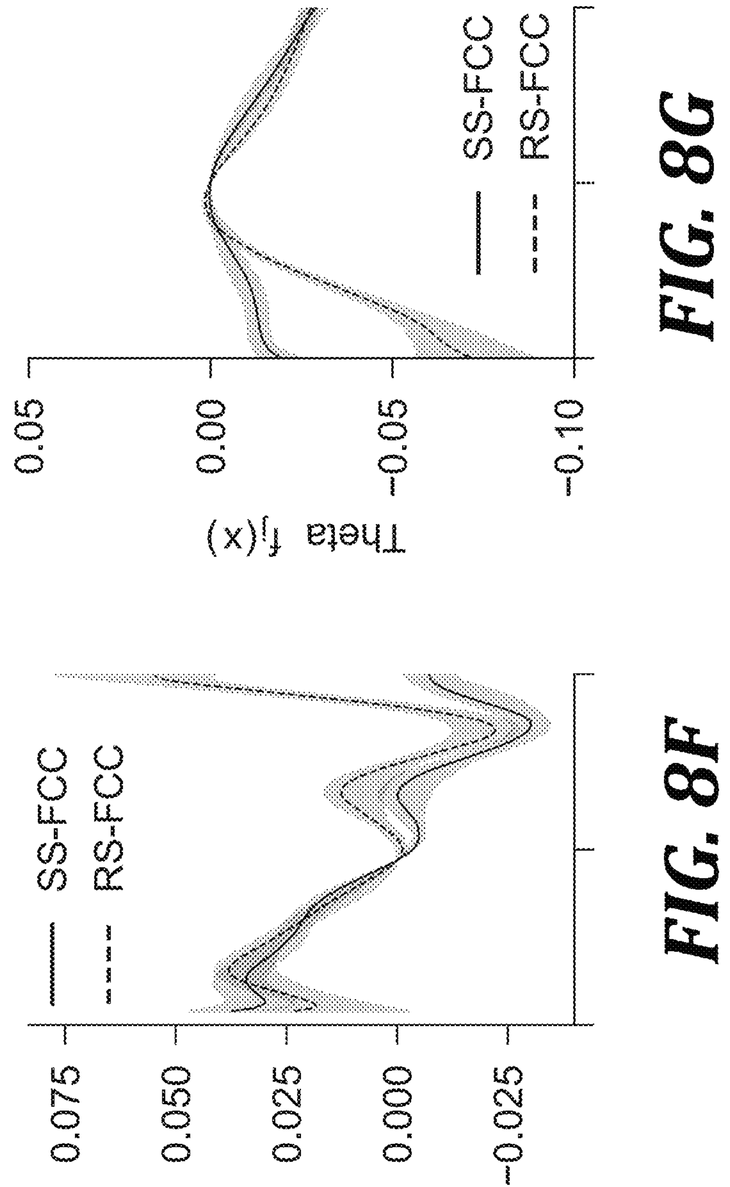
Figure 8J:
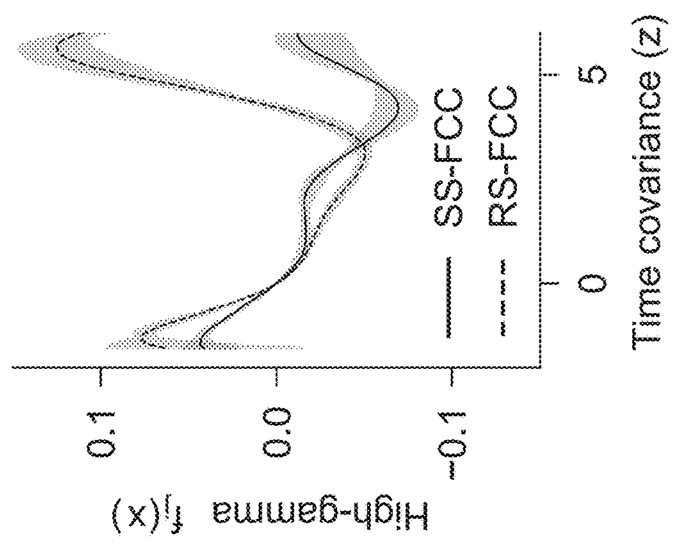
FIGS. 8H-8L are graphs of comparison of feature mappings for SS-FCC and RS-FCC models for high-gamma band where features are respectively anatomical region of electrodes, electrode pair distance, time covariance (z-scored), initial coherence, and coherence difference.
Figure 8I:
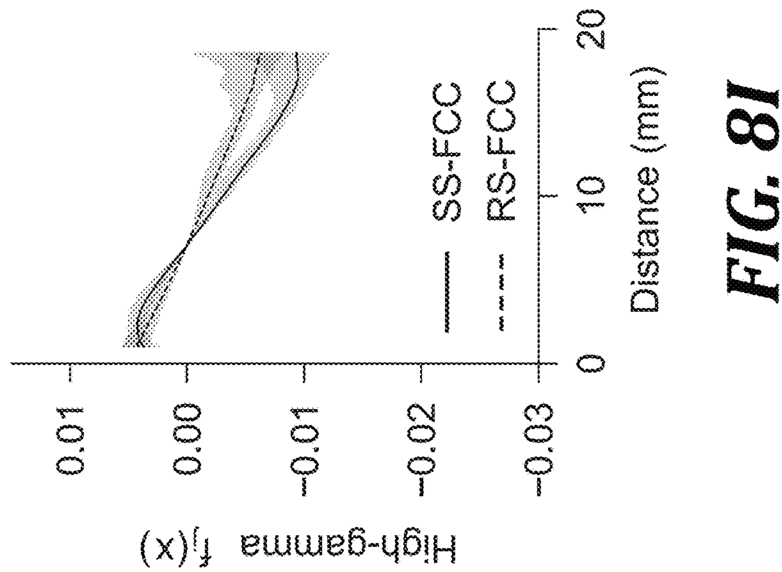
Figure 8H:
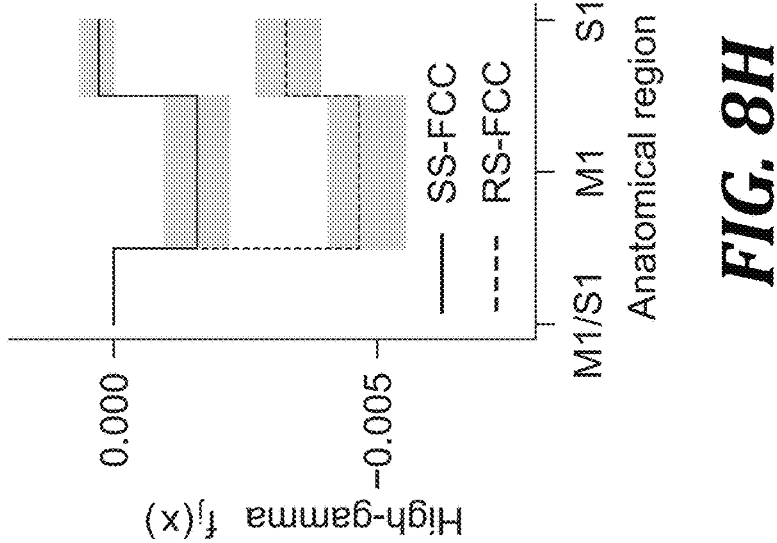
Figure 8L:
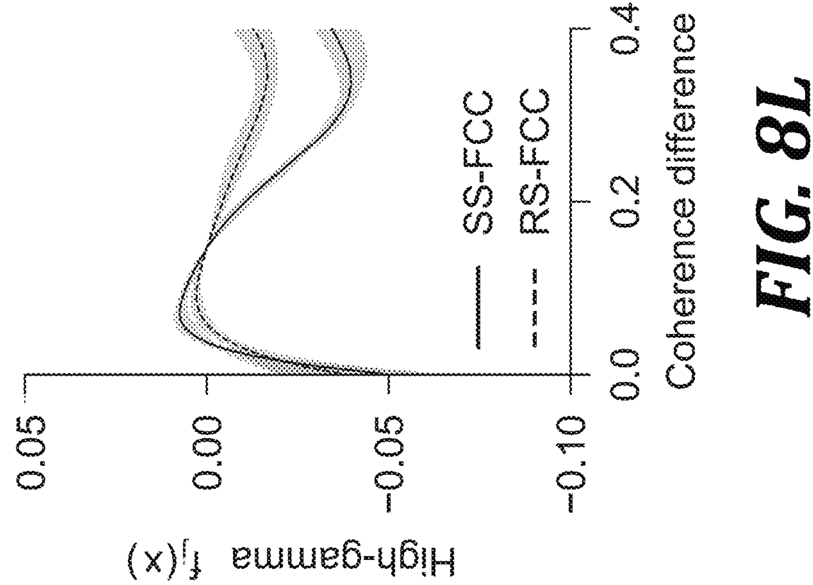
Figure 8K:
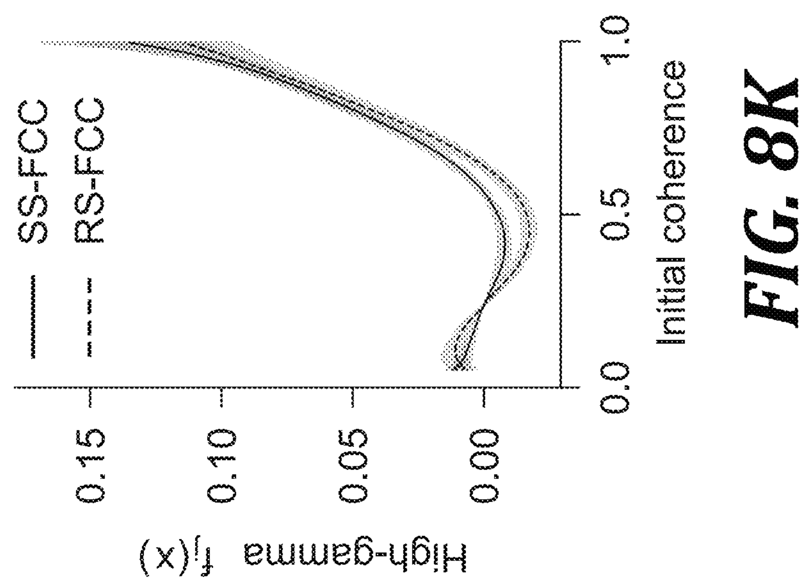
Figure 9A:
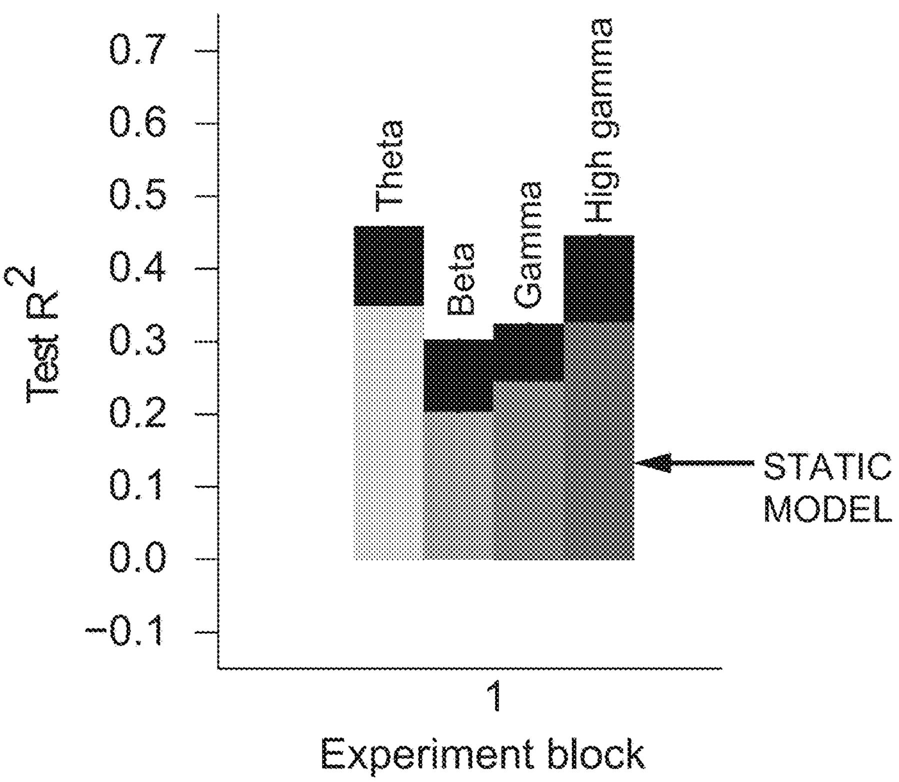
FIGS. 9A-9E are bar graphs indicating r-squared accuracy on held-out data of the time-varying and static model predictions for different experiment blocks in accordance with embodiments of the present technology.
Figure 9B:
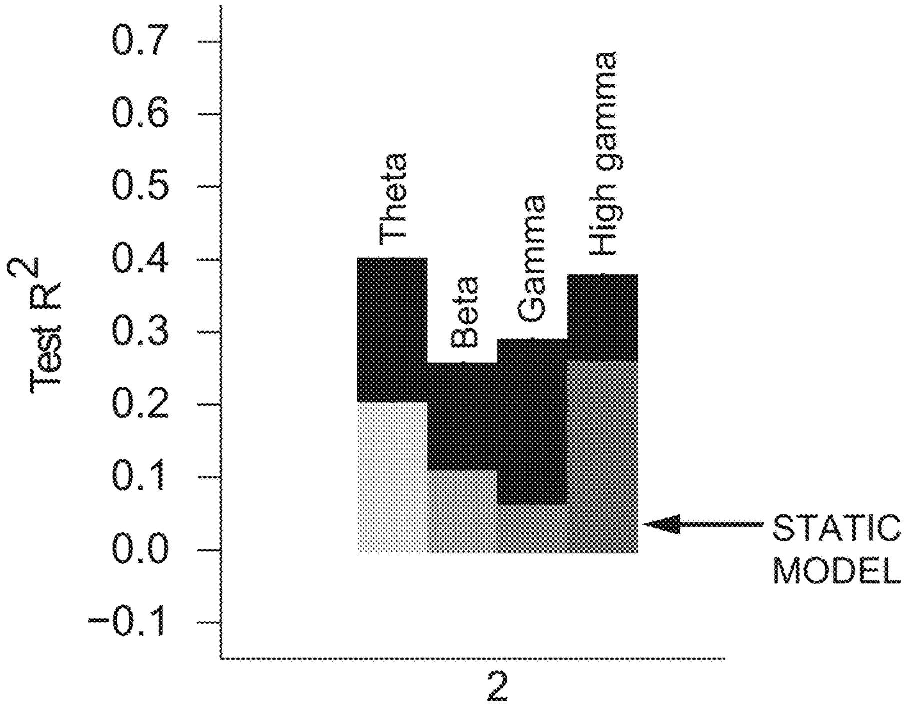
Figure 9C:
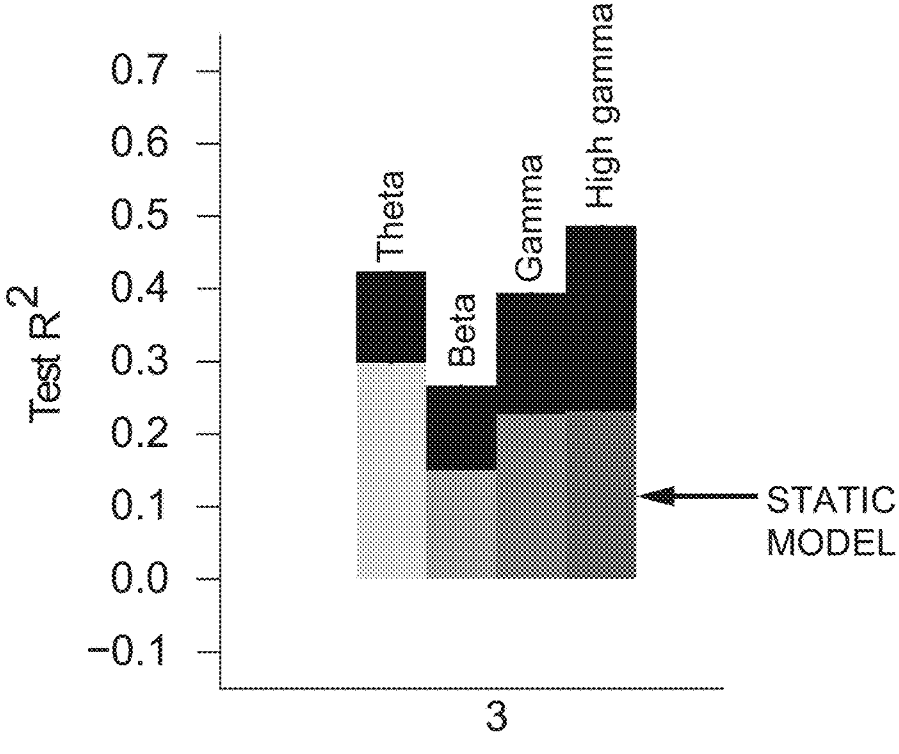
Figure 9D:
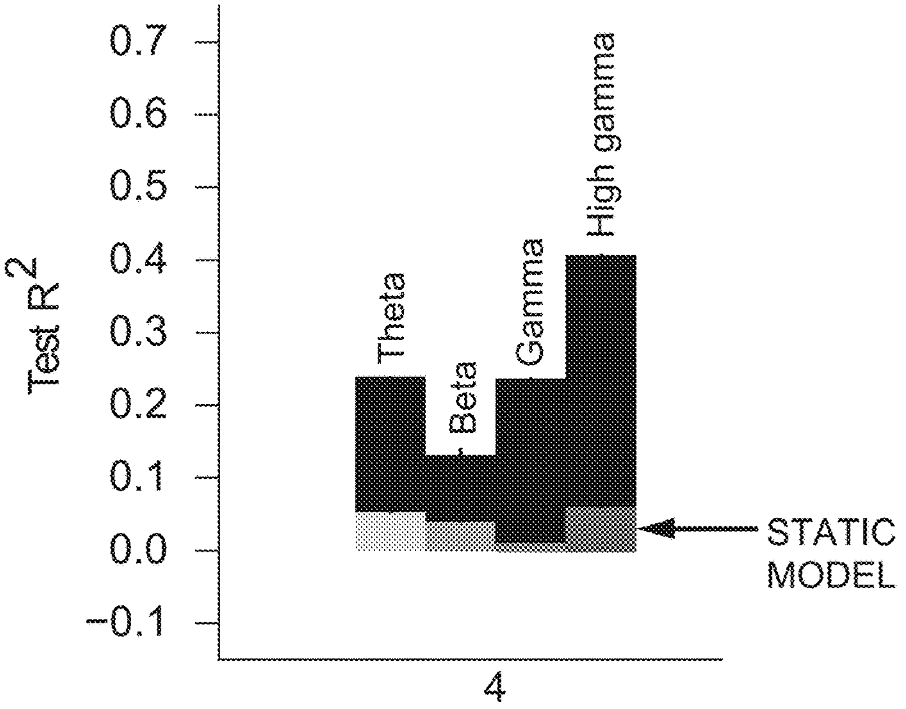
Figure 9E:
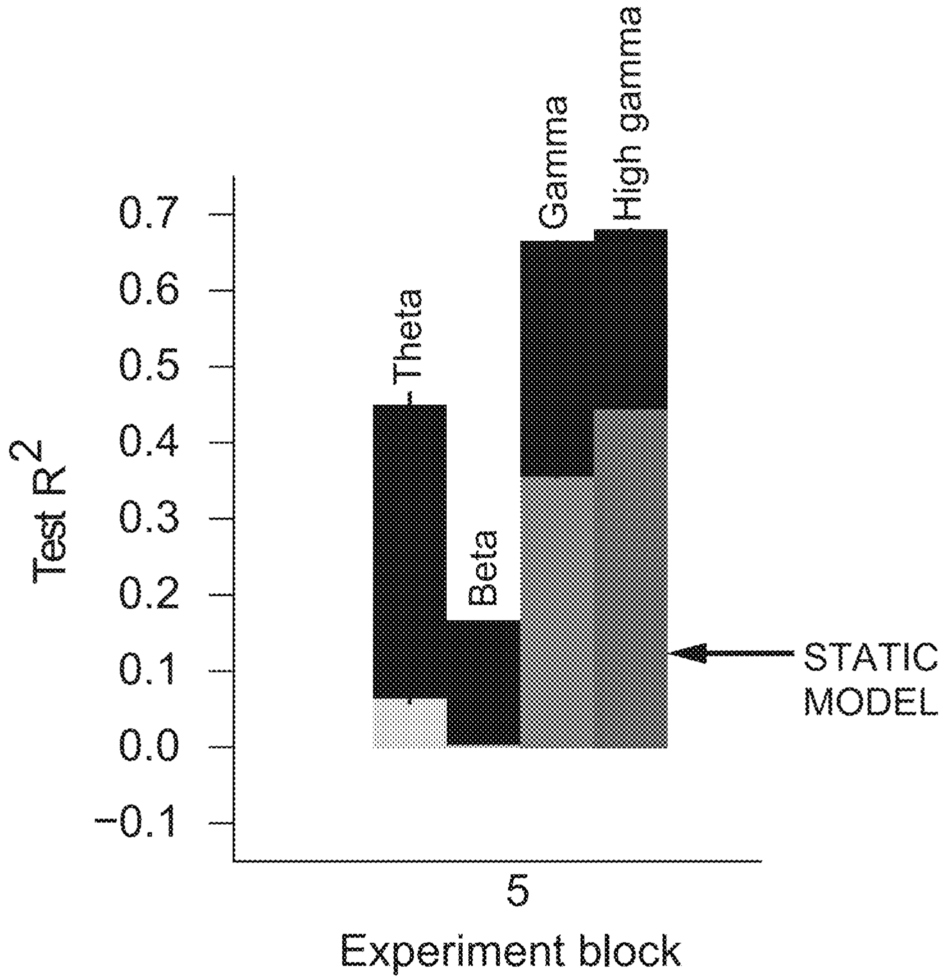
Figure 10A:
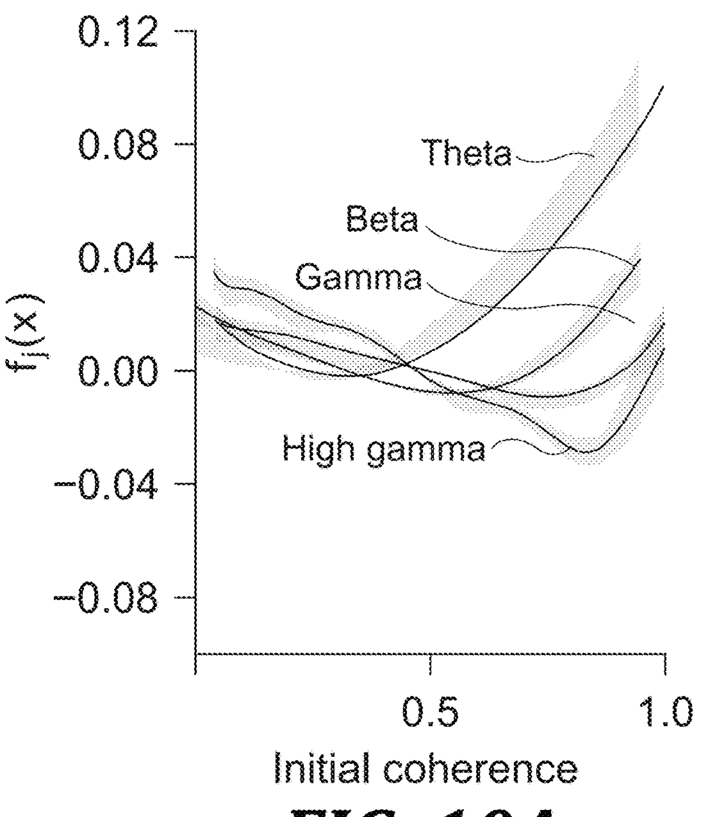
FIGS. 10A-10E are graphs indicating feature mappings of initial coherences for different experiment blocks in accordance with embodiments of the present technology.
Figure 10B:
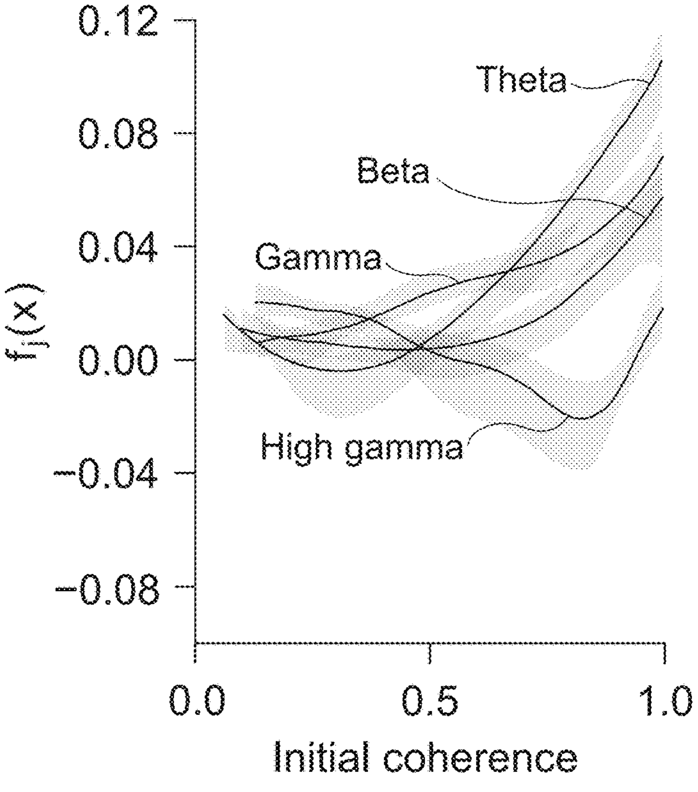
Figure 10C:
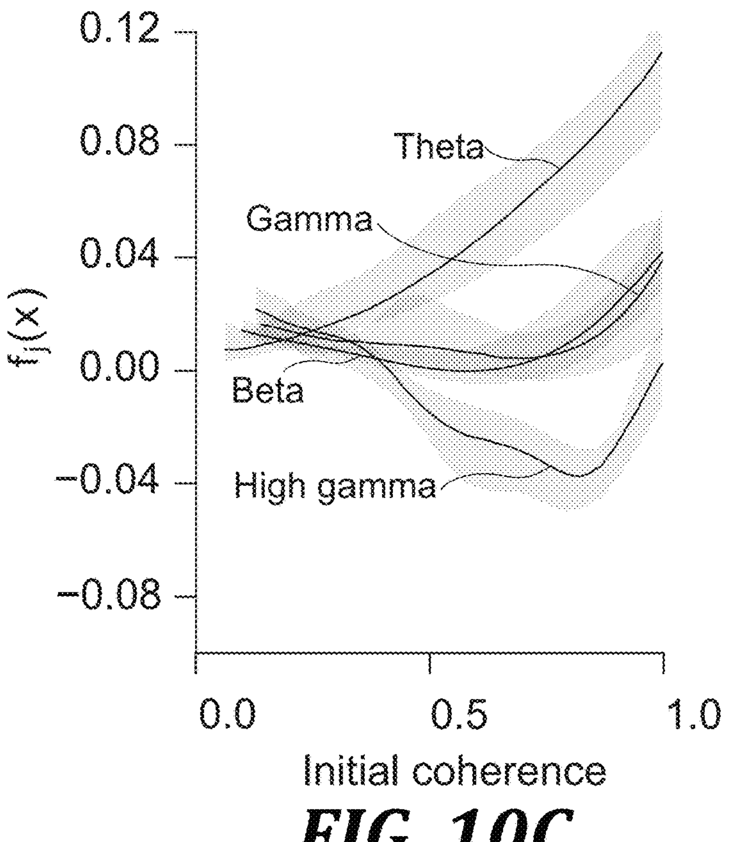
Figure 10D:
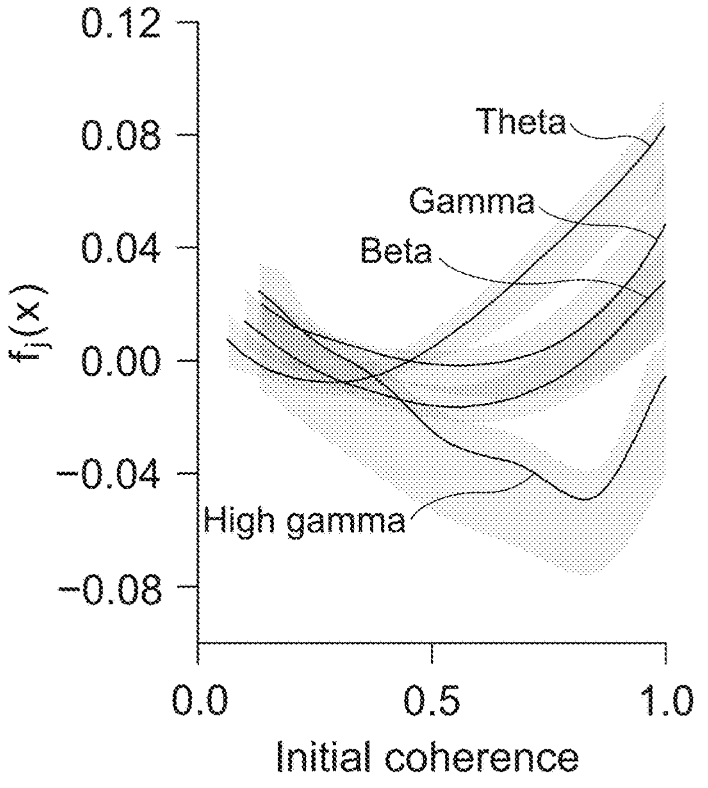
Figure 10E:
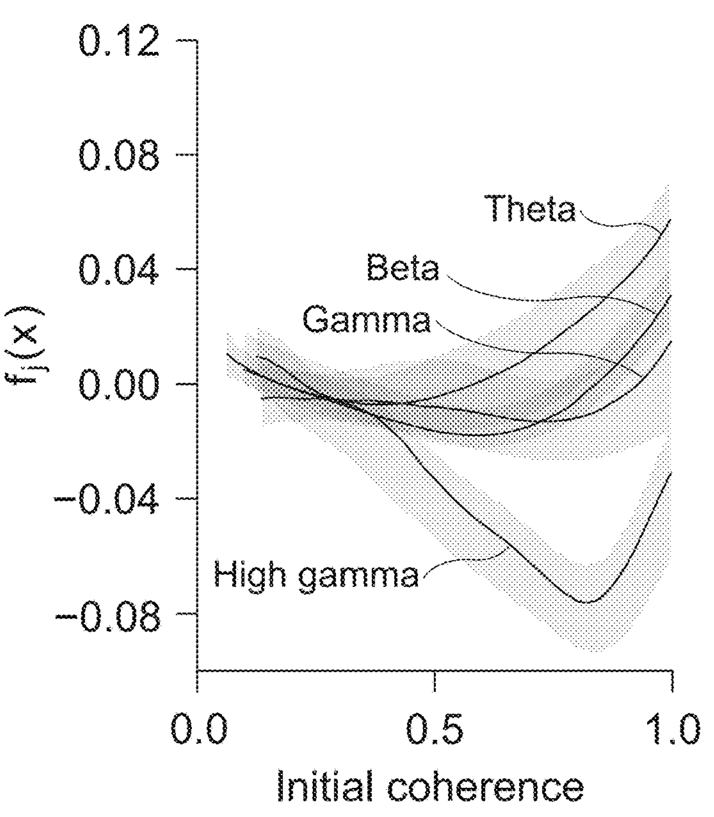
Figure 11A:
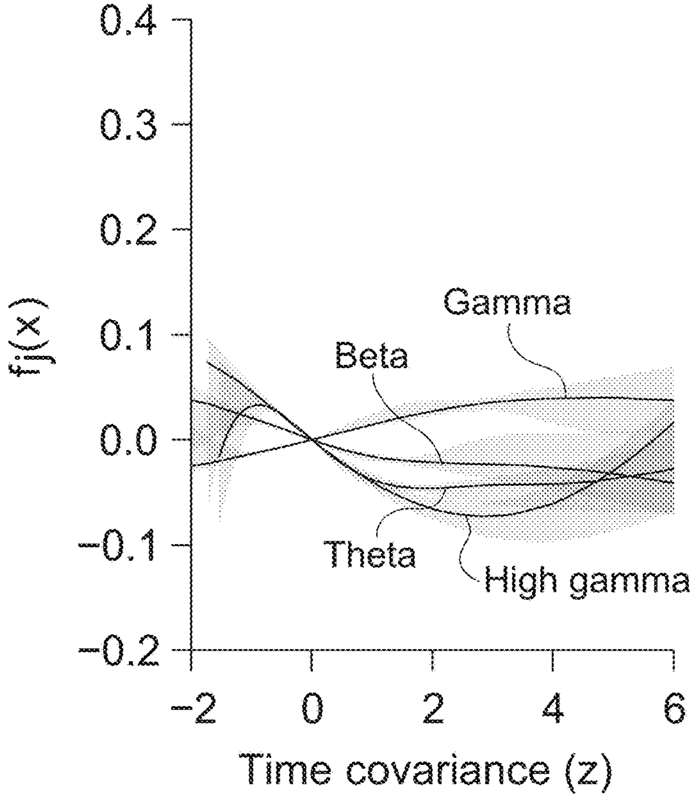
FIGS. 11A-11E are graphs indicating feature mappings of time covariance for different experiment blocks in accordance with embodiments of the present technology.
Figure 11B:
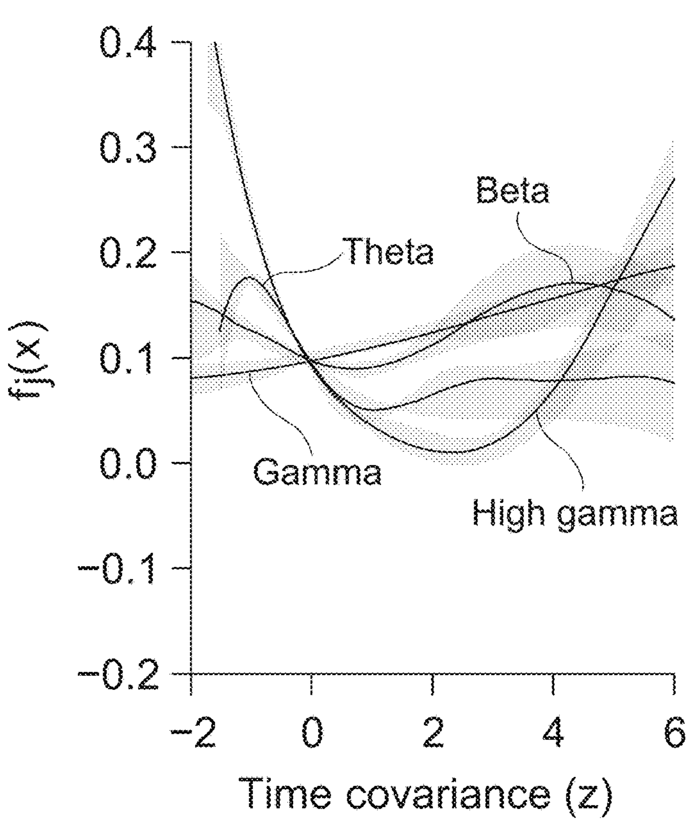
Figure 11C:
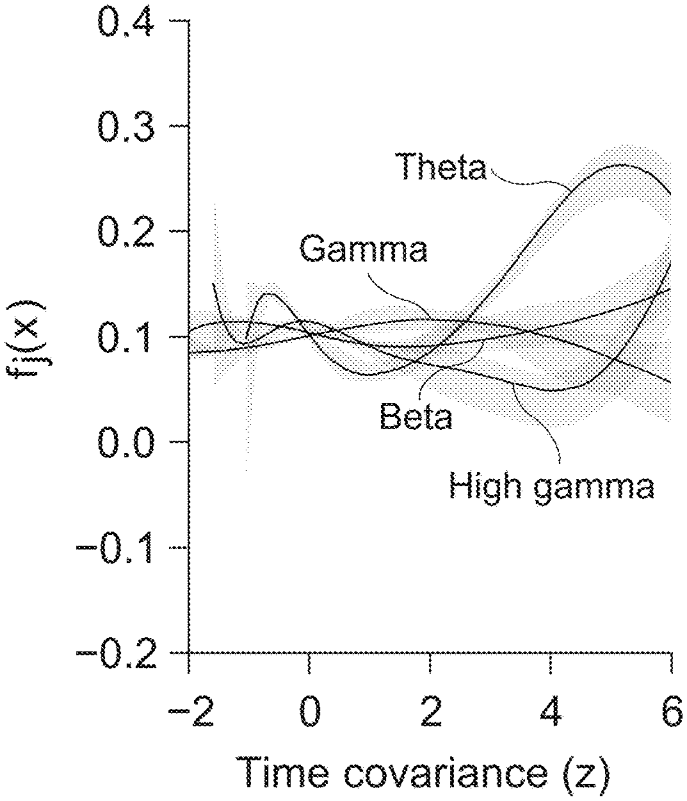
Figure 11D:
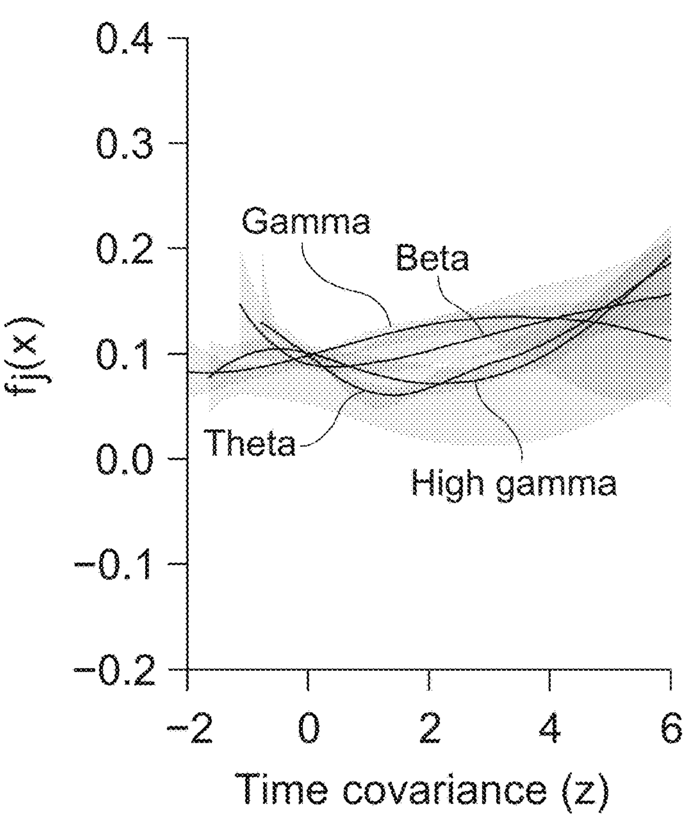
Figure 11E:
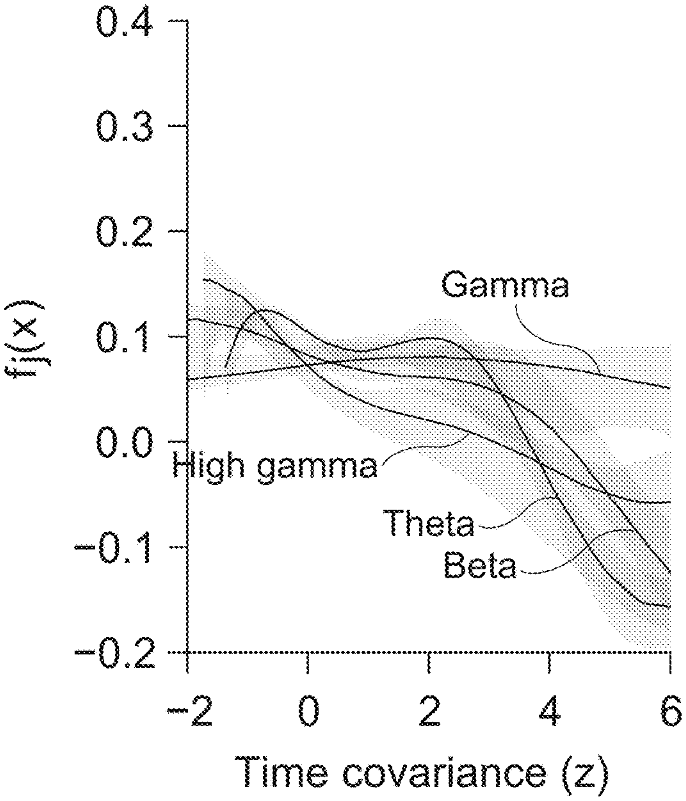
Figure 12A:
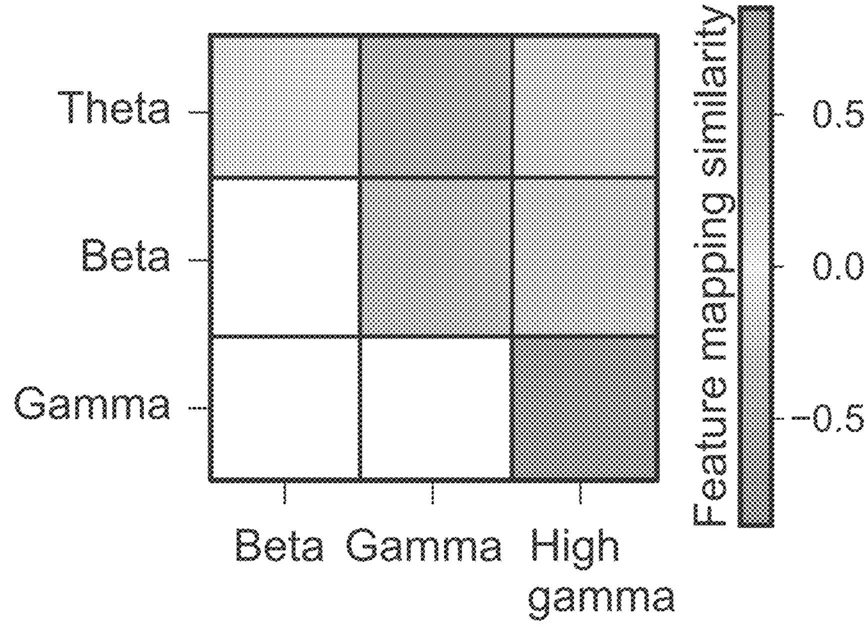
FIGS. 12A-12E are heatmaps of similarities of feature mappings between models trained for different frequency bands for different experiment blocks in accordance with embodiments of the present technology.
Figure 12B:
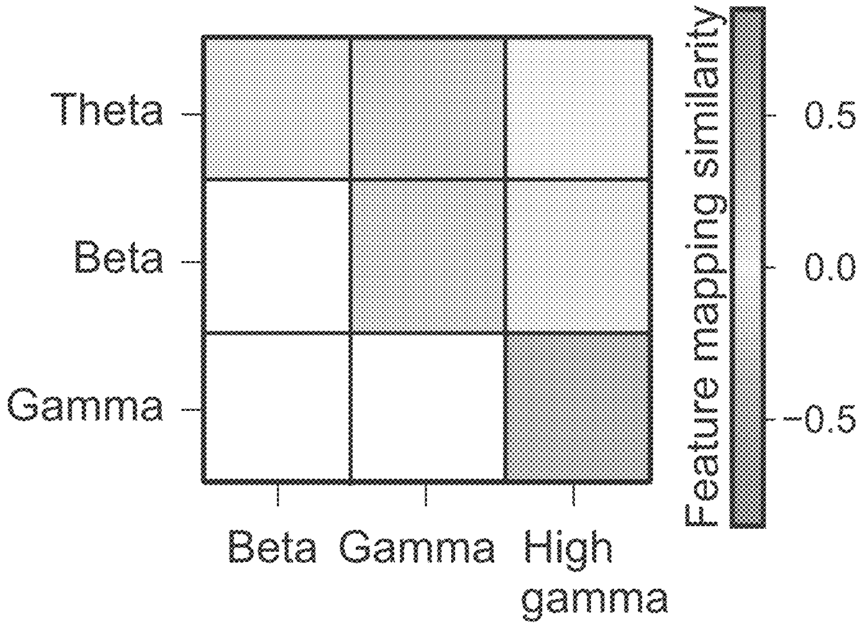
Figure 12C:
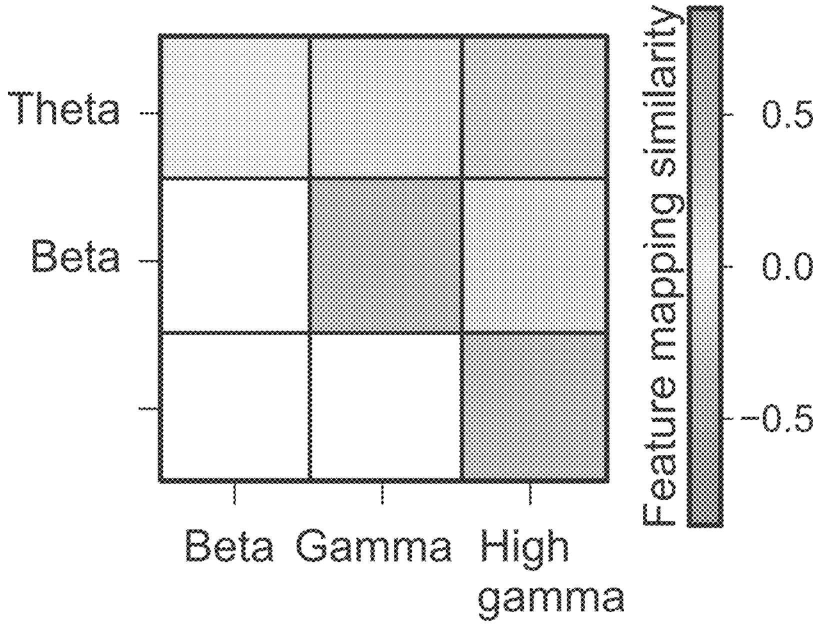
Figure 12D:
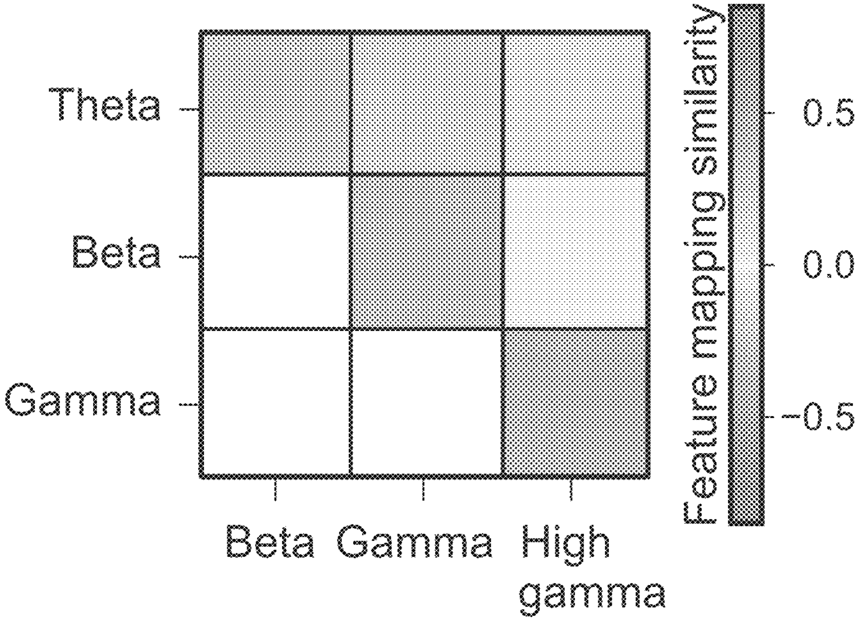
Figure 12E:
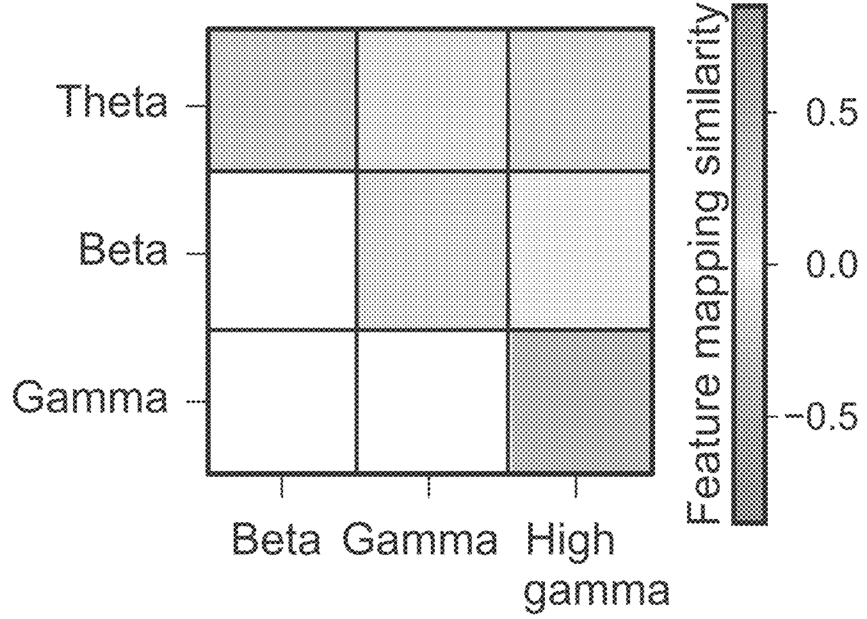

FIG. 8B is a graph of Heatmap of average cosine similarity between feature mappings of SS-FCC and RS-FCC over frequencies in accordance with an embodiment of the present technology.

FIGS. 8C-8G are graphs of comparison of feature mappings for SS-FCC and RS-FCC models for theta band where features are respectively anatomical region of electrodes, electrode pair distance, time covariance (z-scored), initial coherence, and coherence difference.

FIGS. 8H-8L are graphs of comparison of feature mappings for SS-FCC and RS-FCC models for high-gamma band where features are respectively anatomical region of electrodes, electrode pair distance, time covariance (z-scored), initial coherence, and coherence difference.

The inventors observed that feature mappings exhibited high similarity in all frequency bands (FIG. 8B). Notably, the groups with the highest similarity between SS-FCC and RS-FCC feature mappings were the network features in the Theta and High-gamma bands. We plot representative SS-FCC and RS-FCC feature mappings of five features from the Theta and High-gamma models in FIGS. 8C and 8D.

Repeated Stimulation Modifies Mappings from Features to Functional Connectivity Changes The modeling approach employed thus far constrained the learned feature mappings to be constant across all temporal blocks of an experimental session. The influence of the block's time location was represented by a learned global shift in the FCC between all electrode pairs measured in that block. Without being tied to the theory, it is believed that successive stimulation blocks within an experiment had a more complex effect on FCC than a simple average shift, and rather modified the actual feature mappings over the time course of stimulation. We tested this expectation by allowing the nonlinear relationship between each feature and the response to vary across the five stimulation blocks by adding an interaction term between the block number feature and all other features. Rather than averaging over potential heterogeneity in the network dynamics resulting from the accumulated effects of stimulation, this approach allowed for the investigation of a time-course of smoothly varying predictors of coherence changes.

FIGS. 9A-9E are bar graphs indicating r-squared accuracy on held-out data of the time-varying and static model predictions for different experiment blocks in accordance with embodiments of the present technology. Results in FIGS. 9A-9E correspond to prediction of SS-FCC; results are similar for prediction of RS-FCC. Bar graphs indicating r-squared accuracy on held-out data of the time-varying and static model predictions. Greyscale bars indicate the static model while shaded bars indicate the time-varying model. The time-varying models outperformed the static model over all frequencies and experiment blocks. Error bars indicate 95% confidence intervals.

FIGS. 10A-10E are graphs indicating feature mappings of initial coherences for different experiment blocks in accordance with embodiments of the present technology. We observed that the feature mappings change over successive experiment blocks. Shading indicates 95% confidence intervals.

FIGS. 11A-11E are graphs indicating feature mappings of time covariance for different experiment blocks in accordance with embodiments of the present technology. Shading indicates 95% confidence intervals.

FIGS. 12A-12E are heatmaps of similarities of feature mappings between models trained for different frequency bands for different experiment blocks in accordance with embodiments of the present technology. The illustrated results correspond to different frequency bands. Similarity was quantified by feature-averaged cosine similarity of the feature mappings. We observed that while feature mappings were similar at the onset of the stimulation, they diverged over the time-course of stimulation.

It is believed that repeated stimulation indeed produces such heterogeneity across blocks within a session, the inventors found a substantial improvement in prediction quality with the time-varying model for both SS-FCC ($R^2$ Theta 0.426, Beta 0.247, Gamma 0.415, High-gamma 0.527) (FIGS. 9A-9E) and RS-FCC ($R^2$ Theta 0.410, Beta 0.251, Gamma 0.359, High-gamma 0.436) over the static model. We also calculated the cosine similarities of feature mappings for each block of the time-varying SS-FCC model and found that successive stimulation results in the mappings diverging from each other, as their similarity decreased over subsequent blocks (FIGS. 12A-12E). These results indicate that the relationship between features and connectivity change evolved dynamically over the course of repeated stimulation.

DISCUSSION

Here we leverage advances in neural interface technology and interpretable machine learning to induce and model large-scale FCC. We augment the standard framework of stimulation-induced FCC by considering the effects of the pre-existing network structure and by analyzing FCC over a large-scale (~1 $cm^2$) network. We show that stimulation induces widespread FCC in both the stimulated-state and the resting-state, and that the underlying network structure mediates these effects. Our modeling framework represents a readily translatable method of characterizing the underlying network structure to predict the outcome of stimulation. Our findings explain inconsistent results historically reported in vivo and pave the way for increased understanding and development of neural stimulation interventions.

The Influence of the Stimulation Protocol

While brain stimulation can be delivered to a local area, the highly-interconnected nature of the brain ensures that any local region tightly modulates and is modulated by other regions. An analysis of the effects of stimulation which only considers the stimulation protocol thus prioritizes the direct, local effect of stimulation over the mediation of the response by the brain network.

For neural stimulation interventions targeting longer-term FCC in vivo, the protocol-focused approach has been found lacking. The dominant framework for stimulation-induced targeted connectivity change was developed in vitro, a setting in which the cortical network is largely nonexistent and the stimulation protocol can be extremely precise.

Attempts to translate STDP from its native context of monosynaptic connectivity between isolated neuron pairs in vitro to functional connectivity between larger-scale neural structures in vivo have been largely inconsistent, with some reports of promising results, but also of off-target (unstimulated) connectivity changes and a lack of response to the protocols.

We studied real-time network-level FCC as SS-FCC and longer-term FCC as RS-FCC. We found that, in accordance with existing protocol-focused approaches, the stimulation protocol influences both SS-FCC and RS-FCC. However, further analysis indicated that this influence is minor, and that a protocol-focused analysis of stimulation only explains a small fraction of the effects. This represents a substantial departure from the standard analysis of the effects of stimulation which prioritizes the stimulation protocol.

Our observation that the stimulation delay was able to predict some RS-FCC between stimulation sites, and that the stimulation delay was one of the top two protocol features for network-wide FCC prediction, is aligned with the delay-focus of STDP-informed connectivity modification approaches. However, the small amount of variance explained by delay indicates that delay alone is not sufficient for accurate FCC control.

Network-Level Analysis of Neural Stimulation

The inventors model the cortical network as both the mediator and target of the effects of stimulation. Our focus on the network structure is facilitated by our use of large-scale neurotechnologies for stimulation and recording. We used a ECoG array to record from a cortical network. This differed from past studies in which the inclusion of a small set of unstimulated neural sites had primarily been relegated to that of a statistical control. In addition, the inventors used convection-enhanced delivery of the optogenetic virus to obtain widespread opsin expression, which allowed us to stimulate many distinct sites of the sensorimotor cortex and to record neural activity during stimulation without artifact.

We estimated a complete network between all recording sites by calculating their pairwise coherences, which is highly correlated to other functional connectivity metrics. In addition, unlike metrics such as evoked response, coherence can be calculated in the absence of stimulation. This had the dual advantage of allowing us to estimate connectivity during resting-state blocks and between unstimulated sites. We note that the latter point is especially relevant, as most "network-level" analyses of stimulation only observe a partial network as they do not analyze connectivity between unstimulated regions.

We then incorporated details of the distributed structure of these networks for prediction of FCC. Recent studies have indicated that pairwise coherence between two sites is correlated to their change in coherence following stimulation. However, any pairwise analysis treats connections as independent from another and does not capture the distributed structure of the network. In order to incorporate details of the distributed network structure into our predictive model, the inventors rely on advances in graph theory and theoretical neuroscience. Graph theory is a branch of mathematics concerned with the study of graphs, and has developed metrics for summarizing and comparing graphs, such as clustering coefficients, measurements of centrality, and graph distances. Theoretical neuroscience has similar measures, termed "motifs," which are used to analyze simulated brain networks. Just as simple pairwise connectivity between electrodes describes their first-order connectivity, these measures summarize higher-order, distributed connectivity within a network high_conn. The network features the inventors developed and used in our model were inspired by these existing metrics and similarly encode higher order, distributed connectivity information of the network. For example "coherence with network" and "length 2 path strength" quantify general whole-network connectivity strength between two sites, while "electrode covariance" and "coherence difference" quantify the similarity of connectivity structure to the entire network between two site. Indeed, our model confirmed their relevance by identifying "time covariance" and "coherence difference," two higher-order connectivity metrics, as the relevant features for FCC prediction.

One alternative framework for inducing targeted network-wide FCC is network control theory network, which attempts to use control-theoretic methods to control network activity in real-time. However, it has thus far has been limited to quantifying theoretical controllability of networks rather than inducing targeted FCC. Here, we validate our framework on the maximally clinically-translatable NHP model and demonstrate that it can accurate predict network-level stimulation-induced FCC.

The Cortical Network as the Mediator and Target of Stimulated-State and Resting-State Functional Connectivity Changes Both real-time and long-term modulation of brain networks are relevant for neural stimulation-based medical interventions. Here, the inventors induced, estimated, and modeled network-level FCC which were observed during stimulation as well as after stimulation. The high correlation in FCC and high similarity in feature mappings between the two contexts hint at shared processes underlying SS-FCC and RS-FCC. Practically, this also means that observing stimulation-induced FCC in real-time may lead to more accurate longer-term FCC.

Interventions targeting real-time neuromodulation often do not consider effects beyond local activity modulation. However, this neuromodulation has a secondary effect of altering real-time network synchronization, observed here as network-level SS-FCC, and which persist after stimulation as RS-FCC. As such, the complete effects of these interventions can only be fully understood by augmenting their scope of analysis to include network-level FCC.

Our observation that the underlying network mediates RS-FCC demonstrates that interventions directly targeting RS-FCC must consider the underlying network for accurate induction of connectivity changes. The historical neglect of the underlying network structure in mediating RS-FCC could provide an explanation for reports of off-target connectivity changes and inconsistent connectivity changes between stimulation sites. We note that, while many of these studies use STDP-informed stimulation which is designed to elicit changes in anatomical connectivity, we cannot pinpoint the nature of our observed FCC as either solely anatomical or activity-based, as functional connectivity is related to both.

Finally, our results offer a potential explanation for how underlying network-level functional connectivity shapes the therapeutic response to stimulation. Studies have shown that aberrant functional connectivity underlies many neural disorders, and that neural stimulation alters network-level functional connectivity and can treat neural disorders. As such, therapeutic response to stimulation may be a direct result of a stimulation-induced change from aberrant to healthy network-level functional connectivity. This change may in turn be determined by the underlying network-level functional connectivity, as recent work has indicated that underlying functional connectivity shapes the therapeutic response to stimulation, and here the inventors have also shown that it shapes stimulation-induced network-level FCC.

The Evolving Response to Successive Neural Stimulation

Our observation that the time-ordered block number was an important protocol feature indicates that the temporal location of repetitive stimulation is relevant for consideration. We further investigated this phenomenon with our time-varying model.

With the time-varying model the inventors observed that feature mappings describing the response to stimulation evolve in response to repeated stimulation. This result indicates that stimulation interventions likely need to be adapted over time, as repeatedly stimulating will not repeatedly induce the same response nor even be governed by the same network rules mediating the response. This is consistent with the increased success of some closed-loop neural stimulation interventions over open-loop alternatives, as it acknowledges that the effects of stimulation can be made more accurate when the stimulation is informed by recent neural activity. However, the inventors additionally show that stimulation should be adapted to characteristics of the whole network, not only to local activity.

Interpretable Predictive Modeling Beyond the Linear Paradigm

The inventors rely on network-level treatment of FCC by using a data-driven nonlinear modeling approach. In doing so, the inventors were able to develop an accurate predictive model and estimate feature mappings displaying the relationships between the protocol and network features and FCC. These feature mappings have the dual purpose of elucidating underlying mechanisms of network-level response to stimulation, and informing future stimulation interventions.

Data-driven statistical models often fall into one of two approaches: simplistic linear models or complex "black-box" models. While the simple relationships identified by linear models ensure that the mappings are interpretable, linearity is an assertion, not a property learned from the data, and therefore linear models may not capture the complexity of the true input-output relationships. At the other extreme, prediction-focused black-box models can learn complex input-output mappings at the expense of interpretative ability such as observation of the mappings. The unique modeling approach of the inventive technology demonstrates advantages of each as it can identify complex mappings between the features and FCC while allowing the features mappings to be observed. As it is a data-driven and generalized additive model, it retains the ability of identifying linear mappings when such a mapping is supported by the data, while also being able to identify more complex nonlinear mappings when appropriate.

We found that eliminating the artificial and restrictive assumptions of the linear model yielded dramatically improved predictive performance. In particular, as the complexity of our input features increased from simple stimulation parameters to the actual structure of the cortical network, their feature mappings exhibited strong nonlinearities and thus would not be able to be fully represented by a strictly linear approach.

Finally, in light of recent unsuccessful attempts to model the effects of neural stimulation with nonlinear models, our data-driven method for inferring feature mappings of variable complexity represents a timely contribution for principled and accurate modeling of the effects of brain stimulation.

Neuroscientific and Clinical Utility of Our Insights

Here the inventors have shown that the cortical network structure mediates the response to stimulation, both for real-time and longer-term contexts. Our findings provide a possible explanation for how underlying functional connectivity shapes the therapeutic response to stimulation, and for previously reported inconsistent results of neural stimulation. Our framework, only made possible by advances in neural interfaces, interpretable machine learning, and graph theory, represents an efficient method for parsing network structure for accurate prediction of stimulation-induced FCC. It can be readily applied to other network-informed approaches of neural stimulation, and can be used to interrogate, improve, and develop novel neural stimulation interventions for neural disorders.

LIMITATIONS OF THE INVENTIVE TECHNOLOGY

While the inventors have shown that FCC induced by stimulation are more positive than FCC observed in the control condition, it is possible that the modeled FCC in the stimulation condition are composed of a combination of stimulation-driven changes and natural fluctuations. Regardless, the model represents an accurate method for predicting functional connectivity changes in the presence of stimulation.

Our neural recordings were limited to a ECoG on the primary sensorimotor cortex surface; further work is needed to verify that our findings are consistent across brain regions, at various cortical depths, and at larger and smaller scales. In addition, as all stimulation experiments consisted of paired optogenetic stimulation, our observations should be verified with other stimulation modalities and protocols to verify their generality. Our method for parsing the network structure, along with the hierarchical additive model, can be easily extended to these cases. If our findings are verified across a broad range of brain regions and stimulation modalities, then this would indicate that existing stimulation-based therapies must factor in the underlying network in order to arrive at a complete understanding of their effects.

Here the inventors have constructed a set of network features which the inventors have shown are relevant for FCC prediction. While some interpretable mappings of interest were described in the results section, others which were more complicated, such as the relevant "time covariance" feature, could not be easily interpreted. Our features broadly encapsulate various spatiotemporal connectivity motifs present in the network connectivity, and as such can be further dissected and parsed for purposes of interpretation. For example, the importance of "time covariance" indicates that the temporal relations of pairwise coherence contains information relevant for FCC prediction; this knowledge can be used to construct more detailed studies with the goal of uncovering the underlying processes governing this relation.

Our finding that the network mediates the plastic response to stimulation can guide the development of stimulation treatments, but does not explicitly offer a prescriptive method for specifying an exact stimulation protocol. Instead, our model acts as an encoder which yields a prediction for the effects of stimulation given a specific stimulation protocol and network state. The creation of a corresponding decoder could be used to directly prescribe a stimulation protocol to elicit desired FCC. Such a model could also be deployed in real-time as a network-informed controller for FCC.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

What is claimed is:

1. A method for brain stimulation, comprising:

delivering an input stimulus to an area of a brain, via a cortical implant;

in response to delivering the input stimulus, generating neural response signals in the brain determining a predicted outcome of the input stimulus by a nonlinear model, wherein the predicted outcome is based on a set of data derived from the nonlinear model that combines:

protocol features that are brain agnostic, and network features that are based on interactions between neural nodes of the brain, wherein the network features are computed from local field potential (LFP) time series recorded during a resting-state block;

updating the input stimulus into an evolved therapeutic input stimulus dynamically over time based on the predicted outcome;

obtaining a coherence tensor by time-concatenation of coherence matrices across windows in the resting-state block that precedes the evolved therapeutic input stimulus for which functional connectivity changes (FCC) are predicted;

deriving the functional connectivity changes (FCC) from the coherence tensor, assessing importance of the network features by evaluating a difference in a predictive outcome between the nonlinear model and a model fit, wherein the model fit is the nonlinear model without one or more network features of interest;

delivering the evolved therapeutic input stimulus to the brain through the cortical implant; and in response to delivering the evolved therapeutic input stimulus, generating evolved neural response signals in the brain.

2. The method of claim 1, further comprising recording the neural response signals from a surface of the brain or a depth of the brain, wherein the neural response signals from the brain represent brain activity.

3. The method of claim 1, further comprising delivering the input stimulus through implant electrodes of the cortical implant.

4. The method of claim 3, further comprising delivering an optical stimulus by the implant electrodes, wherein the implant electrodes are at least partially transparent.

5. The method of claim 4, further comprising generating the optical stimulus is generated by a laser.

6. The method of claim 3, further comprising delivering an electrical stimulus by the implant electrodes.

7. The method of claim 1, wherein the protocol features comprise a distance between stimulation sites and recording electrodes of the cortical implant.

8. The method of claim 1, wherein the protocol features comprise delays between individual stimulation sites.

9. The method of claim 1, wherein the protocol features comprise anatomical locations of implant electrodes of the cortical implant.

10. The method of claim 1, wherein the protocol features comprise a timing of the input stimulus.

11. The method of claim 1, wherein the network features are selected from a group consisting of: an initial coherence, a coherence within network, a coherence difference, a coherence within stimulation sites, and a coherence difference between a recording electrode and at least one other electrode of the cortical implant.

12. The method of claim 1, wherein the network features are selected from a group consisting of: an electrode covariance, and a time covariance capture.

13. A method for treating a neural disorder of a subject, comprising:

delivering an input stimulus to an area of a brain, via a cortical implant attached to the subject;

in response to delivering the input stimulus, generating neural response signals in the brain;

recording the neural signals from a surface of the brain or a depth of the brain, wherein the neural signals from the brain represent brain activity;

determining a predicted outcome, wherein the predicted outcome is based on a set of data derived from a nonlinear model that combines;

protocol features that are brain agnostic, and network features that are based on interconnections between neural nodes of the brain, wherein the network features are computed from local field potential (LFP) time series recorded during a resting state block;

updating the input stimulus into an evolved therapeutic input stimulus dynamically over time based on the predicted outcome, obtaining a coherence tensor by time-concatenation of coherence matrices across windows in the resting-state block that precedes the evolved therapeutic input stimulus for which functional connectivity changes (FCC) are predicted;

deriving the functional connectivity changes from the coherence tensor;

assessing importance of the network features by evaluating a difference in a predictive outcome between the nonlinear model and a model fit, wherein the model fit is the nonlinear model without one or more network features of interest;

based on the predicted outcome, delivering the evolved therapeutic input stimulus to the subject through the cortical implant; and in response to delivering the evolved therapeutic input stimulus, generating evolved neural response signals in the brain.

14. The method of claim 13, wherein implant electrodes of the cortical implant are at least partially transparent, the method further comprising delivering an optical stimulus by the implant electrodes.

15. The method of claim 14, further comprising generating the optical stimulus by a laser.

16. The method of claim 13, further comprising delivering an electrical stimulus by implant electrodes of the cortical implant.

17. The method of claim 13, wherein the protocol features are selected from a group consisting of: a distance between stimulation sites and recording electrodes of the cortical implant; and anatomical locations of the implant electrodes of the cortical implant.

18. The method of claim 13, wherein the protocol features are selected from a group consisting of: a timing of stimulus; and delays between individual stimulation sites.

19. The method of claim 13, wherein the network features are selected from a group consisting of: an initial coherence, a coherence within network, a coherence difference, a coherence within stimulation sites, and a coherence difference between a recording electrode and at least one other electrode of the cortical implant.

20. The method of claim 13, wherein the network features are selected from a group consisting of: an electrode covariance, and a time covariance capture.

* * * * *